(12) United States Patent
Lundgren et al.

(10) Patent No.: US 10,364,208 B2
(45) Date of Patent: Jul. 30, 2019

(54) OXIDATIVE COUPLING OF ARYL BORON REAGENTS WITH SP3-CARBON NUCLEOPHILES, AND AMBIENT DECARBOXYLATIVE ARYLATION OF MALONATE HALF-ESTERS VIA OXIDATIVE CATALYSIS

(71) Applicant: The Governors of the University of Alberta, Edmonton (CA)

(72) Inventors: Rylan Lundgren, Edmonton (CA); Patrick Moon, Edmonton (CA)

(73) Assignee: The Governors of the University of Alberta, Edmonton (CA)

(*) Notice: Subject to any disclaimer, the term of this patent is extended or adjusted under 35 U.S.C. 154(b) by 0 days.

(21) Appl. No.: 15/861,020

(22) Filed: Jan. 3, 2018

(65) Prior Publication Data

US 2018/0186721 A1 Jul. 5, 2018

Related U.S. Application Data

(60) Provisional application No. 62/442,676, filed on Jan. 5, 2017.

(30) Foreign Application Priority Data

Jan. 5, 2017 (CA) .................. 2953669

(51) Int. Cl.

| | | |
|---|---|---|
| *C07C 67/32* | (2006.01) | |
| *C07C 69/614* | (2006.01) | |
| *C07C 69/38* | (2006.01) | |
| *C07F 5/02* | (2006.01) | |
| *C07C 67/343* | (2006.01) | |
| *C07C 303/40* | (2006.01) | |
| *C07C 201/12* | (2006.01) | |
| *C07C 315/04* | (2006.01) | |
| *C07C 231/12* | (2006.01) | |
| *C07D 295/185* | (2006.01) | |
| *C07D 213/55* | (2006.01) | |
| *C07D 213/61* | (2006.01) | |
| *C07D 213/64* | (2006.01) | |
| *C07D 307/91* | (2006.01) | |
| *C07F 7/08* | (2006.01) | |
| *C07F 9/40* | (2006.01) | |

(52) U.S. Cl.
CPC ............ *C07C 67/32* (2013.01); *C07C 67/343* (2013.01); *C07C 69/38* (2013.01); *C07C 69/614* (2013.01); *C07C 201/12* (2013.01); *C07C 231/12* (2013.01); *C07C 303/40* (2013.01); *C07C 315/04* (2013.01); *C07D 213/55* (2013.01); *C07D 213/61* (2013.01); *C07D 213/64* (2013.01); *C07D 295/185* (2013.01); *C07D 307/91* (2013.01); *C07F 5/025* (2013.01); *C07F 5/027* (2013.01); *C07F 7/081* (2013.01); *C07F 9/4046* (2013.01); *C07C 2523/72* (2013.01); *C07C 2527/055* (2013.01); *C07C 2527/122* (2013.01); *C07C 2527/26* (2013.01); *C07C 2601/02* (2017.05); *C07C 2601/14* (2017.05)

(58) Field of Classification Search
CPC ... C07C 67/343; C07C 231/12; C07C 315/04; C07C 201/12; C07C 205/56; C07C 233/11; C07C 233/65; C07C 233/66; C07C 233/74; C07C 235/34; C07C 311/21; C07C 317/44; C07C 317/46; C07C 69/612; C07C 69/63; C07C 69/65; C07C 69/734; C07C 69/738; C07C 69/76; C07C 2523/72; C07C 2527/055; C07C 2527/122; C07C 2527/26; C07C 2601/02; C07C 2601/14; C07C 67/32; C07C 69/38; C07C 69/614; C07D 213/55; C07D 213/61; C07D 213/64; C07D 295/185; C07D 307/91; C07F 5/025; C07F 5/027; C07F 7/081; C07F 9/4046
See application file for complete search history.

(56) References Cited

PUBLICATIONS

Unoh et al. (Palladium-Catalyzed Decarboxylative Arylation of Benzoylacrylic Acids toward the Synthesis of Chalcones, J, Org. Chem., 78, pp. 5096-5102, published Apr. 2013) (Year: 2013).*
Lundgren et al. (Ambient Decarboxylative Arylation of Malonate Half-Esters via Oxidative Catalysis, J. Am. Chem. Soc., 138, pp. 13826-13829, published Oct. 2016) (Year: 2016).*
Moon et al., "Ambient Decarboxylative Arylation of Malonate Half-Esters via Oxidative Catalysis," Journal of the American Chemical Society, Oct. 2016, vol. 138 (42), pp. 13826-13829.
Moon et al., "Oxidative Coupling of Aryl Boron Reagents with sp3-Carbon Nucleophiles: The Enolate Chan-Evans-Lam Reaction," Angewandte Chemie International Edition, Jan. 2016, vol. 55 (5), pp. 1894-1898.

* cited by examiner

Primary Examiner — Jafar F Parsa
Assistant Examiner — Blaine G Doletski
(74) Attorney, Agent, or Firm — Borden Ladner Gervais LLP

(57) ABSTRACT

Described herein are methods of oxidative coupling of aryl boron reagents with sp³-carbon nucleophiles, and ambient decarboxylative arylation of malonate half-esters via oxidative catalysis.

8 Claims, 11 Drawing Sheets

Oxidative Coupling of Aryl Boron Reagents with Heteroatom Nucleophiles (Chan-Evans-Lam Reaction)

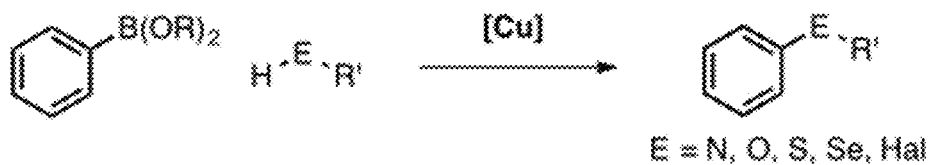

E = N, O, S, Se, Hal

This Work: Oxidative Coupling of Aryl Boron Reagents with Enolates

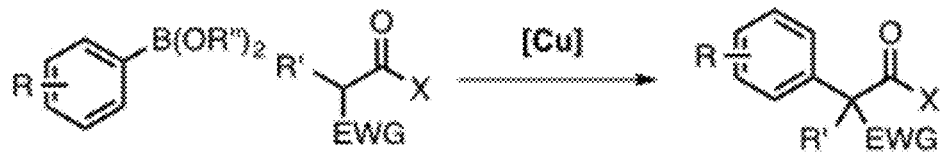

- mild reaction conditions
- complements cross-coupling/$S_NAr$
- tolerates aryl/alkyl halides
- enolate can be tertiary

Scope and Diversity:
X = OR, $NR_2$; EWG = ester, amide, sulfonyl, phosphonyl; R' = H, alkyl, aryl

FIG. 1

Examples of drugs that contain polyfunctionalized acetic acid moieties

Deviations from standard conditions [ y: yield, c: conversion]

| Ar–B | y (%) | (% c) | Cu Source | y (%) | (% c) | Conditions | y (%) | (% c) |
|---|---|---|---|---|---|---|---|---|
| (ArBO)$_3$ | 68 | (98) | Cu(OAc)$_2$ | 14 | (74) | O$_2$ instead of air | 31 | (99) |
| ArB(OH)$_2$ | 19 | (59) | CuSO$_4$ | 20 | (42) | RCO$_2$K half ester | 36 | (39) |
| ArBpin | 40 | (99) | Cu(MeCN)$_4$PF$_6$ | 73 | (99) | no Et$_3$N | 0 | (0) |
| ArBF$_3$K | 0 | (42) | CuI | 70 | (99) | 1.2 equiv Ar-B | 74 | (99) |

0.2 mmol scale
0.5 dram vial 0.5 mmol scale
1 dram vial

OXIDATIVE COUPLING OF ARYL BORON REAGENTS WITH SP3-CARBON NUCLEOPHILES, AND AMBIENT DECARBOXYLATIVE ARYLATION OF MALONATE HALF-ESTERS VIA OXIDATIVE CATALYSIS

CROSS REFERENCE TO RELATED APPLICATION

The application claims priority to U.S. 62/442,676, filed Jan. 5, 2017, and Canadian Patent Application 2,953,669, filed Jan. 5, 2017, the entire contents both of which are hereby incorporated by reference.

FIELD

The present disclosure relates generally to methods of oxidative coupling of aryl boron reagents with $sp^3$-carbon nucleophiles, and ambient decarboxylative arylation of malonate half-esters via oxidative catalysis.

BACKGROUND

Cross-coupling reactions between two distinct nucleophilic partners have emerged as valuable transformations that display reactivity and selectivity orthogonal to classical metal-catalyzed couplings of electrophiles with nucleophiles. Oxidative coupling reactions often proceed under exceptionally mild conditions, employ base-metal mediators or catalysts, and in ideal cases, tolerate electrophilic functionality useful for subsequent transformations. The Cu-mediated union of aryl boronic acids and heteroatom nucleophiles exemplifies the power of such coupling manifolds. First reported by Chan and Lam, and Evans, functionalized aniline and phenol derivatives can be prepared from stable, readily available aryl boron species at room temperature by employing simple Cu-salts and mild organic bases. In addition to N- and O-based nucleophiles, sulfur, selenium, tellurium, and halogen nucleophiles are also suitable partners in these reactions. Despite the success of Chan-Evans-Lam type reactions in carbon-heteroatom bond construction processes, as well as an increasing appreciation for the mechanism of these transformations, a general method for the Cu-mediated arylation of stabilized $sp^3$-carbon-based nucleophiles with organoboron reagents has not been established.

In the biosynthesis of polyketides and fatty acids, carbon-carbon bond formation proceeds via decarboxylative cross-condensation between malonic acid derivatives such as malonyl-CoA and enzyme-bound acyl electrophiles. A variety of conceptually related metal- or organocatalyzed reactions have been developed, in which malonates and related species undergo decarboxylation and coupling with carbonyl or allylic electrophiles. These reactions obviate the need for high temperatures, strongly basic mediators or prior stoichiometric manipulations to generate the enolate component. By contrast, there are limited reports of decarboxylative coupling reactions of malonate derivatives with aryl electrophiles.

SUMMARY

In one aspect there is described herein a
method for arylation of an $sp^3$ carbon nucleophile, comprising: reacting
 a. an arylboroxine;
 b. an $sp^3$-carbon nucleophile,
 c. a copper based stoichiometric promoter, and
 d. triethylamine,
the reaction taking place at a temperature of about room temperature to about 40° C., thereby creating a carbon-carbon bond.

In one aspect, there is described a method for arylation of an activated $sp^3$-carbon-based nucleophile, comprising: reacting
 a. a compound Ar—B(OR)$_2$, wherein R=alkyl;
 b. an $sp^3$-carbon nucleophile,
 c. a copper based stoichiometric promoter, and
 d. triethylamine,
the reaction taking place at a temperature of about room temperature to about 40° C., thereby creating a carbon-carbon bond.

In one example, the reaction is exposed to air.

In one example, said $sp^3$-carbon nucleophile is diethyl malonate, diisopropyl malonate, dibenzyl malonate, dimethylmalonate, diethyl ethylmalonate, diethyl methylmalonate, amido ester, sulfonyl amide, phosphonyl ester, or sulfonyl ester.

In one example, the reaction further comprising an acetate salt.

In one example, said acetate salt is CsOAc or NaOAc.

In one example, the copper based stoichiometric promoter is Cu(OTf)$_2$, Cu(OAc)$_2$, Cu(OMe)$_2$, or CuSO$_4$.

In one aspect there is described a method for decarboxylative carbonyl α-arylation, comprising: reacting
 a. an aryl coupling partner,
 b. a carboxylic acid, and
 c. a copper based catalyst In one example, the reaction taking place at room temperature, exposed to air, thereby creating a carbon-carbon bond.

In one example, said carboxylic acid is a malonic acid derivative.

In one example, said carboxylic acid is a malonate ester, monoethyl malonate, monobenzyl malonate, mono-1-chlorohexyl malonate, mono-4-NBoc-piperidyl malonate, mono-geranyl malonate, 3-(methyl(phenyl)amino)-3-oxopropanoic acid, 3-oxo-3-(phenylamino)propanoic acid, 3-oxo-3-(pyrrolidin-1-yl)propanoic acid, or 3-(methoxy(methyl)amino)-3-oxopropanoic acid.

In one example, said coupling partner is an arylboronic ester or heteroaryl boronic ester.

In one example, said coupling partner is 3-iodophenyl boronic neopentyl ester [B(neop)], (ArBO)$_3$, ArB(OH)$_2$, ArBpin, or ArBF$_3$K.

In one example, said copper based catalyst is a Cu(I) salt.
In one example, said copper based catalyst is a Cu(II) salt.
In one example, said copper based catalyst is Cu(OTf)$_2$, Cu(OAc)$_2$, CuSO$_4$, Cu(MeCN)$_4$PF$_6$, or CuI.

Other aspects and features of the present disclosure will become apparent to those ordinarily skilled in the art upon review of the following description of specific embodiments in conjunction with the accompanying figures.

BRIEF DESCRIPTION OF THE FIGURES

Embodiments of the present disclosure will now be described, by way of example only, with reference to the attached Figures.

FIG. 1 is an overview of the Cu-mediated oxidative coupling of heteroatom nucleophiles and the oxidative carbonyl α-arylation developed herein.

DETAILED DESCRIPTION

Figure 2A:
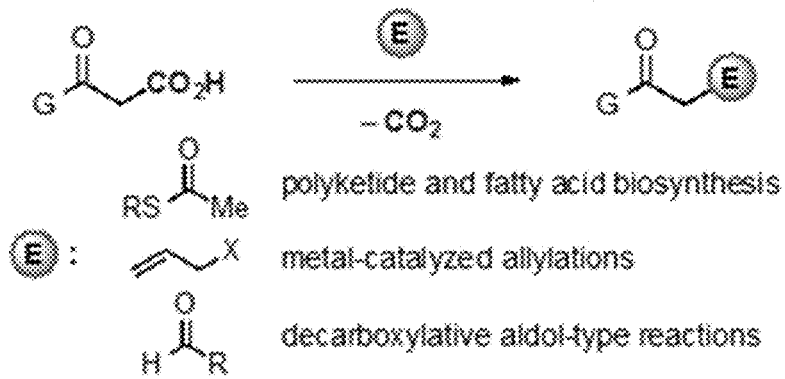
FIG. 2A-D depicts reactivity of malonic acid derivatives (FIG. 2A), Cu-mediated oxidative coupling with heteroatom nucleopphiles (FIG. 2B), nucleophilic arylation of malonic acids (FIG. 2C), and α-aryl carbonyl structures in bioactive molecules (2D).

As used herein, the term "hydrocarbon," used alone or in combination, refers to a linear, branched or cyclic organic moiety comprising carbon and hydrogen, for example, alkyl, alkene, alkyne, and aryl, which may each be optionally substituted. A hydrocarbon may, for example, comprise about 1 to about 60 carbons, about 1 to about 40 carbons, about 1 about 30 carbons, about 1 about 20 carbons, about 1 to about 10 carbons, about 1 to about 9 carbons, about 1 to about 8 carbons, about 1 to about 6 carbons, about 1 to about 4 carbons, or about 1 to about 3 carbons. In some embodiments, hydrocarbon comprises 10 carbons, 9 carbons, 8 carbons, 7 carbons, 6 carbons, 5 carbons, 4 carbons, 3 carbons, 2 carbons, or 1 carbon. In the case of polymers having hydrocarbon backbones and/or branches, the number of carbons could be much higher.

The term "alkyl", used alone or in combination, means a straight or branched hydrocarbon group as defined above. In some embodiments, alkyl has about 1 to about 60 carbons, about 1 to about 40 carbons, about 1 about 30 carbons, about 1 to about 20, 1 to about 10, 1 to about 8 or 1 to about 6 carbons. Examples of branched or unbranched $C_1$-$C_8$ alkyl groups include, for example, methyl, ethyl, propyl, isopropyl, butyl, isobutyl, tert-butyl, the isomeric pentyls, the isomeric hexyls, the isomeric heptyls, and the isomeric octyls.

As used herein, "heteroalkyl" refers to a linear, branched or cyclic alkyl group wherein one or more carbons is replaced with a heteroatom, such as S, O, P and N. Exemplary heteroalkyls include alkyl ethers, secondary and tertiary alkyl amines, amides, alkyl sulfides, and the like.

The term "alkoxy", used alone or in combination, means the group —O-alkyl, wherein the alkyl group is as defined above. Examples include, for example, methoxy, ethoxy, n-propyloxy, and iso-propyloxy.

The term "cycloalkyl", used alone or in combination, means a cyclic alkyl group having at least 3 carbon atoms, wherein alkyl is as defined above. Examples of $C_3$-$C_8$ cycloalkyl groups include cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl and cycloheptyl.

The term "alkenyl", used alone or in combination, means a straight or branched chain hydrocarbon having at least 2 carbon atoms, which contains at least one carbon-carbon double bond. In some embodiments, alkenyl has about 2 to about 60 carbons, about 2 to about 40 carbons, about 2 about 30 carbons, about 2 to about 8 carbons. In some embodiments, alkenyl has 2 to 8 carbon atoms. Examples of alkenyl groups include, for example, vinyl, allyl, isopropenyl, pentenyl, hexenyl, heptenyl, 1-propenyl, 2-butenyl and 2-ethyl-2-butenyl.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

The term "alkynyl", used alone or in combination, means a straight or branched chain hydrocarbon having at least 2 carbon atoms, which contains at least one carbon-carbon triple bond. In some embodiments, alkynyl has about 2 to about 60 carbons, about 2 to about 40 carbons, about 2 about 30 carbons, about 2 to about 8 carbons. Examples of alkynyl groups include, for example, ethynyl, 1-propynyl, 1- and 2-butynyl, and 1-methyl-2-butynyl.

Alkyl, alkoxy, cycloalkyl, alkenyl and alkynyl groups can either be unsubstituted or substituted with one or more substituents, for example, halogen, alkyl, alkoxy, acyloxy, amino, amido, cyano, hydroxyl, mercapto, carboxy, carbonyl, benzyloxy, aryl, and heteroaryl.

The term "alkenylene" means a divalent form of an alkenyl group, as defined above.

The term "alkynylene" means a divalent form of an alkynyl group, as defined above.

The term "cycloalkylene" means a divalent form of a cycloalkyl group, as defined above.

The term "alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, I-methyl-2-methoxyethyl, I-(2-methoxyethyl)-3-methoxypropyl, and I-(2-methoxyethyl)-3-methoxypropyl.

The term "alkylcarbonyl" means a moiety of the formula —C(O)—R, where R is alkyl as defined herein.

The term "alkoxycarbonyl" means a moiety of formula —C(O)—R wherein R is alkoxy as defined herein.

"Alkylsulfanyl" means a moiety of the formula —S—R wherein R is alkyl as defined herein.

"Alkylsulfinyl" means a moiety of the formula —SO—R wherein R is alkyl as defined herein.

"Alkylsulfonyl" means a moiety of the formula —$SO_2$—R' where R' is alkyl as defined herein.

"Aminosulfonyl" means a moiety of the formula —$SO_2$—R' where R' is amino as defined herein.

"Hydroxyalkyl" refers to an alkyl moiety as defined herein that is substituted with one or more, preferably one, two or three hydroxy groups, provided that the same carbon atom does not carry more than one hydroxy group.

The term "amine" means a primary, secondary or tertiary amine, wherein one two or three hyrdogens of ammonia are substituted, respectively.

The term "amino" means a primary amino group or a secondary amino group, wherein one or both hydrogens of an —NH2 group are substituted, respectively.

The term "substituted amino" means an amino group mono- or di-substituted with alkyl, alkenyl, alkynyl, cycloalkyl, alkoxy, aryl, substituted aryl, heteroaryl, substituted heteroaryl, alkylcarboxy, arylcarboxy, heteroarylcarboxy, or alkoxycarbonyl.

The term "aryl", used alone or in combination, means an aromatic carbocyclic moiety of up to 60 carbon atoms, which may be a single ring (monocyclic) or multiple rings fused together (e.g., bicyclic or tricyclic fused ring systems). In some embodiments, aryl has up to 60 carbon atoms, up to 40 carbon atoms, up 20 carbon atoms, up to 12 carbon atoms, up to 10 carbon atoms, up to 9 carbon atoms, or up to 6 carbon atoms. Any suitable ring position of the aryl moiety may be covalently linked to the defined chemical structure. Examples of aryl moieties having up to 20 carbons include, but are not limited to phenyl, naphthyl (e.g. 1-naphthyl, 2-naphthyl, dihydronaphthyl, or tetrahydronaphthyl), anthryl, phenanthryl, fluorenyl, indanyl, acenaphthenyl, acenaphthylenyl, and the like.

The term "substituted aryl" means an aryl, as defined above, having from one to multiple substituents, such as, but not limited to, alkyl, alkenyl, alkynyl, cycloalkyl, alkoxy, halogen, carboxy, alkoxycarbonyl, hydroxy, aryl, heteroaryl, amino, trifluoromethyl, $R^A$-substituted alkyl, halo, cyano, nitro, —$SR^A$, —$OR^A$, —$C(O)R^A$, —$OC(O)R^A$, —$SO_2OR^A$, —$OSO_2R^A$, —$SO_2NR^AR^B$, —$NR^ASO_2R^A$, —$C(O)OR^A$, —$NR^A{}_2$,

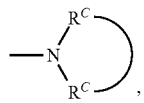

—$CONR^A{}_2$, Or —$NR^AC(O)R^A$, where each $R^A$ is independently hydrogen, lower alkyl, $R^B$-substituted lower alkyl, aryl, $R^B$-substituted aryl, heteroaryl, heteroaryl(lower)alkyl, aryl(lower)alkyl, or $R^B$-substituted aryl(lower)alkyl, where each $R^C$ is independently lower alkyl, $R^B$-substituted lower alkyl, aryl, $R^B$-substituted aryl, heteroaryl, heteroaryl(lower)alkyl, aryl(lower)alkyl, or $R^B$-substituted aryl(lower)alkyl, where each $R^B$ is, independently, hydroxy, halo, lower alkoxy, oxetan-3-yl-lower alkoxy, (3-lower alkyl-oxetan-3-yl)lower alkoxy, cyano, thio, nitro, lower alkyl, halo-lower alkyl, or amino. In addition, any two adjacent substituents on the aryl may optionally together form a lower alkylenedioxy. In some embodiments, substituents on the substituted aryl include hydroxy, halo, lower alkoxy, cyano, thio, nitro, lower alkyl, halo-lower alkyl, 6-[(3-ethyloxetan-3-yl)methoxy]hexan-1-oxy or amino.

The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyi, sidfo-oxo, thiol, or boro as described herein.

The term "aryloxy", used alone or in combination, means the group —O-aryl, wherein the aryl group is as defined above. The term "heteroaryloxy", used alone or in combination, means the group —O-heteroaryl, wherein the heteroaryl group is as defined above.

The term "arylene" means a divalent form of an aryl, as defined above, such as ortho-phenylene, meta-phenylene, para-phenylene, and the naphthylenes. The term "heteroarylene" means a divalent form of a heteroaryl radical, as defined above.

The term "aryloxy", used alone or in combination, means the group —O-arylene, wherein the arylene group is as defined above. The term "heteroaryloxy", used alone or in combination, means the group —O-heteroarylene, wherein the heteroarylene group is as defined above.

The term "halide" or "halogen" as used herein refers to the fluorine, chlorine, bromine, and iodine.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "ester" as used herein is represented by the formula —$(OC(O)A1$ or —$C(O)OA1$, where A1 can be alkyl, cycloalkyl, alkenyl, cycloalkenyl, alkynyl, cycloalkynyl, arvl, or heteroaryl group as described herein.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycioalkynyi, aryl, or heteroaryl group as described herein.

The term "malonic acid" refers to 1,3-propanedioic acid, a dicarboxylic acid with structure $CH_2(COOH)_2$. The ion form of malonic acid, as well as its esters and salts, are known as malonates. For example, diethyl malonate is ethyl ester of malonic acid.

The term "malonic acid derivative," as used herein includes not only malonic acid and -substituted malonic acid but also malonic acid esters, malonic acid ester amides, malonic acid dihalogenides and other derivatives.

The term "biarylene" means a bidentate group comprising two aryl groups attached together by a single bond, and having a point of attachment on each aryl group. The term "heterobiarylene" means a bidentate group comprising two heteroaryl groups attached together by a single bond, and having a point of attachment on each heteroaryl group.

The term "biaryloxy" means a bidentate group comprising two aryloxy groups attached together by a single bond, and having a point of attachment on the oxygen atom of each aryloxy group. The term "heterobiaryloxy" means a bidentate group comprising two heteroaryloxy groups attached together by a single bond, and having a point of attachment on the oxygen atom of each heteroaryloxy group.

As used herein, the term "solution" is intended to encompass homogeneous solutions as well as dispersions. Similarly, the term "solvent" is intended to encompass a solvent that completely dissolves a solute as well as a dispersing medium.

As used herein, the term "mixing" is intended to encompass any suitable means of combining two or more elements, including mixing, admixing, combining, contacting, blending, and the like.

Room temperature (also referred to as ambient temperature) refers to a temperature ranging for example from about 20° C. to about 25° C.

Example I—Oxidative Coupling of Aryl Boron Reagents and Heteroatom Nucleophiles

The contents of Moon, P. J., Halperin, H. M., Lundgren, R. J. (2016) "Oxidative Coupling of Aryl Boron Reagents with sp³-Carbon Nucleophiles: The Enolate Chan-Evans-Lam Reaction." Angew. Chem. Int. Ed. 55. 1894-1898, and the Supplementary Information therein, is hereby incorporated by reference in their entirety.

In one aspect, there is described a method for arylation of an sp³ carbon nucleophile, comprising: reacting an arylboroxine; an sp³-carbon nucleophile, and a copper based catalyst, the reaction taking place in the presence of triethylamine, at a temperature of about room temperature to about 40° C., exposed to air, thereby creating a carbon-carbon bond.

Oxidative Coupling of Aryl Boron Reagents with Heteroatom Nucleophilies (Chan-Evans-Lam Reaction)

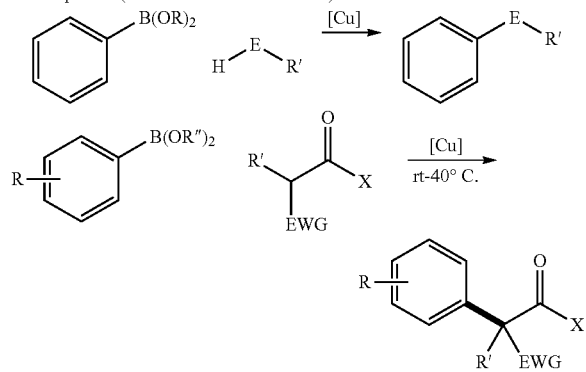

E = N, O, S, Se, Hal
mild reaction conditions tolerates aryl/alkyl halides
complements cross-coupling/S$_N$Ar enolate can be 2° or 3°
X = OR, NR$_2$;
EWG—ester, amide, sulfonyl, phosphonyl;
R' = H, alkyl, aryl In one example, there is described, a method for the arylation of activated methylene species. Under mild conditions, Cu(OTf)$_2$ mediates the coupling of functionalized aryl boron species with a variety of stabilized sp³-nucleophiles. Tertiary malonates and amido esters can be employed as substrates to generate quaternary centers. Complementing traditional cross-coupling or S$_N$Ar protocols, the transformation is chemoselective in the presence of halogen electrophiles, including aryl bromides and iodides. Substrates bearing amide, sulfonyl, and phosphonyl groups, which are not amenable to coupling under mild Hurtley-type conditions, are suitable reaction partners.

In one example, there is described method for arylation of an sp³ carbon nucleophile, comprising: reacting an arylboroxine; an sp3-carbon nucleophile, a copper based stoichiometric promoter, and triethylamine, the reaction taking place at a temperature of about room temperature to about 40° C., thereby creating a carbon-carbon bond.

In one example, there is described a method for arylation of an activated sp³-carbon-based nucleophile, comprising: reacting a neopentylboronic ester; an sp³-carbon nucleophile, a copper based stoichiometric promoter, and triethylamine, the reaction taking place at a temperature of about room temperature to about 40° C., thereby creating a carbon-carbon bond.

In one example, the reaction is exposed to air.

Sp³-Carbon Nucleophile

In one example, the sp³-carbon nucleophile is diethyl malonate, diisopropyl malonate, dibenzyl malonate, dimethylmalonate, diethyl ethylmalonate, diethyl methylmalonate, amido ester, sulfonyl amide, phosphonyl ester, or sulfonyl ester.

In one example, the sp³-carbon nucleophile is diethyl malonate, diethyl methylmalonate, diethyl benzylmalonate, or diethyl 2-(3-chloropropyl)malonate.

Copper Based Stoichiometric Promoter

The reaction mixture comprises a copper based stoichiometric promoter.

In one example, the copper based catalyst is Cu(OTf)$_2$, Cu(OAc)$_2$, Cu(OMe)$_2$, or CuSO$_4$.

Acetate Salt

In one example, the reaction further comprises an acetate salt.

In a specific example, the acetate salt is CsOAc or NaOAc

Reaction Conditions

The reaction is carried out at temperatures, from about ambient temperature (e.g., room temperature) to about 40° C., optionally exposed to air, resulting in the formation of a Carbon-Carbon bond.

We report a versatile new oxidative method for the arylation of activated methylene species. Under mild conditions (rt to 40° C.), Cu(OTf)$_2$ mediates the selective coupling of functionalized aryl boron species with a variety of stabilized sp³-nucleophiles. Tertiary malonates and amido esters can be employed as substrates to generate quaternary centers. Complementing traditional cross-coupling or S$_N$Ar protocols, the transformation is chemoselective in the presence of halogen electrophiles, including aryl bromides and iodides. Substrates bearing amide, sulfonyl, and phosphonyl groups, which are not amenable to coupling under mild Hurtley-type conditions, are suitable reaction partners Cross-coupling reactions between two distinct nucleophilic partners have emerged as valuable transformations that display reactivity and selectivity orthogonal to classical metal-catalyzed couplings of electrophiles with nucleophiles.[1] Oxidative coupling reactions often proceed under exceptionally mild conditions, employ base-metal mediators or catalysts, and in ideal cases, tolerate electrophilic functionality useful for subsequent transformations. The Cu-mediated union of aryl boronic acids and heteroatom nucleophiles exemplifies the power of such coupling manifolds.[2] First reported by Chan and Lam,[3] and Evans,[4] functionalized aniline and phenol derivatives can be prepared from stable, readily available aryl boron species at room temperature by employing simple Cu-salts and mild organic bases. In addition to N- and O-based nucleophiles, sulfur, selenium, tellurium, and halogen nucleophiles are also suitable partners in these reactions.[2,5,6]

Despite the success of Chan-Evans-Lam type reactions in carbon-heteroatom bond construction processes, as well as an increasing appreciation for the mechanism of these transformations,[7] a general method for the Cu-mediated arylation of stabilized sp³-carbon-based nucleophiles with organoboron reagents has not been established. This is particularly noteworthy in light of the importance of α-aryl carbonyl compounds in synthetic organic and medicinal chemistry and the considerable body of literature concerning transition-metal-based methods for their synthesis via the coupling of sp²-electrophiles.[8-10] Indeed, in comparison to heteroatom nucleophiles, reports of Cu promoting C—C bond forming reactions with aryl boron reagents under oxidative conditions remain sparse.[11-12] To the best of our knowledge, enamine annulation[13] and vinylation[14] represent the closest known reports towards an enolate Chan-Evans-Lam reaction. Currently available oxidative arylation strategies employing organoboron reagents and activated methylenes require stoichiometric Pb(OAc)$_4$ in combination with Hg additives.[15] Motivated by this methodological gap and the opportunity to access compound classes not easily prepared by existing protocols, we report herein the first Cu-mediated oxidative coupling reactions between aryl boroxines or boronic esters and in-situ formed enolates to generate α-aryl carbonyl compounds (FIG. 1). The reaction is chemoselective in the presence of halogen electrophiles (including aryl iodides) and can be employed on substrate classes that are not amenable to Hurtley-type reactions under mild conditions (<70° C.), such as amides and tertiary malonate esters.

With the aim of developing Cu-mediated oxidative C—C bond formation between an aryl boron species and an activated sp$^3$-nucleophile, reaction conditions similar to those established for heteroatom arylations were investigated, generally without success. Typical side products arising from protodeborylation, aryl-aryl homocoupling and acetoxylation were observed under standard Chan-Evans-Lam conditions.[2,14] The use of aryl boronic anhydrides (boroxines) however, provided a breakthrough in reactivity. Table 1A is illustrative; under standard reaction conditions, aryl boronic acids or pinacol boronic esters provided only trace conversion to the desired arylated malonate product (2% and 7% respectively), while the aryl boroxine provided excellent yields (86%) and minimal side product formation.[16a] The corresponding neopentyl boronic ester also provided lower, but acceptable conversion to the product (68%). The transformation proceeded smoothly at room temperature with no observable side-reactions at the electrophilic aryl bromide site.

Cu(OTf)$_2$ is the preferred Cu source, as the use of other reagents provided lower yields and increased amounts of protodeborylation (Table 1B, entries 2-4). Triethylamine was essential to the reaction, as other bases were not effective (Table 1B entries 5-7). Acetate salts provided acceleration in reaction rate, but were not essential to product formation (Table 1B entries 8 and 9).[16b] Water had a deleterious effect on the reaction, providing some insight into the poor reactivity observed with aryl boronic acids, which are in equilibrium with the anhydride form and water (Table 1B, entry 10).

TABLE 1

The Enolate Chan-Evans-Lam Reaction: Effect of Aryl Boron and Reaction Parameters$^a$ A. Effect of Boron Group

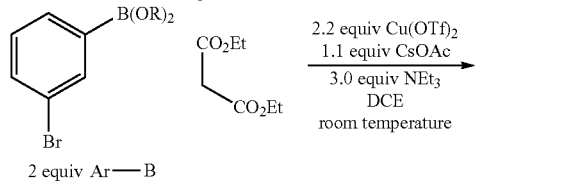

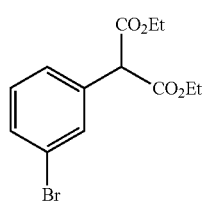 [SMILES: CCOC(=O)C(C(=O)OCC)c1cccc(Br)c1]

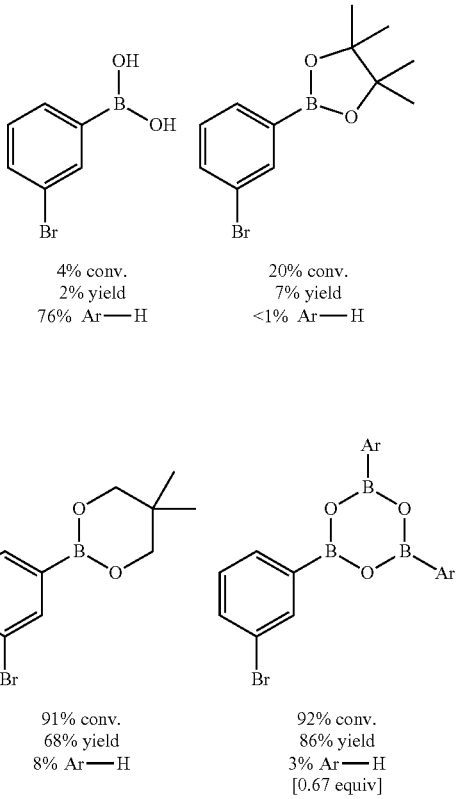

| | | |
|---|---|---|
| 4% conv. | | 20% conv. |
| 2% yield | | 7% yield |
| 76% Ar—H | | <1% Ar—H |

| | | |
|---|---|---|
| 91% conv. | | 92% conv. |
| 68% yield | | 86% yield |
| 8% Ar—H | | 3% Ar—H |
| | | [0.67 equiv] |

B. Effect of Cu-Source and Reaction Parameters

| entry | deviation from above | conv. (%) | yield (%) | Ar—H (%) |
|---|---|---|---|---|
| 1 | none | 92 | 86 | 3 |
| 2 | Cu(OAc)$_2$ instead of Cu(OTf)$_2$ | 30 | 11 | 61 |
| 3 | Cu(OMe)$_2$ instead of Cu(OTf)$_2$ | 15 | 13 | 84 |
| 4 | CuSO$_4$ instead of Cu(OTf)$_2$ | 5 | 0 | 30 |
| 5 | pyridine instead of NEt$_3$ | 3 | 0 | 92 |
| 6 | K$_2$CO$_3$ instead of NEt$_3$ | 5 | 0 | 104 |
| 7 | no NEt$_3$ | 0 | 0 | 104 |
| 8 | NaOAc instead et CsOAc | 86 | 78 | 6 |
| 9 | no CsOAc | 71 | 48 | 2 |
| 10 | 6 equiv of H$_2$O | 17 | 15 | 43 |

$^a$Conversions (based on malonate) and yields determined by calibrated GC using dodecane as the internal standard, 0.2M 48 h. Ar = 4-C$_6$H$_4$Br The scope of the Cu-mediated oxidative coupling of aryl boroxines and malonate esters is demonstrated in Table 2. Aryl fluorides, chlorides, bromides, and highly reactive iodides (1c) were tolerated under the standard reaction conditions. In traditionally employed malonate arylation methods, such as SNAr or cross-coupling, these functional groups are typically reactive. The reaction can be conducted open to air on the gram scale without decrease in efficiency (1a' 74% yield, 1.4 grams of product).

TABLE 2

Scope of the Cu-Mediated Oxidative Arylation of Malonate Esters with Aryl Boroxines.

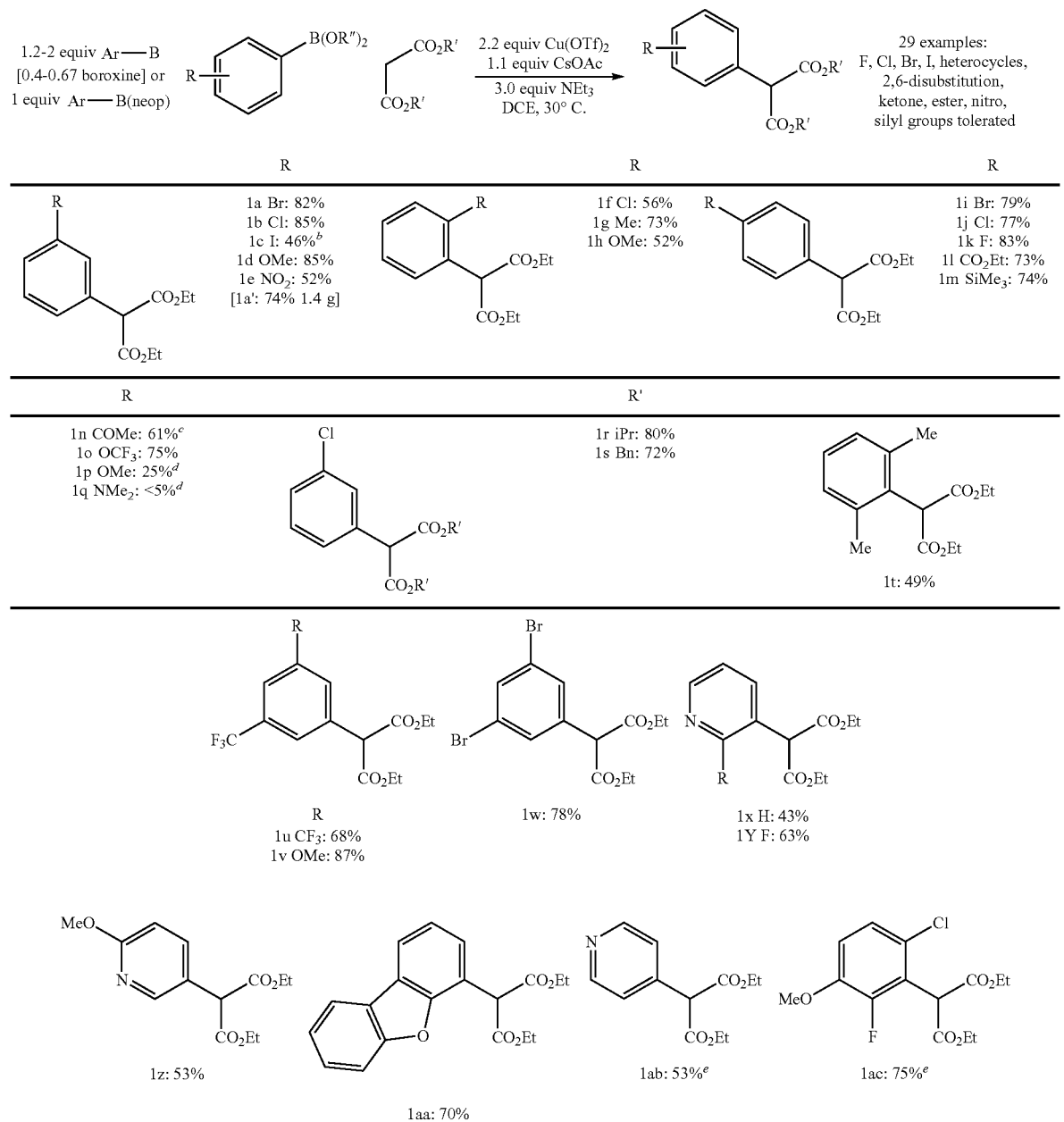

$^a$0.20M in DCE, 19-48 hours, see SI for details. Unless noted, yields are isolated material using 2.0 equiv of Ar—B reagent (0.67 equiv boroxine). 0.5 mmol scale
$^b$1.2 equiv of Ar—B at rt.
$^c$1.2 equiv of Ar—B at 30° C.
$^d$Yield by calibrated $^1$H NMR, >95% conv of malonate.
$^e$1 equiv Ar—B(neop), 2 equiv malonate at 35° C.

Substitution at the 2- or 3-position with electron-withdrawing nitro or chloro groups (1b, 1e, 1f) or donating methyl or methoxy groups (1d, 1g, 1h) led to moderate to excellent yields of product. The reaction tolerated aryl boroxines with potentially reactive ester (1l), ketone (1n), and silyl functionality (1m), as well as CF$_3$ (1u, 1v) and OCF$_3$ (1o) substitution. For electron-rich, 4-substituted aryl boroxines, low yields were observed as the arylated malonate products undergo further oxidative coupling reactions with malonate (1p, 1q). These electron-rich arene derivatives however can be readily accessed from bromo-containing products 1a and 1i in >60% overall yield by a sequential oxidative coupling/Pd-catalyzed cross-coupling protocol. 16c Iso-propyl or benzyl malonate esters (1r, 1s), polysubstituted aryl boroxines (1u, 1v, 1w), and bulky 2,6-disubstituted (1t) reagents could be employed under the standard reaction conditions to give consistently high yields of product. Heterocycles such as substituted pyridines (1x, 1y, 1z), and dibenzofuran (1aa) could also be oxidatively coupled to malonate derivatives. The tolerance of the reaction was accessed further by conducting an intermolecular functional group tolerance screen as outlined by Glorius and co-workers (see Table 10).[17]

Under the standard reaction conditions two equivalents of the aryl boron reagent (0.67 equiv boroxine) were generally employed, which could be a drawback if the arylating reagent is particularly valuable. To address this issue, it was found that under modified conditions, aryl or heteroaryl neopentyl boronic esters could be used as the limiting reagent to afford good yields of the desired oxidative coupling product. Examples of successful aryl groups include bromide (1a 87%) and iodide containing substrates (1c 51%), a pyridine (1ab), and a polyfunctionalized trisubstituted aryl partner (1ac).

This oxidative coupling strategy also allowed for the generation of quaternary carbon centers by arylation or vinylation of tertiary sp³-nucleophiles under remarkably mild conditions (Table 3).[18,19] Preliminary experiments, with both aryl boroxines and alkenyl neopentyl boronic ester reagents, demonstrated the ability of malonates to undergo Cu-mediated CC bond formation under similar conditions to those described above.[20,21] The cross-coupling reaction tolerates benzylic substitution (2f) and a potentially reactive alkyl chloride group (2g). This type of reactivity to generate quaternary carbon centers with diester substrates is without precedent in Cu-promoted cross-coupling.[22]

TABLE 3

Cu-Mediated Oxidative Arylation and Vinylation of Tertiary sp³-Nucleophiles

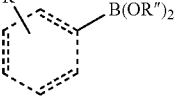

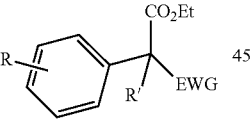

2a: 57%<sup>a</sup>

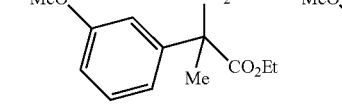

2b: 49%<sup>a</sup>

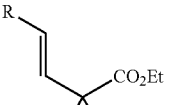

2c: 40%<sup>a</sup>

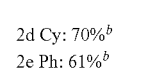

2d Cy: 70%<sup>b</sup>
2e Ph: 61%<sup>b</sup>

TABLE 3-continued

Cu-Mediated Oxidative Arylation and Vinylation of Tertiary sp³-Nucleophiles

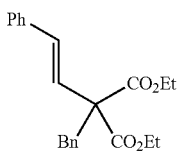

2f: 57%<sup>b</sup>

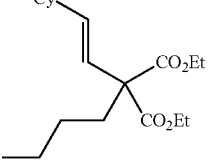

2g: 50%<sup>b</sup>

0.20M in DCE, 25-72 hours, see SI for details.
<sup>a</sup>Using 3 equiv Ar—B (1 equiv boroxine) at room temperature.
<sup>b</sup>Using 1 equiv Ar—B(neop), 2 equiv malonate at 35° C.

Cu-mediated oxidative coupling can be applied to activated methylene substrates that have not been reported to undergo Hurtley-type arylation under mild conditions (<70° C.),[9d] such as stabilized amides, sulfonyls, and phosphonyls (Table 4).[23,24] Both cyclic and acyclic alkyl 1,3-amido esters (3a-c) and aryl/alkyl 1,3-amido esters (3d) can be used as reaction partners, as well as 1,3-sulfonyl amides (4a-c). In both cases, halogenated and heterocyclic boroxines were smoothly arylated in high yield under mild conditions (rt-30° C.). 1,3-Phosphonyl esters (5a-c) and a sulfonyl ester (6a) undergo oxidative coupling with similar efficiency to 1,3-diesters. Of note, each of these classes of compounds, made accessible by this Cu-mediated oxidative arylation strategy, represents an important fragment in medicinal chemistry, such as in beta-lactam antibiotics, tyrosine phosphatase inhibitors, and histone deacetylase inhibitors.[25]

TABLE 4

Scope of the Cu-Mediated Oxidative Arylation with sp³-Nucleophiles.

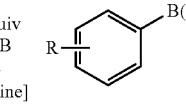

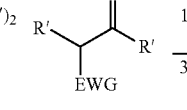

13 examples:
F, Cl, Br, heterocycles,
2-, 3- or 4-substitution tolerated
EWG: ester, alkyl/aryl amide, sulfonyl, phosphonyl ester Amido Esters

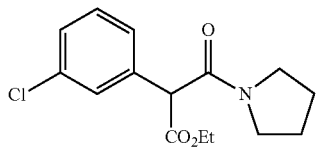

3a: 85%<sup>a</sup>

TABLE 4-continued

Scope of the Cu-Mediated Oxidative Arylation with sp³-Nucleophiles.

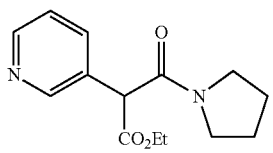

3b: 59%

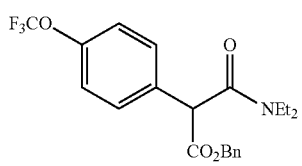

3c: 66%[a]

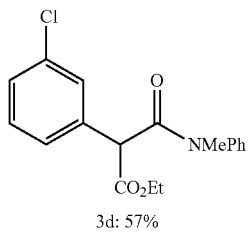

3d: 57%

Sulfonyl-Amides (NR₂ = pyrrolidine)

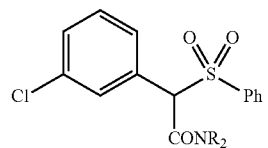

4a: 86%[a]

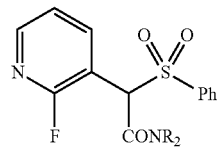

4b: 63%[a]

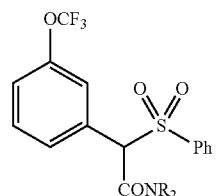

4c: 82%[a]

Phosphonyl-Esters

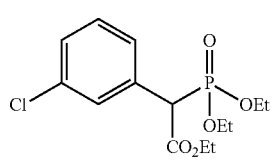 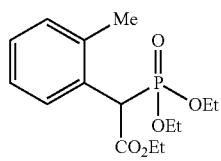

5a: 53%  5b: 59%

TABLE 4-continued

Scope of the Cu-Mediated Oxidative Arylation with sp³-Nucleophiles.

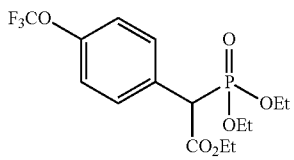

5c: 48%

Sulfonyl-Ester

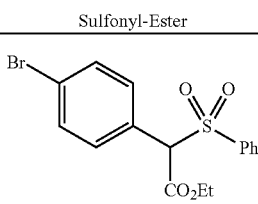

6a: 56%[b]

Tertiary sp³-Nucleophiles

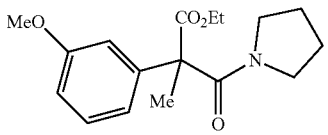

7a: 47%[c]

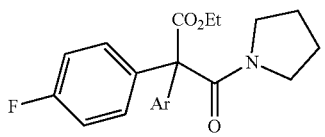

7b Ar: 3-ClC₆H₄ 50%[d]

0.20M in DCE, 2.5-72 hours, see Supporting information for details. Unless noted yields are of isolated material using 2 equiv of aryl boron reagent (0.67 equiv boroxine) at 30° C. 0.5 mmol scale
[a] 1.2 equiv of Ar—B at rt.
[b] 1.5 equiv Ar—B at 40° C.
[c] 3 equiv Ar—B at rt.
[d] 1.2 equiv Ar—B at 40° C.

Finally, without modification to the standard conditions, tertiary 1,3-amido esters can be arylated using our method in moderate yield (Table 4). The reaction proceeds on both alkyl (7a) and aryl (7b) substituted sp³-nucleophiles to deliver products which are not accessible via established Cu-mediated reactions of aryl electrophiles.

We have yet to obtain conclusive information regarding the mechanism of the transformation; however our current hypothesis is that the steps mirror that of the CEL reactions as outlined by Stahl and coworkers.[7] Future work will aim to cast light on this issue.

In summary, we have reported a powerful new strategy for the arylation of activated sp³-nucleophiles via Cu-mediated oxidative coupling. This enolate Chan-Evans-Lam reaction allows for installation of sensitive and densely functionalized aryl units under mild reaction conditions from readily available aryl boron species. Given the broad scope of reactivity, ability to form quaternary centers, and tolerance of electrophilic groups, this methodology should find broad appeal as an alternative to traditional cross-coupling or $S_NAr$ reactions of aryl electrophiles with activated methylene species.

Unless noted, all reactions were conducted under inert atmosphere employing standard schlenk technique or by the use of an N$_2$-filled glovebox. All glassware was oven-dried prior to use. Flash chromatography was performed as described by Still and co-workers[S1] (SiliaFlash P60, 40-63 μm, 60 A silica gel, Silicycle) or by automated flash chromatography (Isolera, HP-SIL or KP-SIL SNAP silica cartridges, Biotage). Analytical thin-layer chromatography was performed using glass plates pre-coated with silica (SiliaPlate G TLC—Glass-Backed, 250 μm, Silicycle). TLC plates were visualized by UV light and/or staining with aqueous basic potassium permanganate. Unless otherwise noted, all reagents were obtained from commercial vendors and used as supplied. Neopentyl boronic esters leading to 6a, 6b and 6d were prepared according to the literature procedure from the corresponding boronic acid.[S2] The neopentyl boronic ester leading to 6c was synthesized according to the literature procedure.[S3]

Arylboroxines were formed from the corresponding arylboronic acid via azeotropic removal of water using a Dean-Stark apparatus. To a 100 mL round bottom flask was added arylboronic acid (2.00 g) and toluene (40 mL). Water was removed azeotropically under N$_2$ from the solution during a 3 h period, removing the collected water/toluene approximately every hour. The mixture was cooled to room temperature and filtered if any precipitates were present. Hexane (100 mL) was added to precipitate the boroxine, and the solvent was removed by vacuum. Quantitative recovery of boroxine could be achieved with this method.

II. Selected Additional Optimization Data

II A. Optimal Conditions Employing Cu(OAc)$_2$

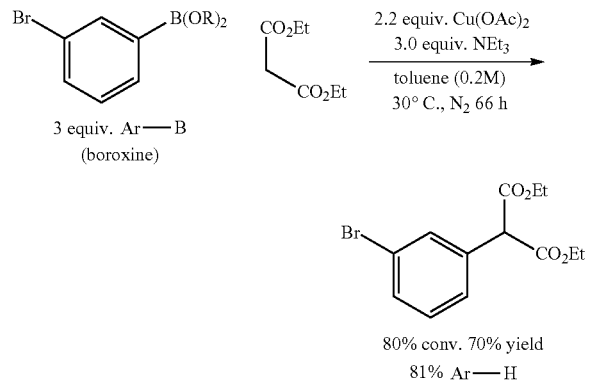

II B. Table 5 Shows Conditions Using Catalytic Copper Salts and O$_2$.

TABLE 5

Conditions Using Catalytic Copper Salts and O$_2$

| entry | | conv. (%) | yield (%) | Ar—H (%) |
|---|---|---|---|---|
| 1 | Cu(OTf)$_2$ | 17 | 8 | 20 |
| 2 | Cu(OTf)$_2$, no CsOAc | 40 | 3 | 23 |
| 3 | Cu(OAc)$_2$ | 4 | 0 | 8 |
| 4 | Cu(OAc)$_2$, no CsOAc | 23 | 7 | 16 |

II C. Conditions Similar to Those Reported for Oxidative Aldehyde α-Vinylation[S4]

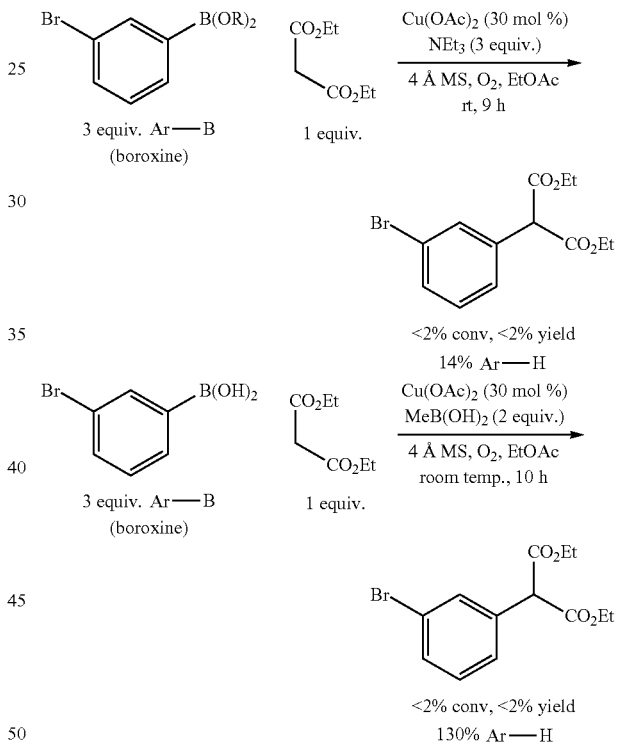

II D. Table 6 Shows the Effect of Arylboron Reagent Stoichiometry with Cu(OAc)$_2$

TABLE 6

Effect of Arylboron Reagent Stoichiometry with Cu(OAc)$_2$

TABLE 6-continued

Effect of Arylboron Reagent Stoichiometry with Cu(OAc)$_2$

| entry | Deviation | conv. (%) | yield (%) | Ar—H (%) |
|---|---|---|---|---|
| 1 | none | 75 | 65 | 114 |
| 2 | 1 equiv. Ar—B | 32 | 24 | 41 |
| 3 | 2 equiv. Ar—B | 54 | 46 | 72 |
| 4 | 4 equiv. Ar—B | 82 | 62 | 143 |

Yields and conversions (malonate) determined by calibrated GC using dodecane as internal standard.

II E. Table 7 Shows the Effect of Base with Cu(OAc)$_2$

TABLE 7

Effect of Base with Cu(OAc)$_2$

| entry | base | conv. (%) | yield (%) | Ar—H (%) |
|---|---|---|---|---|
| 1 | Et$_3$N | 80 | 73 | 117 |
| 2 | DIPEA | 55 | 14 | 138 |
| 3 | Me$_2$NEt | 33 | 24 | 58 |
| 4 | Et2NH | 35 | 33 | 123 |
| 5 | TMEDA | 36 | 11 | 102 |
| 6 | pyridine | 48 | 45 | 88 |
| 7 | 2,6-Lutidine | 37 | 29 | 83 |
| 8 | Cs$_2$CO$_3$ | 20 | 9 | 133 |

Yields and conversions (malonate) determined by calibrated GC using dodecane as internal standard.

II F. Table 8 Shows the Effect of Solvent with Cu(OAc)$_2$

TABLE 8

Effect of Solvent with Cu(OAc)$_2$

TABLE 8-continued

Effect of Solvent with Cu(OAc)$_2$

| entry | Solvent | conv. (%) | yield (%) | Ar—H (%) |
|---|---|---|---|---|
| 1 | Toluene | 62 | 53 | 90 |
| 2 | PhCF$_3$ | 53 | 50 | 83 |
| 3 | 1,2-DCE | 43 | 37 | 73 |
| 4 | THF | 45 | 39 | 77 |
| 5 | MeCN | <15 | 11 | 26 |
| 6 | DMA | <15 | 14 | 48 |

Yields and conversions (malonate) determined by calibrated GC using dodecane as internal standard.

II G. Table 9 Shows the Effect of Cu-Source Under Optimized Conditions.

TABLE 9

Effect of Cu-Source under Optimized Conditions.

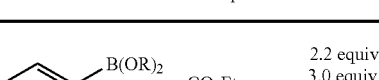

| entry | base | conv. (%) | yield (%) | Ar—H (%) |
|---|---|---|---|---|
| 1 | Cu(OTf)$_2$ | 92 | 86 | 3 |
| 2 | Cu(OAc)$_2$ | 30 | 11 | 61 |
| 3 | Cu(OMe)$_2$ | 15 | 13 | 84 |
| 4 | CuSO$_4$ | 5 | 0 | 30 |
| 5 | CuF$_2$ | 6 | 0 | 39 |
| 6 | CuO | 6 | 0 | 3 |
| 7 | CuCl$_2$ | 25 | 0 | 30 |
| 8 | Cu(2-ethylhexanoate)$_2$ | 9 | 5 | 98 |
| 9 | Cu(TMHD)$_2$ | 14 | 0 | 84 |

Yields and conversions (malonate) determined by calibrated GC using dodecane as internal standard. TMHD: 2,2,6,6-tetramethyl-3,5-heptanedionate

TABLE 10

Functional Group Robustness Screen 3 equiv. Ar—B (boroxine) + CO₂Et-CH₂-CO₂Et (1 equiv.) → (3-bromophenyl)(CO₂Et)₂CH, with 2.2 equiv. Cu(OTf)₂, 1.1 equiv. CsOAc, 3.0 equiv. NEt₃, DCE, 30° C., 48 h

| entry | Additive | yield of 1a (%) | Additive remaining (%) | Malonate remaining (%) |
|---|---|---|---|---|
| 1 | none | 93 ✓ | n.d. | <5 |
| 2 | iodobenzene | 78 ✓ | 83 ✓ | 12 |
| 3 | benzophenone (Ph-CO-Ph) | 69 ✓ | >95 ✓ | 30 |
| 4 | methyl crotonate (CH₃CH=CHCO₂Me) | >95 ✓ | >95 ✓ | <5 |
| 5 | benzoic acid (Ph-CO₂H) | 35 ✗ | 77 ✓ | 66 |
| 6 | Cl-(CH₂)₈-CH₃ | >95 ✓ | >95 ✓ | <5 |
| 7 | Br-(CH₂)₄-CH₃ | >95 ✓ | 84 ✓ | <5 |
| 8 | morpholine | 90 ✓ | 87 ✓ | 6 |
| 9 | acetanilide (PhNHC(O)CH₃) | 43 – | 18 ✗ | 65 |
| 10 | HO-(CH₂)₆-CH₃ | 76 ✓ | n.d. | n.d. |
| 11 | acetophenone (Ph-CO-Me) | 93 ✓ | 80 ✓ | <5 |
| 12 | Ph-Bpin | 84 ✓ | >95 ✓ | 11 |
| 13 | aniline (Ph-NH₂) | 18 ✗ | 46 – | 79 |
| 14 | indole | 18 ✗ | 21 ✗ | 79 |

TABLE 10-continued

Functional Group Robustness Screen

| 15 | phenol (Ph-OH) | 20 × | 91 ✓ | 78 |
| --- | --- | --- | --- | --- |
| 16 | pyridine | 93 ✓ | n.d. | 7 |
| 17 | styrene | 90 ✓ | >95 ✓ | 7 |
| 18 | phenylacetylene | 26 × | 21 × | 69 |
| 19 | Ph—≡—Ph | 86 ✓ | 76 ✓ | 10 |
| 20 | L-proline | 70 ✓ | n.d. | 31 |
| 21 | 2-methoxybenzonitrile | 90 ✓ | 91 ✓ | <5 |
| 22 | benzyl cyanide | 89 ✓ | >95 ✓ | <5 |

Reactions performed on 0.10 mmol scale according to the general procedure (glovebox), with an additional 1.0 equiv of additive.
Yields determined by calibrated GC using dodecane as internal standard.
0.2M 48% General assessment of product yield and additive recovery based on:
100-78% (good ✓),
74-40% (mediocre −),
40-0% (poor ×),
n.d. not determined IV. Synthesis of Substrates

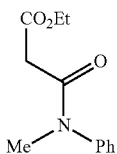

Synthesized according to an adapted literature procedure[S5] using (phenylsulfonyl)acetic acid (1.2 g, 6.0 mmol) and pyrrolidine (0.50 mL, 6.0 mmol). Purified by silica gel chromatography (1:1 Hex/EtOAc to 100% EtOAc) to afford the title compound as a colorless solid (1.26 g, 83%). Spectroscopic data agreed with that reported.[S6]

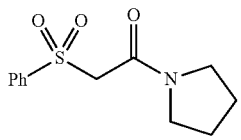 [SMILES: O=C(CS(=O)(=O)c1ccccc1)N1CCCC1]

Synthesized according to an adapted literature procedure[S7] using N-methylaniline (925 mg, 7.0 mmol), mono-ethyl malonate (0.83 mL, 7.0 mmol), and DCC (2.17 g, 10.5 mmol). Purification by silica gel chromatography (1:1 Hexanes/EtOAc) afforded the title compound as a yellow oil (1.14 g, 73%). Spectroscopic data agreed with that reported.[S7]

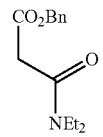

Synthesized according to an adapted literature procedure[S7] using N,N-diethylamine (1.42 mL, 14.0 mmol), mono-benzyl malonate (1.36 g, 7.0 mmol), and DCC (2.17 g, 10.5 mmol). Purification by silica gel chromatography (1:1 Hexanes/EtOAc to 100% EtOAc) afforded the title compound as a colorless oil (1.01 g, 58%).

$^1$H NMR (CDCl$_3$, 400 MHz) δ 7.34-7.27 (m, 5H), 5.16 (s, 2H), 3.44 (s, 2H), 3.36 (q, J=7.1 Hz, 2H), 3.23 (q, J=7.1 Hz, 2H), 1.12 (t, J=7.2 Hz, 3H), 1.09 (t, J=7.2 Hz, 3H);

$^{13}$C NMR (CDCl$_3$, 125 MHz) δ 167.8, 165.1, 135.7, 128.7, 128.48, 128.47, 67.2, 42.8, 41.4, 40.4, 14.3, 12.9;

HRMS (LCMS ESI): calcd for C$_{14}$H$_{20}$NO$_3$ [M+H]$^+$: 250.1438. Found 250.1434.

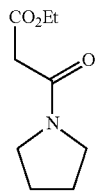

Synthesized according to an adapted literature procedure$^{S7}$ using pyrrolidine (0.58 mL, 7.0 mmol), mono-ethyl malonate (0.83 mL, 7.0 mmol), and DCC (2.17 g, 10.5 mmol). Purification by silica gel chromatography (100% EtOAc) afforded the title compound as a yellow oil (1.09 g, 84%).

$^1$H NMR (CDCl$_3$, 400 MHz) δ 4.19 (q, J=7.2 Hz, 2H), 3.49 (t, J=7.0 Hz, 2H), 3.44 (t, J=7.0 Hz, 2H), 3.38 (s, 2H), 2.00-1.84 (m, 4H), 1.28 (t, J=7.1 Hz, 3H);

$^{13}$C NMR (CDCl$_3$, 125 MHz) δ 167.7, 164.5, 61.5, 47.3, 46.1, 42.6, 26.2, 24.6, 14.3;

HRMS (LCMS ESI): calcd for C$_9$H$_{16}$NO$_3$ [M+H]$^+$: 186.1125. Found 186.1123.

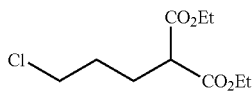

Synthesized according to the literature procedure$^{S8}$ using diethyl malonate (1.53 mL, 10 mmol). Purified by silica gel chromatography (20:1 toluene/Et2O) to afford the title compound as a colorless oil (1.19 g, 50%). Spectroscopic data agreed with that reported.$^{S9}$

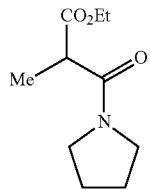

Synthesized according to an adapted literature procedure$^{S10}$ using the corresponding amido ester (0.56 g, 3.0 mmol). Purification by silica gel chromatography (1:1 Hexanes/EtOAc to 100% EtOAc) afforded the title compound as a yellow oil (302 mg, 50%).

$^1$H NMR (CDCl$_3$, 400 MHz) δ 4.20-4.12 (m, 2H), 3.56-3.40 (m, 5H), 1.97-1.84 (m, 4H), 1.38 (d, J=7.0 Hz, 3H), 1.24 (t, J=7.0 Hz, 3H);

$^{13}$C NMR (CDCl$_3$, 125 MHz) δ 170.9, 168.1, 61.3, 46.9, 46.2, 45.2, 26.2, 24.4, 14.2, 13.7;

HRMS (LCMS ESI): calcd for C$_{10}$H$_{18}$NO$_3$ [M+H]$^+$: 200.1281. Found 200.1280.

V. Oxidative Coupling of Sp3-Nucleophiles with Arylboron Reagents

General Procedure A: Using Arylboroxines (Glovebox)

In an atmosphere controlled glovebox, Cu(OTf)$_2$ (398 mg, 1.10 mmol, 2.20 equiv.), arylboroxine (0.330 mmol, 0.670 equiv.), and CsOAc (106 mg, 0.550 mmol, 1.10 equiv.) were added sequentially to a 2 dram vial charged with a stir bar. The sp$^3$-carbon nucleophile (0.500 mmol, 1.00 equiv.) and triethylamine (0.210 mL, 1.50 mmol, 3.00 equiv.) were added as a solution in anhydrous 1,2-DCE (1.20 mL). Additional 1,2-DCE (2×0.5 mL) was used to quantitatively transfer the solution to the reaction mixture. The vial was sealed with a PTFE-lined cap and stirred outside the glovebox at 30° C. Reaction progress was generally monitored by GC-FID using n-dodecane as an internal standard. Unless otherwise noted, reactions were quenched after 36-48 hours, when >95% conversion of sp$^3$-carbon nucleophile was reached. The reaction was quenched with 5 mL of brine and extracted with EtOAc (4×10 mL). The organic layer was then washed with 5 mL brine and dried with Na$_2$SO$_4$, and the solvent was removed by vacuum. The crude residue was purified by flash silica gel chromatography. Note: the order of addition of reagents is important for achieving optimal yields.

No Glovebox, Open to Air Procedure

In air, Cu(OTf)$_2$ (398 mg, 1.10 mmol, 2.20 equiv.), arylboroxine (0.330 mmol, 0.670 equiv.), and CsOAc (106 mg, 0.550 mmol, 1.10 equiv.) were sequentially added to a 2 dram vial charged with a stirbar. To a separate 1 dram vial was added sp$^3$-carbon nucleophile (0.500 mmol, 1.00 equiv.), triethylamine (0.210 mL, 1.50 mmol, 3.00 equiv.) and dry 1,2-DCE (1.2 mL). This solution was transferred to the reaction vial, using additional 1,2-DCE (2×0.5 mL) for a quantitative transfer. The vial was sealed under air and stirred at 30° C. The rest of the procedure was followed as described above. 84% conversion, 84% yield as determined by calibrated GC-FID using dedecane as internal standard.

General Procedure B Using Neopentylboronic Esters

In an atmosphere controlled glovebox, Cu(OTf)$_2$ (2.20 equiv.), neopentyl boronic ester (1.00 equiv.) if a solid, and CsOAc (1.10 equiv.) were sequentially added to a 2 dram vial charged with a stir bar. The sp$^3$-carbon nucleophile (2.00 equiv.), neopentyl boronic ester (1.00 equiv.) if a liquid, and triethylamine (3.00 equiv.) were added as a solution in dry 1,2-DCE (1.2 mL). Additional 1,2-DCE (2×0.5 mL) was used to quantitatively transfer the solution to the reaction mixture. The vial was sealed with a PTFE-lined cap and stirred outside the glovebox at 35° C. The reaction was quenched with ~5 mL of brine and extracted with EtOAc (4×10 mL). The organic layer was then washed with 5 mL brine and dried with Na$_2$SO$_4$, and the solvent was removed in vacuo. The crude residue was purified by flash silica gel chromatography.

Gram Scale Reaction in Air, Table 2, Entry 1a'.

To a 4 dram vial open to air was added diethyl malonate (0.961 g, 6.00 mmol, 1.00 equiv.), triethylamine (2.51 mL, 18.0 mmol, 3.00 equiv.), and dry 1,2-DCE (14.0 mL). To a 100 mL round bottom flask was added Cu(OTf)$_2$ (4.77 g, 13.2 mmol, 2.20 equiv.), arylboroxine (2.19 g, 12.0 mmol, 2.00 equiv.), and CsOAc (1.27 g, 6.6 equiv., 1.10 equiv.). The malonate solution was quantitatively transferred to the flask using additional 1,2-DCE rinses (2×6 mL). The reaction mixture was sealed under air with a rubber septa and stirred at 30° C. for 44 h. Isolated in 74% yield (1.40 g) after purification by column chromatography (10:1 to 15:1 Hex/EtOAc) as a colorless oil. Note: CsOAc is hydroscopic and care should be taken to ensure the reagent is anhydrous prior to use.

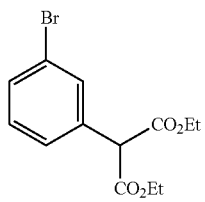 [SMILES: CCOC(=O)C(C(=O)OCC)c1cccc(Br)c1]

Table 2, entry 1a Prepared according to the General Procedure A from the corresponding arylboroxine (183 mg, 0.330 mmol, 2.00 equiv. Ar—B) and diethyl malonate (80 mg, 0.50 mmol, 1.0 equiv.), 37 h. Isolated in 82% yield after purification by column chromatography (10:1 Hex/EtOAc) as a colorless oil.

Prepared according to the General Procedure B from the corresponding neopentyl boronic ester (135 mg, 0.500 mmol, 1.00 equiv.) and diethylmalonate (160 mg, 1.00 mmol, 2.00 equiv.), stirred at 35° C., 48 h. Calibrated GC yield of 87% obtained using dodecane as internal standard.

$^1$H NMR (CDCl$_3$, 500 MHz) δ 7.57 (m, 1H), 7.47 (m, 1H), 7.35 (m, 1H), 7.24 (m, 1H), 4.56 (s, 1H), 4.26-4.19 (m, 4H), 1.28-1.26 (t, J=7.0 Hz, 6H);

$^{13}$C NMR (CDCl$_3$, 125 MHz) δ 167.7, 135.0, 132.5, 131.5, 130.2, 128.1, 122.6, 62.2, 57.6, 14.1;

HRMS (LCMS ESI): calcd for C$_{13}$H$_{16}$BrO$_4$ [M+H]$^+$: 315.0226. Found 315.0233.

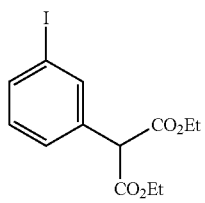 [SMILES: CCOC(=O)C(C(=O)OCC)c1cccc(I)c1]

Table 2, Entry 1c

Prepared according to the General Procedure A from the corresponding arylboroxine (138 mg, 0.200 mmol, 1.2 equiv. Ar—B) and diethyl malonate (80 mg, 0.50 mmol, 1.0 equiv.), stirred at room temperature, 19 h. Isolated in 46% yield after purification by column chromatography (20:1 to 10:1 Hex/EtOAc) as a colorless oil.

Prepared according to the General Procedure B from the corresponding neopentyl boronic ester (79 mg, 0.25 mmol, 1.0 equiv.) and diethyl malonate (80 mg, 0.50 mmol, 2.0 equiv.), stirred at 30° C., 44 h. Isolated in 51% yield after purification by column chromatography (20:1 to 10:1 Hex/EtOAc) as a colorless oil.

$^1$H NMR (CDCl$_3$, 500 MHz) δ 7.75 (m, 1H), 7.67 (m, 1H), 7.40 (m, 1H), 7.11 (m, 1H), 4.52 (s, 1H), 4.27-4.17 (m, 4H), 1.28-1.25 (t, J=7.5 Hz, 6H);

$^{13}$C NMR (CDCl$_3$, 125 MHz) δ 167.7, 138.3, 137.5, 135.0, 130.4, 128.7, 94.3, 62.2, 57.5, 14.1;

HRMS (LCMS ESI): calcd for C$_{13}$H$_{16}$IO$_4$ [M+H]$^+$: 363.0088. Found 363.0089.

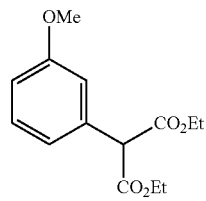 [SMILES: CCOC(=O)C(C(=O)OCC)c1cccc(OC)c1]

Table 2, entry 1d

Prepared according to the General Procedure A from the corresponding arylboroxine (134 mg, 0.330 mmol, 2.00 equiv. Ar—B) and diethyl malonate (80 mg, 0.50 mmol, 1.00 equiv.), 20 h. Isolated in 85% yield after purification by column chromatography (10:1 to 4:1 Hex/EtOAc) as a pale yellow oil. $^1$H and $^{13}$C NMR data agreed with literature data.[S11] HRMS matched the molecular formula.

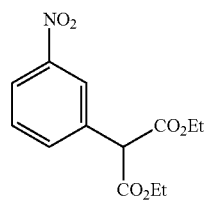 [SMILES: CCOC(=O)C(C(=O)OCC)c1cccc([N+](=O)[O-])c1]

Table 2, Entry 1e

Prepared according to the General Procedure A from the corresponding arylboroxine (149 mg, 0.33 mmol, 2.00 equiv. Ar—B) and diethyl malonate (80 mg, 0.50 mmol, 1.00 equiv.), 48 h. Isolated in 52% yield after purification by column chromatography (4:1 Hexane/CH2Cl2 to 100% CH$_2$Cl$_2$) as a pale yellow oil. $^1$H and $^{13}$C NMR data agreed with literature data.[S12] HRMS matched the molecular formula

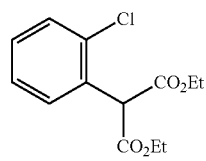 [SMILES: CCOC(=O)C(C(=O)OCC)c1ccccc1Cl]

Table 2, Entry 1f

Prepared according to the General Procedure A from the corresponding arylboroxine (156 mg, 0.330 mmol, 2.00 equiv. Ar—B) and diethyl malonate (80 mg, 0.50 mmol, 1.0 equiv.), 42 h. Isolated in 56% yield after purification by column chromatography (10:1 to 1:1 Hex/EtOAc) as a colorless oil. $^1$H and $^{13}$C NMR data agreed with literature data.[S13] HRMS matched the molecular formula.

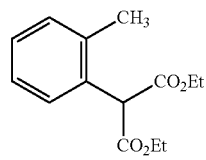 [SMILES: CCOC(=O)C(C(=O)OCC)c1ccccc1C]

Table 2, Entry 1g

Prepared according to the General Procedure A from the corresponding arylboroxine (118 mg, 0.330 mmol, 2.00 equiv. Ar—B) and diethyl malonate (80 mg, 0.50 mmol, 1.0 equiv.), 48 h. Isolated in 73% yield after purification by column chromatography (10:1 to 4:1 Hex/EtOAc) as a pale yellow oil. $^1$H and $^{13}$C NMR data agreed with literature data.[S11] HRMS matched the molecular formula.

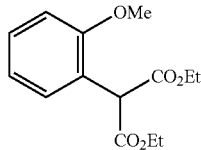 [SMILES: CCOC(=O)C(C(=O)OCC)c1ccccc1OC]

Table 2, Entry 1h

Prepared according to the General Procedure A from the corresponding arylboroxine (134 mg, 0.330 mmol, 2 equiv. Ar—B) and diethyl malonate (80 mg, 0.50 mmol, 1.0 equiv.), 48 h. Isolated in 52% yield after purification by column chromatography (10:1 to 1:1 Hex/EtOAc) as a colorless oil. $^1$H and $^{13}$C NMR data agreed with literature data.[S11] HRMS matched the molecular formula.

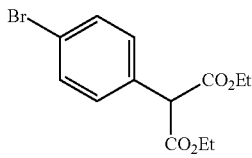 [SMILES: CCOC(=O)C(C(=O)OCC)c1ccc(Br)cc1]

Table 2, Entry 1i

Prepared according to the General Procedure A from the corresponding arylboroxine (183 mg, 0.330 mmol, 2.0 equiv. Ar—B) and diethyl malonate (80 mg, 0.50 mmol, 1.0 equiv.), 33 h. Isolated in 79% yield after purification by column chromatography (10:1 to 4:1 Hex/EtOAc) as a colorless oil.

$^1$H NMR (CDCl$_3$, 500 MHz) δ 7.50-7.48 (m, 2H), 7.30-7.28 (m, 2H), 4.56 (s, 1H), 4.25-4.17 (m, 4H), 1.26 (t, J=7.5, 6H)

$^{13}$C NMR (CDCl$_3$, 125 MHz) δ 167.8, 131.93, 131.89, 131.1, 122.6, 62.1, 57.5, 14.2;

HRMS (LCMS ESI): calcd for C$_{13}$H$_{16}$BrO$_4$ [M+H]$^+$: 315.0226. Found 315.0227.

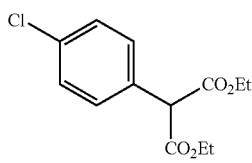 [SMILES: CCOC(=O)C(C(=O)OCC)c1ccc(Cl)cc1]

Table 2, Entry 1j

Prepared according to the General Procedure A from the corresponding arylboroxine (138 mg, 0.330 mmol, 2 equiv. Ar—B) and diethyl malonate (80 mg, 0.50 mmol, 1.0 equiv.), 48 h. Isolated in 77% yield after purification by column chromatography (10:1 Hex/EtOAc) as a colorless oil. $^1$H and $^{13}$C NMR data agreed with literature data.[S12] HRMS matched the molecular formula.

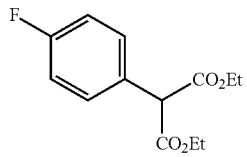

Table 2, Entry 1k

Prepared according to the General Procedure A from the corresponding arylboroxine (122 mg, 0.330 mmol, 2 equiv. Ar—B) and diethyl malonate (80 mg, 0.50 mmol, 1.0 equiv.), 44 h. Isolated in 83% yield after purification by column chromatography (10:1 to 4:1 Hex/EtOAc) as a colorless oil. $^1$H and $^{13}$C NMR data agreed with literature data.[S11] HRMS matched the molecular formula.

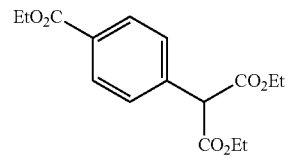 [SMILES: CCOC(=O)c1ccc(C(C(=O)OCC)C(=O)OCC)cc1]

Table 2, Entry 1l

Prepared according to the General Procedure A from the corresponding arylboroxine (176 mg, 0.330 mmol, 2.00 equiv. Ar—B) and diethyl malonate (80 mg, 0.50 mmol, 1.0 equiv.), 31 h. Isolated in 73% yield after purification by column chromatography (10:1 to 4:1 Hex/EtOAc) as a colorless oil.

$^1$H NMR (CDCl$_3$, 500 MHz) δ 8.05-8.03 (m, 2H), 7.49-7.47 (m, 2H), 4.66 (s, 1H), 4.38 (q, J=7.5 Hz, 2H), 4.27-4.17 (m, 4H), 1.39 (t, J=1.39 Hz, 3H), 1.26 (t, J=7.26 Hz, 6H);

$^{13}$C NMR (CDCl$_3$, 125 MHz) δ 167.7, 166.4, 137.7, 130.5, 129.9, 129.5, 62.2, 61.2, 58.1, 14.5, 14.1

HRMS (LCMS ESI): calcd for C$_{16}$H$_{21}$O$_6$[M+H]$^+$: 309.1333. Found 309.1334.

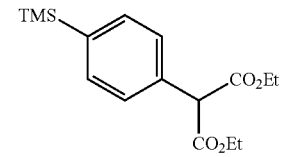 [SMILES: CCOC(=O)C(C(=O)OCC)c1ccc([Si](C)(C)C)cc1]

Table 2, Entry 1m

Prepared according to the General Procedure A from the corresponding arylboroxine (176 mg, 0.330 mmol, 2.00 equiv. Ar—B) and diethyl malonate (80 mg, 0.50 mmol, 1.0 equiv.), 48 h. Isolated in 74% yield after purification by column chromatography (10:1 to 4:1 Hex/EtOAc) as a colorless oil.

$^1$H NMR (CDCl$_3$, 500 MHz) δ 7.52-7.51 (m, 2H), 7.39-7.37 (m, 2H), 4.60 (s, 1H), 4.26-4.16 (m, 4H), 1.27 (t, J=7.2 Hz, 6H), 0.26 (s, 9H);

$^{13}$C NMR (CDCl$_3$, 125 MHz) δ 168.3, 140.6, 133.8, 133.3, 128.7, 61.9, 58.1, 14.2, -1.03;

HRMS (LCMS ESI): calcd for C$_{16}$H$_{25}$O$_4$Si [M+H]$^+$: 309.1517. Found 309.1519.

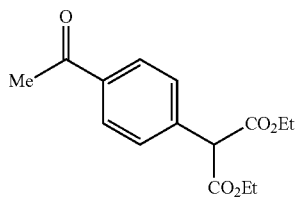 [SMILES: CCOC(=O)C(C(=O)OCC)c1ccc(C(C)=O)cc1]

Table 2, Entry 1n

Prepared according to the General Procedure A from the corresponding arylboroxine (90 mg, 0.20 mmol, 1.2 equiv. Ar—B) and diethyl malonate (80 mg, 0.50 mmol, 1.0 equiv.), 48 h. Isolated in 61% yield after purification by column chromatography (4:1 to 1:1 Hex/EtOAc) as a colorless oil. $^1$H and $^{13}$C NMR data agreed with literature data.[S12] HRMS matched the molecular formula.

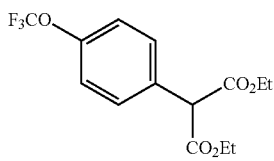 [SMILES: CCOC(=O)C(C(=O)OCC)c1ccc(OC(F)(F)F)cc1]

Table 2, Entry 1o

Prepared according to the General Procedure A from the corresponding arylboroxine (188 mg, 0.330 mmol, 2.0 equiv. Ar—B) and diethyl malonate (80 mg, 0.50 mmol, 1.0 equiv.), 26 h. Isolated in 75% yield after purification by column chromatography (10:1 to 4:1 Hex/EtOAc) as a colorless oil.

$^1$H NMR (CDCl$_3$, 500 MHz) δ 7.46-7.44 (m, 2H), 7.22-7.20 (m, 2H), 4.62 (s, 1H), 4.26-4.18 (m, 4H), 1.27 (t, J=7.4 Hz, 6H);

$^{13}$C NMR (CDCl$_3$, 125 MHz) δ 167.9, 149.3, 131.6, 131.0, 121.1, 120.6 (q, J=256 Hz), 62.2, 57.4, 14.1;

$^{19}$F NMR (CDCl$_3$, 469 MHz) δ −57.8

HRMS (LCMS ESI): calcd for C$_{14}$H$_{16}$F$_3$O$_5$ [M+H]$^+$: 321.0944. Found 321.0944.

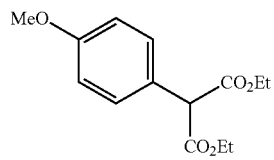 [SMILES: CCOC(=O)C(C(=O)OCC)c1ccc(OC)cc1]

Table 2, Entry 1p

Prepared according to the General Procedure A from the corresponding arylboroxine (134 mg, 0.33 mmol, 2.00 equiv. Ar—B) and diethyl malonate (80 mg, 0.5 mmol, 1.0 equiv.), 16 h. >95% conversion of malonate, 25% desired product as determined by $^1$H NMR analysis of the crude reaction mixture using dibenzyl ether as internal standard.

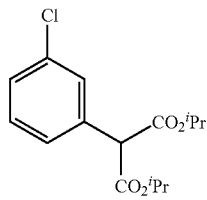

Table 2, Entry 1r

Prepared according to the General Procedure A from the corresponding arylboroxine (138 mg, 0.330 mmol, 2.0 equiv. Ar—B) and diisopropyl malonate (94 mg, 0.50 mmol, 1.0 equiv.), 48 h. Isolated in 80% yield after purification by column chromatography (10:1 to 4:1 Hex/EtOAc) as a pale yellow oil.

$^1$H NMR (CDCl$_3$, 500 MHz) δ 7.41 (m, 1H), 7.31-7.29 (m, 3H), 5.07 (m, 2H), 4.50 (s, 1H), 1.27 (d, J=6.7 Hz, 6H), 1.24 (d, J=6.7 Hz, 6H);

$^{13}$C NMR (CDCl$_3$, 125 MHz) δ 167.3, 134.9, 134.4, 129.8, 129.7, 128.5, 127.7, 69.8, 58.1, 21.8;

HRMS (LCMS ESI): calcd for C$_{15}$H$_{20}$ClO$_4$ [M+H]$^+$: 299.1045. Found 299.1044.

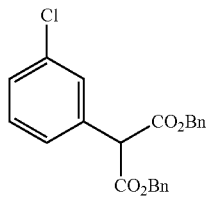 [SMILES: O=C(OCc1ccccc1)C(C(=O)OCc1ccccc1)c1cccc(Cl)c1]

Table 2, Entry 1s

Prepared according to the General Procedure A from the corresponding arylboroxine (138 mg, 0.330 mmol, 2.0 equiv. Ar—B) and dibenzyl malonate (142 mg, 0.50 mmol, 1.0 equiv.), 48 h. Isolated in 72% yield after purification by column chromatography (10:1 to 4:1 Hex/EtOAc) as a pale yellow oil.

$^1$H NMR (CDCl$_3$, 500 MHz) δ 7.41 (br, 1H), 7.33-7.28 (m, 7H), 7.28-7.25 (m, 6H), 5.21-5.14 (m, 4H), 4.68 (s, 1H);

$^{13}$C NMR (CDCl$_3$, 125 MHz) δ 167.4, 135.2, 134.6, 134.3, 130.0, 129.7, 128.8, 128.7, 128.6, 128.3, 127.8, 67.8, 57.5;

HRMS (LCMS ESI): calcd for C$_{23}$H$_{23}$ClNO$_4$ [M+NH$_4$]$^+$: 412.1316. Found 412.1325.

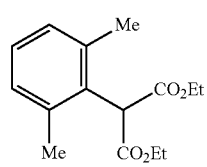 [SMILES: CCOC(=O)C(C(=O)OCC)c1c(C)cccc1C]

Table 2, Entry 1t

Prepared according to the General Procedure A from the corresponding arylboroxine (132 mg, 0.330 mmol, 2.0 equiv. Ar—B) and diethyl malonate (80 mg, 0.50 mmol, 1.0 equiv.), 48 h. Isolated in 49% yield after purification by column chromatography (10:1 to 4:1 Hex/EtOAc) as a pale yellow oil. $^1$H and $^{13}$C NMR data matched the literature data.[S13] HRMS matched the molecular formula.

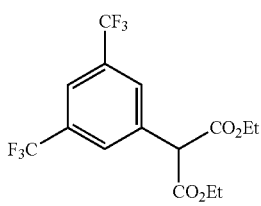 [SMILES: CCOC(=O)C(C(=O)OCC)c1cc(C(F)(F)F)cc(C(F)(F)F)c1]

Table 2, Entry 1u

Prepared according to the General Procedure A from the corresponding arylboroxine (240 mg, 0.330 mmol, 2.0 equiv. Ar—B) and diethyl malonate (80 mg, 0.50 mmol, 1.0 equiv.), 48 h. Isolated in 68% yield after purification by column chromatography (10:1 to 4:1 Hex/EtOAc) as a colorless oil.

$^1$H NMR (CDCl$_3$, 400 MHz) δ 7.90 (br, 2H), 7.87 (br, 1H), 4.73 (s, 1H), 4.30-4.21 (m, 4H), 1.29 (t, J=7.0 Hz, 6H)

$^{13}$C NMR (CDCl$_3$, 125 MHz) δ 167.0, 135.2, 132.0 (q, J=34 Hz), 129.98 (d, J=2.8 Hz), 123.3 (q, J=271 Hz), 122.5 (m), 62.7, 57.5, 14.1;

$^{19}$F NMR (CDCl$_3$, 377 MHz) δ −62.9

HRMS (LCMS ESI): calcd for C$_{15}$H$_{15}$F$_6$O$_4$ [M+H]$^+$: 373.0869. Found 373.0879.

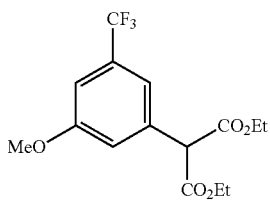 [SMILES: CCOC(=O)C(C(=O)OCC)c1cc(OC)cc(C(F)(F)F)c1]

Table 2, Entry 1v

Prepared according to the General Procedure A from the corresponding arylboroxine (202 mg, 0.330 mmol, 2.0 equiv. Ar—B) and diethyl malonate (80 mg, 0.50 mmol, 1.0 equiv.), 48 h. Isolated in 87% yield after purification by column chromatography (10:1 to 4:1 Hex/EtOAc) as a colorless oil.

$^1$H NMR (CDCl$_3$, 500 MHz) δ 7.23 (br, 1H), 7.17 (br, 1H), 7.10 (br, 1H), 4.62 (s, 1H), 4.27-4.19 (m, 4H), 3.85 (s, 3H), 1.27 (t, J=7.1 Hz, 6H);

$^{13}$C NMR (CDCl$_3$, 125 MHz) δ 167.6, 160.0, 135.2, 132.1 (q, J=32 Hz), 123.9 (q, J=271 Hz), 118.7, 188.61, 110.9 (m), 62.3, 57.8, 55.8, 14.1;

$^{19}$F NMR (CDCl$_3$, 377 MHz) δ −62.7

HRMS (LCMS ESI): calcd for C$_{15}$H$_{18}$F$_3$O$_5$ [M+H]$^+$: 335.1101. Found 335.1107.

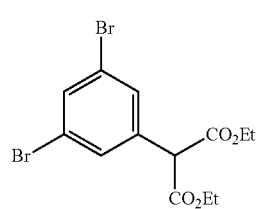 [SMILES: CCOC(=O)C(C(=O)OCC)c1cc(Br)cc(Br)c1]

Table 2, Entry 1w

Prepared according to the General Procedure A from the corresponding arylboroxine (262 mg, 0.330 mmol, 2.0 equiv. Ar—B) and diethyl malonate (80 mg, 0.50 mmol, 1.0 equiv.), 24 h. Isolated in 78% yield after purification by column chromatography (10:1 to 4:1 Hex/EtOAc) as a colorless oil.

$^1$H NMR (CDCl$_3$, 500 MHz) δ 7.65 (m, 1H), 7.51 (m, 2H), 4.51 (s, 1H), 4.29-4.18 (m, 4H), 1.28 (t, J=7.2 Hz, 6H);

$^{13}$C NMR (CDCl$_3$, 125 MHz) δ 167.2, 136.3, 134.2, 131.4, 123.0, 62.4, 57.1, 14.1;

HRMS (LCMS ESI): calcd for C$_{13}$H$_{15}$Br$_2$O$_4$[M+H]$^+$: 392.9332. Found 392.9340.

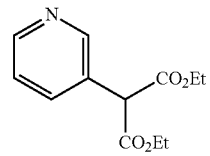 [SMILES: CCOC(=O)C(C(=O)OCC)c1cccnc1]

Table 2, Entry 1x

Prepared according to the General Procedure A from the corresponding arylboroxine (105 mg, 0.330 mmol, 2.0 equiv. Ar—B) and diethyl malonate (80 mg, 0.50 mmol, 1.0 equiv.), 48 h. Isolated in 43% yield after purification by column chromatography (1:1 to 1:3 Hex/EtOAc) as a pale yellow oil. $^1$H and $^{13}$C NMR data agreed with literature data.$^{S12}$ HRMS matched the molecular formula.

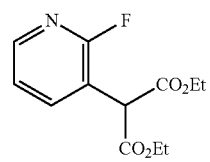 [SMILES: CCOC(=O)C(C(=O)OCC)c1cccnc1F]

Table 2, Entry 1y

Prepared according to the General Procedure A from the corresponding arylboroxine (123 mg, 0.330 mmol, 2.0 equiv. Ar—B) and diethyl malonate (80 mg, 0.50 mmol, 1.0 equiv.), 48 h. Isolated in 63% yield after purification by column chromatography (10:1 to 1:1 Hex/EtOAc) as a pale yellow oil.

$^1$H NMR (CDCl$_3$, 500 MHz) δ 8.20 (m, 1H), 7.99 (m, 1H), 7.23 (m, 1H), 4.93 (s, 1H), 4.30-4.20 (m, 4H), 1.28 (t, J=7.2 Hz, 6H);

$^{13}$C NMR (CDCl$_3$, 125 MHz) δ 167.0, 161.3 (d, J=238 Hz), 147.6 (d, J=15 Hz), 141.6 (d, J=3.8 Hz), 121.8 (d, J=4.5 Hz), 115.8 (d, J=29 Hz), 62.5, 50.42 (d, J=1.5 Hz), 14.1;

$^{19}$F NMR (CDCl$_3$, 377 MHz) δ −72.53 (d, J=9.6 Hz)

HRMS (LCMS ESI): calcd for C$_{12}$H$_{15}$FNO$_4$ [M+H]$^+$: 256.098 Found: 256.0982.

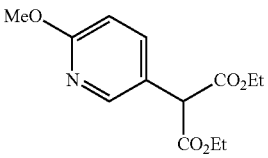

Table 2, Entry 1z

Prepared according to the General Procedure A from the corresponding arylboroxine (135 mg, 0.330 mmol, 2.0 equiv. Ar—B) and diethyl malonate (80 mg, 0.50 mmol, 1.0 equiv.), 24 h. Isolated in 53% yield after purification by column chromatography (10:1 to 4:1 Hex/EtOAc) as a pale yellow oil. $^1$H and $^{13}$C NMR data agreed with literature data.$^{S13}$ HRMS matched the molecular formula.

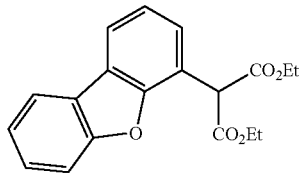 [SMILES: CCOC(=O)C(C(=O)OCC)c1cccc2c1oc1ccccc12]

Table 2, Entry 1aa

Prepared according to the General Procedure from the corresponding arylboroxine (194 mg, 0.330 mmol, 2.0 equiv. Ar—B) and diethyl malonate (80 mg, 0.50 mmol, 1.0 equiv.), 48 h. Isolated in 69% yield after purification by column chromatography (10:1 Hex/EtOAc) as a pale yellow oil.

$^1$H NMR (CDCl$_3$, 500 MHz) δ 7.95 (d, J=7.5 Hz, 1H), 7.92 (dd, J=1.5, 7.5 Hz, 1H), 7.60-7.57 (m, 2H), 7.46 (m, 1H), 7.39-7.33 (m, 2H), 5.39 (s, 1H), 4.30-4.22 (m, 4H), 1.28 (t, J=7.5 Hz, 6H);

$^{13}$C NMR (CDCl$_3$, 125 MHz) δ 167.9, 156.2, 154.4, 127.44, 127.42, 124.51, 124.47, 123.12, 123.06, 120.9, 120.7, 117.3, 112.0, 62.1, 51.7, 14.2;

HRMS (LCMS ESI): calcd for C$_{19}$H$_{19}$O$_5$[M+H]$^+$: 327.1227 Found: 327.1232.

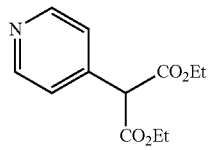

Table 2, Entry 1ab

Prepared according to the General Procedure B from the corresponding neopentyl boronic ester (48 mg, 0.25 mmol, 1.0 equiv.) and diethyl malonate (80 mg, 0.50 mmol, 2.0 equiv.), stirred at 35° C., 44 h. Isolated in 53% yield after purification by column chromatography (5% MeOH/CH$^2$Cl$^2$, treated with ~0.5% NH$_4$OH) as a colorless solid.

$^1$H NMR (CDCl$_3$, 500 MHz) δ 8.61 (br, 2H), 7.33 (br, 2H), 4.57 (s, 1H), 4.26-4.17 (m, 4H), 1.25 (t, J=9.0 Hz, 6H);

$^{13}$C NMR (CDCl$_3$, 125 MHz) δ 167.0, 150.1, 141.4, 124.5, 62.4, 57.4, 14.1;

HRMS (LCMS ESI): calcd for C$_{12}$H$_{16}$NO$_4$ [M+H]$^+$: 238.1074. Found 238.1074.

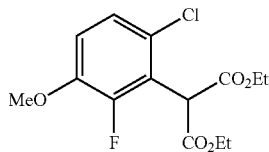 [SMILES: CCOC(=O)C(C(=O)OCC)c1c(Cl)ccc(OC)c1F]

Table 2, Entry 1ac

Prepared according to the General Procedure B from the corresponding neopentyl boronic ester (136 mg, 0.500 mmol, 1.00 equiv.) and diethyl malonate (160 mg, 1.00 mmol, 2.00 equiv.), stirred at 35° C., 48 h. Isolated in 75% yield after purification by column chromatography (10:1 to 4:1 Hex/EtOAc) as an off-white solid.

$^1$H NMR (CDCl$_3$, 500 MHz) δ 7.14 (dd, J=2.2, 8.7 Hz, 1H), 6.90 (t, J=9.0 Hz, 1H), 5.12 (s, 1H), 4.26 (q, J=7.5 Hz, 4H), 3.88 (s, 3H), 1.28 (t, J=7.5 Hz, 6H);

$^{13}$C NMR (CDCl$_3$, 125 MHz) δ 166.8, 151.7 (d, J=250 Hz), 147.2 (d, J=11 Hz), 126.0 (d, J=4.25 Hz), 124.6 (d, J=4.0 Hz), 121.6 (d, J=14.5 Hz), 113.8 (d, J=2.3 Hz), 62.3, 56.7, 51.6, 14.1;

$^{19}$F NMR (CDCl$_3$, 376 MHz) δ-129.6 (d, J=9.0 Hz)

HRMS (LCMS ESI): calcd for C$_{14}$H$_{17}$ClFO$_5$ [M+H]$^+$: 319.0743. Found 319.0745.

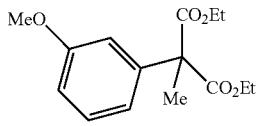 [SMILES: CCOC(=O)C(C)(C(=O)OCC)c1cccc(OC)c1]

Table 3, Entry 2a

Prepared according to the General Procedure A from the corresponding arylboroxine (201 mg, 0.500 mmol, 3.0 equiv. Ar—B) and diethyl methylmalonate (87 mg, 0.50 mmol, 1.0 equiv.), stirred at room temperature, 72 h. Isolated in 57% yield after purification by column chromatography (10:1 to 4:1 Hex/EtOAc) as a colorless oil.

$^1$H NMR (CDCl$_3$, 500 MHz) δ 7.26 (t, J=10 Hz, 1H), 6.96-6.94 (m, 2H), 6.84 (m, 1H), 4.28-4.19 (m, 4H), 3.80 (s, 3H), 1.85 (s, 3H), 1.26 (t, J=7.5 Hz, 6H);

$^{13}$C NMR (CDCl$_3$, 125 MHz) δ 171.6, 159.5, 140.0, 129.2, 120.0, 114.1, 112.8, 61.8, 58.9, 55.4, 22.6, 14.1;

HRMS (LCMS ESI): calcd for C$_{15}$H$_{21}$O$_5$[M+H]$^+$: 281.1384. Found 281.1386.

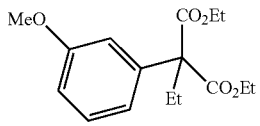

Table 3, Entry 2b

Prepared according to the General Procedure A from the corresponding arylboroxine (201 mg, 0.500 mmol, 3.0 equiv. Ar—B) and diethyl ethylmalonate (94 mg, 0.50 mmol, 1.0 equiv.), stirred at room temperature, 72 h. Isolated in 49% yield after purification by column chromatography (15:1 to 10:1 Hex/EtOAc) as a colorless oil.

$^1$H NMR (CDCl$_3$, 500 MHz) δ 7.28 (m, 1H), 7.06-7.02 (m, 2H), 6.85 (dd, J=2.3, 8.13 Hz, 1H), 4.25 (m, 4H), 3.83 (s, 3H), 2.36 (q, J=7.5 Hz, 2H), 1.27 (t, J=7.0 Hz, 6H), 0.92 (t, J=7.5 Hz, 3H);

$^{13}$C NMR (CDCl$_3$, 125 MHz) δ 170.8, 159.4, 138.4, 129.1, 120.6, 114.6, 112.7, 63.2, 61.5, 55.4, 29.2, 14.2, 9.5;

HRMS (LCMS ESI): calcd for C$_{16}$H$_{23}$O$_5$[M+H]$^+$: 295.1540. Found 295.1541.

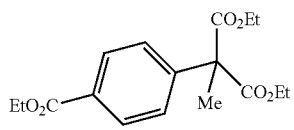 [SMILES: CCOC(=O)c1ccc(C(C)(C(=O)OCC)C(=O)OCC)cc1]

Table 3, Entry 2c

Prepared according to the General Procedure A from the corresponding arylboroxine (264 mg, 0.500 mmol, 3.0 equiv. Ar—B) and diethyl methylmalonate (87 mg, 0.50 mmol, 1.0 equiv.), stirred at room temperature, 72 h. Isolated in 40% yield after purification by column chromatography (10:1 to 7:1 Hex/EtOAc) as a colorless oil.

$^1$H NMR (CDCl$_3$, 500 MHz) δ 8.01 (m, 2H), 7.44 (m, 2H), 4.36 (q, J=7.5 Hz, 2H), 4.26-4.19 (m, 4H), 1.86 (s, 3H), 1.37 (t, J=8.5 Hz, 3H), 1.24 (t, J=7.0 Hz, 6H);

$^{13}$C NMR (CDCl$_3$, 125 MHz) δ 171.1, 166.3, 143.3, 129.8, 129.4, 127.6, 62.0, 61.1, 59.0, 22.4, 14.4, 14.0;

HRMS (LCMS ESI): calcd for C$_{17}$H$_{23}$O$_6$[M+H]$^+$: 323.1489. Found 323.1487.

Table 3, Entry 2d

Prepared according to the General Procedure B from the corresponding neopentyl boronic ester (44.4 mg, 0.200 mmol, 1.00 equiv.) and diethyl methylmalonate (69.7 mg, 0.400 mmol, 2.00 equiv.), stirred at 35° C., 72 h. Isolated in 70% yield after purification by column chromatography (20:1 to 15:1 Hex/EtOAc) as a colorless oil.

$^1$H NMR (CDCl$_3$, 500 MHz) δ 5.86 (dd, J=1.4, 16 Hz, 1H), 5.50 (dd, J=6.8, 16 Hz, 1H), 4.17 (q, J=7.1 Hz, 4H), 1.98 (m, 1H), 1.74-1.67 (m, 4H), 1.62 (m, 1H), 1.50 (s, 3H), 1.29-1.20 (m, 8H), 1.15 (m, 1H), 1.10-1.02 (m, 2H);

$^{13}$C NMR (CDCl$_3$, 125 MHz) δ 171.7, 137.9, 125.8, 61.5, 55.5, 40.8, 32.8, 26.3, 26.1, 20.6, 14.1;

HRMS (LCMS ESI): calcd for C$_{16}$H$_{27}$O$_4$[M+H]$^+$: 283.1904. Found 283.1899.

Table 3, Entry 2e

Prepared according to the General Procedure B from the corresponding neopentyl boronic ester (43.2 mg, 0.200 mmol, 1.00 equiv.) and diethyl methylmalonate (69.7 mg, 0.400 mmol, 2.00 equiv.), stirred at 35° C., 48 h. Isolated in 61% yield after purification by column chromatography (toluene) as a colorless oil.

$^1$H NMR (CDCl$_3$, 500 MHz) δ 7.42-7.40 (m, 2H), 7.33-7.30 (m, 2H), 7.26 m (1H), 6.70 (d, J=16 Hz, 1H), 6.51 (d, J=16 Hz, 1H), 4.26-4.20 (m, 4H), 1.68 (s, 3H), 1.27 (t, J=7.5 Hz, 6H);

$^{13}$C NMR (CDCl$_3$, 125 MHz) δ 171.2, 136.7, 130.9, 128.7, 128.0, 127.8, 126.7, 61.8, 55.8, 20.5, 14.2;

HRMS (LCMS ESI): calcd for C$_{16}$H$_{21}$O$_4$ [M+H]$^+$: 277.1434. Found 277.1430.

Table 3, Entry 2f

Prepared according to the General Procedure B from the corresponding neopentyl boronic ester (43.2 mg, 0.200 mmol, 1.00 equiv.) and diethyl benzylmalonate (100 mg, 0.400 mmol, 2.00 equiv.), stirred at 35° C., 48 h. Isolated in 57% yield after purification by column chromatography (toluene) as a white solid.

$^1$H NMR (CDCl$_3$, 500 MHz) δ 7.39-7.34 (m, 2H), 7.34-7.28 (m, 2H), 7.28-7.21 (m, 4H), 7.15-7.13 (m, 2H), 4.24 (q, J=7.0 Hz, 4H), 3.50 (s, 2H), 1.26 (t, J=7.0 Hz, 6H);

$^{13}$C NMR (CDCl$_3$, 125 MHz) δ 170.3, 136.7, 135.9, 131.5, 130.3, 128.7, 128.3, 128.0, 127.09, 127.08, 126.7, 61.8, 60.9, 42.8, 14.1;

HRMS (LCMS ESI): calcd for C$_{22}$H$_{25}$O$_4$[M+H]$^+$: 353.1747. Found 353.1745.

Table 3, Entry 2g

Prepared according to the General Procedure B from the corresponding neopentyl boronic ester (44.4 mg, 0.200 mmol, 1.00 equiv.) and diethyl 2-(3-chloropropyl)malonate (94.7 mg, 0.400 mmol, 2.00 equiv.), stirred at 35° C., 72 h. Isolated in 50% yield after purification by column chromatography (20:1 to 15:1 Hexane/EtOAc) as a colorless oil.

$^1$H NMR (CDCl$_3$, 500 MHz) δ 5.89 (dd, J=16 Hz, 1.5 Hz, 1H), 5.52 (dd, J=16 Hz, 7.0 Hz, 1H), 4.21-4.14 (m, 4H), 3.49 (t, J=6.5 Hz, 2H), 2.15-2.12 (m, 2H), 2.0 (br, 1H), 1.72-1.61 (m, 7H), 1.27-1.21 (m, 8H), 1.19-1.03 (m, 3H);

$^{13}$C NMR (CDCl$_3$, 125 MHz) δ 170.8, 139.0, 123.9, 61.5, 58.7, 45.0, 40.9, 32.9, 32.7, 27.8, 26.2, 26.0, 14.1;

HRMS (LCMS ESI): calcd for C$_{18}$H$_{30}$ClO$_4$ [M+H]$^+$: 345.1827. Found 345.1823.

Table 4, Entry 3a

Prepared according to the General Procedure A from the corresponding arylboroxine (83 mg, 0.20 mmol, 2.00 equiv. Ar—B) and amido ester (93 mg, 0.50 mmol, 1.0 equiv.), stirred at room temperature, 3 h. Isolated in 85% yield after purification by column chromatography (4:1 to 1:3 Hex/EtOAc) as a colorless oil.

$^1$H NMR (CDCl$_3$, 500 MHz) δ 7.41 (m, 1H), 7.33-7.28 (m, 3H), 4.66 (s, 1H), 4.27-4.17 (m, 2H), 3.59-3.42 (m, 3H), 3.25-3.20 (m, 1H), 1.97-1.80 (m, 4H), 1.26 (t, J=7.2 Hz, 3H)

$^{13}$C NMR (CDCl$_3$, 125 MHz) δ 168.3, 165.7, 135.2, 134.5, 129.9, 129.8, 128.4, 127.9, 62.0, 57.4, 47.0, 46.5, 26.2, 24.4, 14.2;

HRMS (LCMS ESI): calcd for C$_{15}$H$_{19}$ClNO$_3$ [M+H]$^+$: 296.1048. Found 296.1050.

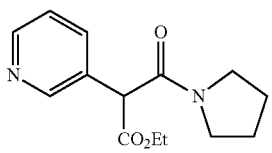

Table 4, Entry 3b

Prepared according to the General Procedure A from the corresponding arylboroxine (105 mg, 0.330 mmol, 2.0 equiv. Ar—B) and amido ester (93 mg, 0.50 mmol, 1.0 equiv.), 23 h. Isolated in 69% yield after purification by column chromatography (2% to 10% MeOH/CH$_2$Cl$_2$, treated with ~1% NH$_4$OH) as a orange oil.

$^1$H NMR (CDCl$_3$, 500 MHz) δ 8.53 (dd, J=1.6, 5.0 Hz, 1H), 8.48 (d, J=1.7 Hz, 1H), 7.91 (dt, J=2.0, 8.0 Hz, 1H), 7.28 (dd, J=5.0, 8.0 Hz, 1H), 4.69 (s, 1H), 4.21-4.14 (m, 2H), 3.56-3.51 (m, 2H), 3.40 (m, 1H), 3.27 (m, 1H), 1.95-1.79 (m, 4H), 1.23 (t, J=7.0 Hz, 3H);

$^{13}$C NMR (CDCl$_3$, 125 MHz) δ 168.0, 165.2, 150.3, 149.4, 137.5, 129.5, 123.6, 62.0, 54.8, 47.0, 46.5, 26.1, 24.3, 14.1;

HRMS (LCMS ESI): calcd for C$_{14}$H$_{19}$N$_2$O$_3$ [M+H]$^+$: 263.1396. Found 263.1392.

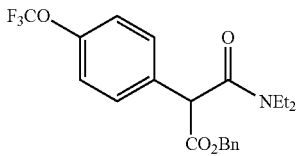

Table 4, Entry 3c

Prepared according to the General Procedure A from the corresponding arylboroxine (113 mg, 0.200 mmol, 1.2 equiv. Ar—B) and amido ester (125 mg, 0.50 mmol, 1.0 equiv.), stirred at room temperature, 5 h. Isolated in 66% yield after purification by column chromatography (4:1 to 1:1 Hex/EtOAc) as an off-white solid.

$^1$H NMR (CDCl$_3$, 500 MHz) δ 7.45-7.44 (m, 2H), 7.34-7.30 (m, 5H), 7.21-7.19 (m, 2H), 5.24-5.17 (m, 2H), 4.85 (s, 1H), 3.44-3.33 (m, 2H), 3.27-3.22 (m, 2H), 1.10 (t, J=7.5 Hz, 3H), 1.06 (t, J=7.2 Hz, 3H);

$^{13}$C NMR (CDCl$_3$, 125 MHz) δ 168.6, 166.5, 149.1 (d, J=1.5 Hz), 135.7, 132.4, 131.0, 128.6, 128.4, 128.2, 121.1, 120.6 (q, J=256 Hz), 67.5, 55.3, 42.7, 40.9, 14.3, 12.8;

$^{19}$F NMR (CDCl$_3$, 377 MHz) δ –57.8

HRMS (LCMS ESI): calcd for C$_{21}$H$_{23}$F$_3$NO$_4$ [M+H]$^+$: 410.1574 Found: 410.1577.

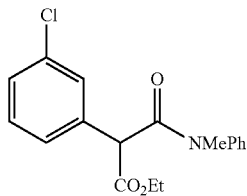

Table 4, Entry 3d

Prepared according to the General Procedure A from the corresponding arylboroxine (138 mg, 0.330 mmol, 2.0 equiv. Ar—B) and amido ester (111 mg, 0.50 mmol, 1.0 equiv.), 2.5 h. Isolated in 57% yield after purification by column chromatography (4:1 to 1:1 Hex/EtOAc) as a colorless oil.

$^1$H NMR (CDCl$_3$, 500 MHz) δ 7.44-7.39 (m, 3H), 7.25 (m, 1H), 7.19 (m, 1H), 7.12-7.04 (m, 4H), 4.55 (s, 1H), 4.19-4.14 (m, 2H), 3.28 (s, 3H), 1.25 (t, J=7.0, 3H);

$^{13}$C NMR (CDCl$_3$, 125 MHz) δ 168.4, 167.4, 143.3, 135.6, 134.1, 130.1, 129.8, 129.6, 128.7, 128.2, 128.0, 127.9, 61.9, 55.5, 38.0, 14.2;

HRMS (LCMS ESI): calcd for C$_{18}$H$_{19}$ClNO$_3$ [M+H]$^+$: 332.1048. Found 332.1047.

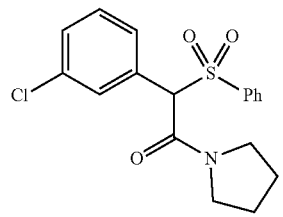 [SMILES: O=C(C(c1cccc(Cl)c1)S(=O)(=O)c1ccccc1)N1CCCC1]

Table 4, Entry 4a

Prepared according to the General Procedure A from the corresponding arylboroxine (83 mg, 0.20 mmol, 1.2 equiv. Ar—B) and sulfonyl amide (127 mg, 0.50 mmol, 1.0 equiv.), stirred at room temperature, 48 h. Isolated in 86% yield after purification by column chromatography (3:1 to 1:3 Hex/EtOAc) as a white solid.

$^1$H NMR (CDCl$_3$, 500 MHz) δ 7.62-7.57 (m, 3H), 7.42-7.39 (m, 2H), 7.36 (m, 1H), 7.33-7.32 (m, 1H), 7.29 (m, 1H), 7.20 (m, 1H), 5.19 (s, 1H), 3.61 (m, 1H), 3.55 (m, 1H), 3.39 (m, 1H), 3.26 (m, 1H), 1.96-1.78 (m, 4H).

$^{13}$C NMR (CDCl$_3$, 125 MHz) δ 162.3, 136.1, 134.6, 134.2, 130.81, 130.78, 130.7, 129.81, 129.80, 128.9, 128.3, 73.8, 47.3, 46.6, 26.2, 24.4;

HRMS (LCMS ESI): calcd for C$_{18}$H$_{19}$ClNO$_3$S [M+H]$^+$: 364.0769. Found 364.0769.

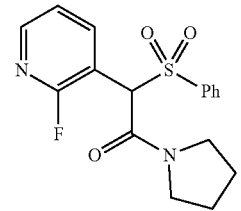 [SMILES: O=C(C(c1cccnc1F)S(=O)(=O)c1ccccc1)N1CCCC1]

Table 4, Entry 4b

Prepared according to the General Procedure A from the corresponding arylboroxine (74 mg, 0.20 mmol, 1.2 equiv. Ar—B) and sulfonyl amide (127 mg, 0.50 mmol, 1.0 equiv.), stirred at room temperature, 48 h. Isolated in 63% yield after purification by column chromatography (1:1 Hex/EtOAc to 100% EtOAc) as a white solid.

$^1$H NMR (CDCl$_3$, 500 MHz) δ 8.50 (m, 1H), 8.17 (m, 1H), 7.69-7.62 (m, 3H), 7.49-7.46 (m, 2H), 7.18 (m, 1H), 5.62 (d, J=1.3 Hz, 1H), 3.72 (m, 1H), 3.55 (m, 1H), 3.50-3.39 (m, 2H), 2.00-1.64 (m, 4H);

$^{13}$C NMR (CDCl$_3$, 125 MHz) δ 161.2 (d, J=237 Hz), 160.8, 148.5 (d, J=15 Hz), 143.5 (d, J=2.5 Hz), 136.9, 134.6, 129.7, 129.1, 121.8 (d, J=4.25 Hz), 112.1 (d, J=28 Hz), 63.8 (d, J=2.5 Hz), 47.6, 46.9, 26.1, 24.4;

$^{19}$F NMR (CDCl$_3$, 469 MHz) δ-74.3 (d, J=9.2 Hz)

HRMS (LCMS ESI): calcd for C$_{17}$H$_{18}$FN$_2$O$_3$S [M+H]$^+$: 349.1017. Found 349.1017.

Table 4, Entry 4c

Prepared according to the General Procedure A from the corresponding arylboroxine (113 mg, 0.20 mmol, 1.2 equiv. Ar—B) and sulfonyl amide (127 mg, 0.50 mmol, 1.0 equiv.), stirred at room temperature, 48 h. Isolated in 82% yield after purification by column chromatography (4:1 Hex/EtOAc to 100% EtOAc) as a white solid.

$^1$H NMR (CDCl$_3$, 500 MHz) δ 7.60-7.57 (m, 3H), 7.43-7.38 (m, 3H), 7.32 (m, 1H), 7.24 (br, 1H), 7.20 (m, 1H), 5.24 (s, 1H), 3.70 (m, 1H), 3.58 (m, 1H), 3.40 (m, 1H), 3.30 (m, 1H), 1.99 (m, 1H), 1.91-1.81 (m, 3H);
$^{13}$C NMR (CDCl$_3$, 125 MHz) δ 162.2, 149.2 (d, J=1.5 Hz), 136.0, 134.2, 131.2, 130.7, 129.9, 129.4, 128.4, 123.2, 122.1, 120.4 (q, J=257 Hz), 73.7, 47.4, 46.7, 26.2, 24.4;
$^{19}$F NMR (CDCl$_3$, 469 MHz) δ-57.7
HRMS (LCMS ESI): calcd for C$_{19}$H$_{19}$F$_3$NO$_4$S [M+H]$^+$: 414.0981. Found 414.0983.

Table 4, Entry 5a

Prepared according to the General Procedure A from the corresponding arylboroxine (138 mg, 0.330 mmol, 2.00 equiv. Ar—B) and phosphonyl ester (112 mg, 0.500 mmol, 1.00 equiv.), 40 h. Isolated in 53% yield after purification by column chromatography (4:1 to 1:3 Hex/EtOAc) as a yellow oil.

$^1$H NMR (CDCl$_3$, 500 MHz) δ 7.53 (m, 1H), 7.42 (m, 1H), 7.31-7.28 (m, 2H), 4.28-4.18 (m, 3H), 4.13-4.00 (m, 4H), 1.30-1.26 (m, 6H), 1.23 (t, J=5.0 Hz, 3H);
$^{13}$C NMR (CDCl$_3$, 125 MHz) δ 167.3 (d, J=4.0 Hz), 134.4 (d, J=2.8 Hz), 133.1 (d, J=8.5 Hz), 129.8 (overlapping doublets), 128.3 (d, J=2.8 Hz), 128.0 (d, J=6.3 Hz), 63.7 (d, J=6.8 Hz), 63.4 (d, J=7.3 Hz), 62.2, 52.0 (d, J=134 Hz), 16.4 (overlapping doublets), 14.2;
HRMS (LCMS ESI): calcd for C$_{14}$H$_{21}$ClO$_5$P [M+H]$^+$: 335.0815. Found 335.0812.

Table 4, Entry 5b

Prepared according to the General Procedure A from the corresponding arylboroxine (118 mg, 0.330 mmol, 2.00 equiv. Ar—B) and phosphonyl ester (112 mg, 0.500 mmol, 1.00 equiv.), 48 h. Isolated in 59% yield after purification by column chromatography (4:1 Hex/EtOAc to 100% EtOAc) as a yellow oil.

$^1$H NMR (CDCl$_3$, 500 MHz) δ 7.76 (m, 1H), 7.20-7.14 (m, 3H), 4.52 (d, J=26.0 Hz, 1H), 4.22-4.01 (m, 5H), 3.92 (m, 1H) 2.37 (s, 3H), 1.23 (m, 6H), 1.14 (t, J=7.1 Hz, 3H);
$^{13}$C NMR (CDCl$_3$, 125 MHz) δ 167.9 (d, J=2.9 Hz), 136.7 (d, J=7.8 Hz), 130.5 (d, J=2.0 Hz), 129.6 (d, J=8.0 Hz), 129.4 (d, J=4.9 Hz), 127.9 (d, J=2.9 Hz), 126.2 (d, J=2.9 Hz), 63.3 (d, J=6.3 Hz), 63.0 (d, J=7.0 Hz), 61.8, 47.5 (d, J=138 Hz), 20.1, 16.3 (d, J=5.9 Hz), 16.2 (d, J=5.9 Hz), 14.1;
HRMS (LCMS ESI): calcd for C$_{15}$H$_{24}$O$_5$P [M+H]$^+$: 315.1356. Found 315.1356.

Table 4, Entry 5c

Prepared according to the General Procedure A from the corresponding arylboroxine (188 mg, 0.330 mmol, 2.00 equiv. Ar—B) and phosphonyl ester (112 mg, 0.500 mmol, 1.00 equiv.), 48 h. Isolated in 48% yield after purification by column chromatography (4:1 Hex/EtOAc to 100% EtOAc) as a pale yellow oil.

$^1$H NMR (CDCl$_3$, 500 MHz) δ 7.57-7.55 (m, 2H), 7.19 (d, J=8.4 Hz, 2H), 4.28-4.18 (m, 3H), 4.12-4.04 (m, 3H), 4.02 (m, 1H), 1.30-1.26 (m, 6H), 1.20 (t, J=7.0 Hz, 3H);
$^{13}$C NMR (CDCl$_3$, 125 MHz) δ 167.4 (d, J=3.8 Hz), 149.1, 131.3 (d, J=6.3 Hz), 129.9 (d, J=8.5 Hz), 121.0, 120.6 (q, J=256 Hz), 63.6 (d, J=6.8 Hz), 63.4 (d, J=7.0 Hz), 62.2, 1.7 (d, J=133 Hz), 16.4 (overlapping doublets), 14.2;
$^{19}$F NMR (CDCl$_3$, 377 MHz) δ-57.9
HRMS (LCMS ESI): calcd for C$_{15}$H$_{21}$F$_3$O$_6$P [M+H]$^+$: 385.1022. Found 385.1023.

Table 4, Entry 6a

Prepared according to the General Procedure A from the corresponding arylboroxine (137 mg, 0.250 mmol, 1.50 equiv. Ar—B) and sulfonyl ester (114 mg, 0.500 mmol, 1.00 equiv.), stirred at 40° C., 72 h. Isolated in 56% yield after purification by column chromatography (20:1 to 10:1 Hex/EtOAc) as an white solid.

$^1$H NMR (CDCl$_3$, 500 MHz) δ 7.66-7.62 (m, 3H), 7.49-7.43 (m, 4H), 7.27-7.24 (m, 2H), 5.04 (s, 1H), 4.26-4.14 (m, 2H), 1.22 (t, J=7.1 Hz, 3H);
$^{13}$C NMR (CDCl$_3$, 125 MHz) δ 164.6, 136.4, 134.5, 131.99, 131.95, 130.1, 128.9, 127.0, 124.5, 74.8, 62.9, 14.0;
HRMS (LCMS ESI): calcd for C$_{16}$H$_{16}$BrO$_4$S [M+H]$^+$: 382.9947. Found 382.9954.

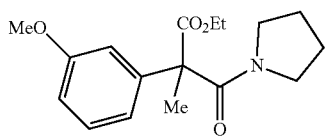 [SMILES: CCOC(=O)C(C)(C(=O)N1CCCC1)c1cccc(OC)c1]

Table 4, Entry 7a

Prepared according to the General Procedure A from the corresponding arylboroxine (101 mg, 0.250 mmol, 3.0 equiv. Ar—B) and amido ester (50 mg, 0.25 mmol, 1.0 equiv.), stirred at room temperature, 72 h. Isolated in 47% yield after purification by column chromatography (4:1 to 2:3 Hex/EtOAc) as a colorless oil.

$^1$H NMR (CDCl$_3$, 500 MHz) δ 7.22 (t, J=8.0 Hz, 1H), 7.03 (t, J=2.0 Hz, 1H), 6.96 (d, J=8.0 Hz, 1H), 6.79 (dd, J=2.0, 8.0 Hz, 1H), 4.23 (q, J=7.0 Hz, 2H), 3.78 (s, 3H), 3.58-3.54 (m, 2H), 2.89 (m, 1H), 2.73 (m, 1H), 1.78 (s, 3H), 1.75-1.61 (m, 4H), 1.27 (t, J=7.5 Hz, 3H);

$^{13}$C NMR (CDCl$_3$, 125 MHz) δ 172.0, 169.5, 159.7, 141.4, 129.5, 119.5, 113.3, 112.4, 61.6, 59.4, 55.3, 47.5, 47.1, 26.50, 26.48, 23.6, 14.2;

HRMS (LCMS ESI): calcd for C$_{17}$H$_{24c}$NO$_4$ [M+H]$^+$: 306.1700. Found 306.1701.

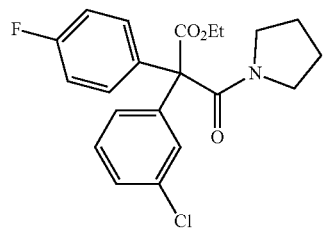 [SMILES: CCOC(=O)C(C(=O)N1CCCC1)(c1ccc(F)cc1)c1cccc(Cl)c1]

Table 4, Entry 7b

Prepared according to the General Procedure A from the corresponding arylboroxine (37 mg, 0.30 mmol, 1.2 equiv. Ar—B) and amido ester (74 mg, 0.25 mmol, 1.0 equiv.), stirred at 40° C., 25 h. Isolated in 46% yield after purification by column chromatography (4:1 Hex/EtOAc to 100% EtOAc) as a colorless oil.

$^1$H NMR (CDCl$_3$, 500 MHz) δ 7.43 (br, 1H), 7.36-7.33 (m, 2H), 7.28-7.21 (m, 3H), 7.02-6.99 (m, 2H), 4.31 (q, J=7.0 Hz, 2H), 3.61 (t, J=7.0 Hz, 2H), 2.85 (t, J=6.5 Hz, 2H), 1.82-1.78 (m, 2H), 1.71-1.66 (m, 2H), 1.29 (t, J=7.0 Hz, 3H);

$^{13}$C NMR (CDCl$_3$, 125 MHz) δ 169.9, 167.5, 162.2 (d, J=247 Hz), 140.7, 134.1, 131.3 (d, J=8.0 Hz), 129.7, 129.3, 128.1, 127.9, 127.8, 115.1 (d, J=22 Hz), 67.7, 62.4, 47.7, 47.1, 26.4, 23.6, 14.1;

$^{19}$F NMR (CDCl$_3$, 377 MHz) δ-114.5

HRMS (LCMS ESI): calcd for C$_{21}$H$_{22}$ClFNO$_3$ [M+H]$^+$: 390.1267. Found 390.1273.

VI. Derivatization of 1a and 1i to Electron-Rich Aryl Compounds Via Pd-Catalyzed Cross-Coupling In an atmosphere controlled glovebox, to a vial equipped with a stir bar was added [Pd(cinnamyl)Cl]$_2$ (0.9 mg, 0.0035 mmol Pd), BrettPhos (3.8 mg, 0.0070 mmol) and toluene (0.30 mL). The mixture was stirred for 5 minutes then transferred to a vial containing the electrophile 1a or 1i (20.5 mg, 0.065 mmol) and Cs$_2$CO$_3$ (42 mg, 0.130 mmol), rinsing with additional toluene (0.30 mL). The amine nucleophile (1.4 equiv.) was added and the vial was sealed with a PTFE lined septa cap, removed from the glovebox and stirred at 100° C. for one hour. The reaction was cooled, diluted with 4:1 Hex/EtOAc, passed through a plug of celite, concentrated and purified by column chromatography (Hex/EtOAc gradient).

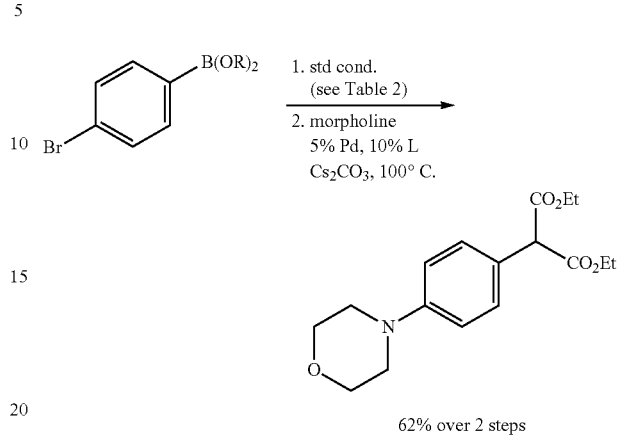

Isolated in 78% yield as pale yellow oil (62% overall from 4-bromophenylboroxine).

$^1$H NMR (CDCl$_3$, 400 MHz) δ 7.31-7.29 (m, 2H), 6.89-6.87 (m, 2H), 4.53 (s, 1H), 4.25-4.16 (m, 4H), 3.86-3.83 (m, 4H), 3.17-3.15 (m, 4H), 1.26 (t, J=7.2 Hz, 6H);

$^{13}$C NMR (CDCl$_3$, 125 MHz) δ 168.6, 151.2, 130.2, 124.1, 115.6, 67.0, 61.8, 57.3, 49.1, 14.2;

HRMS (LCMS ESI): calcd for C$_{17}$H$_{24}$NO$_5$ [M+H]$^+$: 322.1649. Found 322.1651.

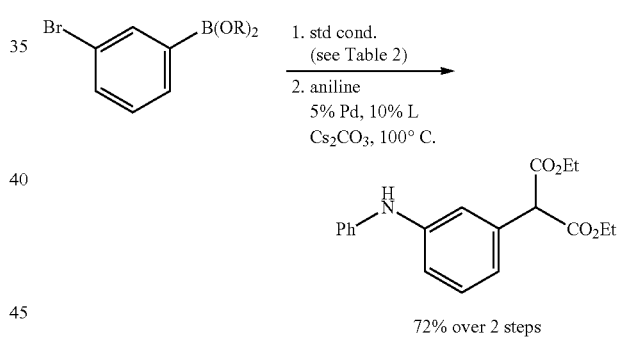

Isolated in 88% yield as pale yellow oil (72% overall from 3-bromophenylboroxine).

$^1$H NMR (CDCl$_3$, 400 MHz) □ 7.26-7.19 (m, 3H), 7.09-7.00 (m, 4H), 6.92-6.88 (m, 2H), 5.73 (br, 1H), 4.52 (s, 1H), 4.25-4.13 (m, 4H), 1.24 (t, J=6.9 Hz, 6H);

$^{13}$C NMR (CDCl$_3$, 125 MHz) □ 168.2, 143.6, 142.9, 134.1, 129.6, 129.5, 121.9, 121.4, 118.5, 118.2, 117.3, 61.9, 58.1, 14.2;

HRMS (LCMS ESI): calcd for C$_{19}$H$_{22}$NO$_4$ [M+H]$^+$: 328.1543. Found 328.1542.

REFERENCES

[1] a) C. Liu, H. Zhang, W. Shi, A. W. Lei, Chem. Rev. 2011, 111, 1780-1824; b) C. Liu, D. Liu, A. W. Lei, Acc. Chem. Res. 2014, 47, 3459-3470.

[2] a) J. X. Qiao, P. Y. S. Lam, Recent Advances in Chan-Lam Coupling Reaction: Copper-Promoted C-Heteroatom Bond Cross-Coupling Reactions with Boronic Acids and Derivatives. In Boronic Acids: Preparation and Applications in Organic Synthesis, Medicine and Materials, 2 Ed.; Hall, D. G., Ed. Wiley-VCH Verlag GmbH & Co. KGaA: 2011; 315-361; b) L. Neuville, Alternative and Emerging Reagents for the Arylation of Heteronucleophiles. In Copper-Mediated Cross-Coupling; G. Evano, N. Blachard, Eds. Wiley-VCH Verlag GmbH & Co. KGaA: 2013; 113-185.

[3] a) D. M. T. Chan, K. L. Monaco, R.-P. Wang, M. P. Winters, Tetrahedron Lett. 1998, 39, 2933-2936; b) P. Y. S. Lam, C. G. Clark, S. Saubern, J. Adams, M. P. Winters, D. M. T. Chan, A. Combs, Tetrahedron Lett. 1998, 39, 2941-2944.

[4] D. A. Evans, J. L. Katz, T. R. West, Tetrahedron Lett. 1998, 39, 2937-2940.

[5] For recent developments in Chan-Evans-Lam (CEL) heteroatom arylations see: a) W.-J. Yoo, T. Tsukamoto, S. Kobayashi, Angew. Chem. Int. Ed. 2015, 54, 6587-6590; b) B. Mudryk, B. Zheng, K. Chen, M. D. Eastgate, Org. Process Res. Dev. 2014, 18, 520-527; c) M. El Khatib, G. A. Molander, Org. Lett. 2014, 16, 4944-4947; d) F. Huang, T. D. Quach, R. A. Batey, Org. Lett. 2013, 15, 3150-3153; e) R. E. Shade, A. M. Hyde, J. C. Olsen, C. A. Merlic, J. Am. Chem. Soc. 2010, 132, 1202-1203.

[6] For recent examples of the use of CEL in complex molecule synthesis see: a) Y. Feng, D. Holte, J. Zoller, S. Umemiya, L. R. Simke, P. S. Baran, J. Am. Chem. Soc. 2015, 137, 10160-10163; b) H. Li, C. Tsu, C. Blackburn, G. Li, P. Hales, L. Dick, M. Bogyo, J. Am. Chem. Soc. 2014, 136, 13562-13565.

[7] A. E. King, B. L. Ryland, T. C. Brunold, S. S. Stahl, Organometallics 2012, 31, 7948-7957.

[8] For reviews see: a) C. C. C. Johansson, T. J. Colacot, Angew. Chem. Int. Ed. 2010, 49, 676-707; b) F. Bellina, R. Rossi, Chem. Rev. 2010, 110, 1082-1146.

[9] For recent examples of copper-catalyzed coupling of aryl electrophiles and activated methylene species (Hurtley coupling) see: a) C. He, G. H. Zhang, J. Ke, H. Zhang, J. T. Miller, A. J. Kropf, A. W. Lei, J. Am. Chem. Soc. 2013, 135, 488-493; b) S. F. Yip, H. Cheung, Z. Zhou, F. Y. Kwong, Org. Lett. 2007, 9, 3469-3472; c) X. A. Xie, G. R. Cai, D. W. Ma, Org. Lett. 2005, 7, 4693-4695; d). For a review see: Y. Jiang, D. Ma, Copper-Catalyzed Ligand Promoted Ullmann-Type Coupling Reactions. In Catalysis without Precious Metals, Wiley-VCH Verlag GmbH & Co. KGaA: 2010; 213-233.

[10] For a review of oxidative enolate coupling reactions see F. H. Guo, M. D. Clift, R. J. Thomson, Eur. J. Org. Chem. 2012, 4881-4896.

[11] Cyanation: a) C. W. Liskey, X. Liao, J. F. Hartwig, J. Am. Chem. Soc. 2010, 132, 11389-11391; Arylation: b) K. Hirano, M. Miura, Chem. Lett. 2015, 44, 868-873; Alkynylation: c) C. D. Pan, F. Luo, W. H. Wang, Z. S. Ye, J. Cheng, Tetrahedron Lett. 2009, 50, 5044-5046; Trifluoromethylation d) T. D. Senecal, A. T. Parsons, S. L. Buchwald, J. Org. Chem. 2011, 76, 1174-1176; e) L. Chu, F.-L. Qing, Org. Lett. 2010, 12, 5060-5063; Grushin and co-workers have provided strong evidence to suggest a distinct mechanistic pathway from CEL for these nucleophiles: f) N. Nebra, V. V. Grushin, J. Am. Chem. Soc. 2014, 136, 16998-17001; For cross dehydrogenative coupling reactions that generate electrophiles in situ see: g) O. Basle, C.-J. Li, Org. Lett. 2008, 10, 3661-3663; h) L. Zhao, O. Basle, C.-J. Li, Proc. Natl. Acad. Sci. U.S.A. 2009, 106, 4106-4111.

[12] For ortho-directing group enabled Cu-catalyzed arene C—H annulation reactions of activated $sp^3$ nucleophiles see: a) H.-L. Wang, M. Shang, S.-Z. Z.-L. Zhou, B. N. Laforteza, H.-X. Dai, J.-Q. Yu, Org. Lett. 2015, 17, 1228-1231; b) W. Zhu, D. Zhang, N. Yang, H. Liu, Chem. Commun. 2014, 50, 10634-10636; c) J. E. M. N. Klein, A. Perry, D. S. Pugh, R. J. K. Taylor, Org. Lett. 2010, 12, 3446-3449;

[13] A. Bunescu, Q. Wang, J. P. Zhu, Synthesis 2012, 44, 3811-3814.

[14] J. M. Stevens, D. W. C. MacMillan, J. Am. Chem. Soc. 2013, 135, 11756-11759.

[15] J. Morgan, J. T. Pinhey, J. Chem. Soc., Perkin Trans 1 1990, 715-720.

[16] Notes: a) Aryl boroxines can be prepared in quantitative fashion simply by dehydration of the boronic acid under Dean-Stark conditions, use of molecular sieves was not productive; b) up to 70% yield could be obtained using only Cu(OAc)2, see Supporting Information for details on reaction optimization including base, Cu, solvent effects, and reactions using O2 as the terminal oxidant; c) See Supporting Information for examples with morpholine and aniline; d) Acidic pro-nucleophiles such as phenol, aniline, and phenylacetylene were not tolerated; see Supporting Information for full details and additional examples. e) For aryl iodides, high conversion and moderate yields (58% calibrated GC) are observed due to non-selective oxidative degradation of the starting materials and product. For tertiary malonates moderate yields are observed due to sluggish reactivity. f) Acetophenone and 1,3-diketones are not viable substrates.

[17] K. D. Collins, F. Glorius, Nature Chem. 2013, 5, 597-601.

[18] For recent reports of the generation of arylated (all carbon) quaternary centers via cross-coupling see: a) X. Wang, S. Wang, W. Xue, G. Gong, J. Am. Chem. Soc. 2015, 137, 11562-11565; b) C. Y. Huang, A. G. Doyle, J. Am. Chem. Soc. 2015, 137, 5638-5641; c) S. L. Zultanski, G. C. Fu, J. Am. Chem. Soc. 2013, 135, 624-627;

[19] For Ni- or Pd-catalyzed 1-arylation to form quaternary centers, generally restricted to those that contain at least one methyl group or are cyclic see ref 8, for recent examples see a) P. Nareddy, L. Mantilli, L. Guenee, C. Mazet, Angew. Chem. Int. Ed. 2012, 51, 3826-3831; b) S. Z. Ge, J. F. Hartwig, J. Am. Chem. Soc. 2011, 133, 16330-16333.

[20] To the best of our knowledge this transformation is not possible by Hurtley coupling, for reports of failed attempts to arylate tertiary malonate see: a) H. J. Cristau, P. P. Cellier, J. F. Spindler, M. Taillefer, Chem. Eur. J. 2004, 10, 5607-5622; b) S. Pivsa-Art, Y. Fukui, M. Miura, M. Nomura, Bull. Chem. Soc. Jpn. 1996, 69, 2039-2042.

[21] Ma has developed ortho-directing group enabled Hurtley reactions to generate methylated quaternary center from keto esters: a) X. Xie, Y. Chen, D. Ma, J. Am. Chem. Soc. 2006, 128, 16050-16051; Tertiary cyanoacetates can be arylated by CuI at ≥60° C.; b) S. W. Xie, P. Qin, M. Li, X. J. Zhang, Y. W. Jiang, D. Ma, Tetrahedron Lett. 2013, 54, 3889-3891.

[22] For the intramolecular vinylation of activated methylene compounds with CuI/proline see: L. Chen, M. Shi, C. Li, Org. Lett. 2008, 10, 5285-5288.

[23] CuI-mediated arylation of phosphonyl esters at 90° C.: T. Minami, T. Isonaka, Y. Okada, J. Ichikawa, J. Org. Chem. 1993, 58, 7009-7015.

[24] Cu-catalyzed arylation of amido ketones at 100° C.: C. Guo, Tetrahedron Lett. 2010, 51, 548-549. Complementing this study, keto esters and cyano esters are privileged substrates for low temperature (<70° C.) Hurtley coupling, [ref 9d] these substrates are not suitable reaction partners under our standard conditions.

[25] a) For example, the antibiotics Carfecillin (1,3 amido ester) and Cefsulodin (1,3 sulfonyl amide) b) H. R. He, et. al., ACS Med. Chem. Lett. 2015, 6, 782-786; c) J. Close, et. al., (Merck & Co. Inc.), WO2008/10985 (A2), 2008.

S1 W. C. Still, M. Kahn, A. Mitra J. Org. Chem. 1978, 43, 2923-2925

S2 S. C. Matthew, B. W. Glasspoole, P. Eisenberger, and C. M. Crudden J. Am. Chem. Soc. 2014, 136, 5828-5831

S3 Y-J Huang, Y-B Jiang, S. D. Bull, J. S. Fossey, and T. D. James Chem. Commun. 2010, 46, 8180-8182

S4 J. M. Stevens, D. W. C. MacMillan J. Am. Chem. Soc. 2013, 135, 11756-11759.

S5 G. Giambastiani, B. Pacini, M. Porcelloni, and G. Poli J. Org. Chem. 1998, 63, 804-807

S6 A. V. Lozanova, T. M. Ugurchieva, and V. V. Veselovsky Russ. Chem. Bull. 2007, 56, 130-136

S7 J. Wang, Y. Yuan, R. Xiong, D. Zhang-Negrerie, Y. Du, and K. Zhao Org. Lett. 2012, 14, 2210-2213.

S8 A. Padwa, C. L. Muller, A. Rodriguez, and S. H. Watterson Tetrahedron, 1998, 54, 9651-9666

S9 B-J. Wang, P. Xuea, and P. Gu Chem. Commun., 2015, 51, 2277-2279

S10 V. Franckevicius, J. D. Cuthbertson, M. Pickworth, D. S. Pugh, and R. J. K. Taylor Org. Lett. 2011, 13, 4264-4267.

S11 S. F. Yip, H. Y Cheung, Z. Zhou and F. Y. Kwong Org. Lett., 2007, 9, 3469-3472

S12 E. J. Hennessy and S. L. Buchwald Org. Lett., 2002, 4, 269-272

S13 G. Pai and A. P. Chattopadhyay Synthesis, 2013, 45, 1475-1482

Example II—Decarboxylative Cross-Coupling

Moon, P. J., Yin, S., Lundgren, R. J. (2016) "Ambient Decarobxylative Arylation of Malonate Half-Esters via Oxidative Catalysis". Journal of the American Chemical Society". 138. 13826-13829, and the Supplementary Information therein, is incorporated by reference in their entirety.

In one aspect, there is described a method of decarboxylative α-arylation. In a specific example, there is described decarboxylative α-arylation via oxidative Cu catalysis.

In one example, there is described decarboxylative carbonyl α-arylation by coupling arylboron nucleophiles with malonic acid derivatives. This method allows for the synthesis of monoaryl acetate derivatives containing electrophilic functional groups that are incompatible with existing α-arylation reactivity paradigms.

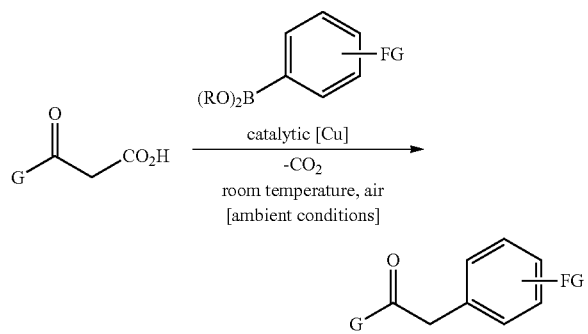

In one aspect, there is provided a method for decarboxylative carbonyl α-arylation, comprising: reacting an aryl coupling partner, a carboxylic acid, and a copper based catalyst, the reaction taking place at room temperature, exposed to air, thereby creating a carbon-carbon bond.

In another aspect, there is provided a method for decarboxylative carbonyl α-arylation, comprising: first subjecting an aryl halide to Pd-catalyzed borylation to generate an arylboronic ester, followed by reaction of the resulting product with a carboxylic acid, and a copper based catalyst, the reaction taking place at room temperature, exposed to air, thereby creating a carbon-carbon bond.

Carboxylic Acid

The reaction mixture comprises a substrate having a carboxyl group (also referred to as a carboxylic acid). Any substrate including a carboxyl group operable to undergo decarboxylative arylation described herein can be employed in the reaction mixture.

In some examples, the carboxylic acid is a malonic acid derivative.

In some examples, the carboxylic acid is a malonate ester, monoethyl malonate, monobenzyl malonate, mono-1-chlorohexyl malonate, mono-4-NBoc-piperidyl malonate, mono-geranyl malonate, 3-(methyl(phenyl)amino)-3-oxopropanoic acid, 3-oxo-3-(phenylamino)propanoic acid, 3-oxo-3-(pyrrolidin-1-yl)propanoic acid, or 3-(methoxy(methyl)amino)-3-oxopropanoic acid.

Aryl Coupling Partner

The reaction mixture comprises a coupling partner.

In one example, the coupling partner is an aryl coupling partner or heteroaryl coupling partner.

In one example, the coupling partner is an arylboronic ester or heteroaryl boronic ester.

In other examples, the coupling partner is partner is 3-iodophenyl boronic neopentyl ester [B(neop)], (ArBO)$_3$, ArB(OH)$_2$, ArBpin, or ArBF$_3$K.

Copper Based Catalyst

The reaction mixture comprises a copper base catalyst.

In one example, the copper based catalyst is a Cu(I) salt.

In one example, the copper based catalyst is a Cu(II) salt.

In other examples, copper based catalyst is Cu(OTf)$_2$, Cu(OAc)$_2$, CuSO$_4$, Cu(MeCN)$_4$PF$_6$, or CuI.

Sequential Arene Borylation/Decarboxylative Coupling

In one aspect, for example in the case where the arylboron reagent is not immediately available, the oxidative coupling may be conducted in tandem with an arene borylation. Aryl halides can be subjected to Pd-catalyzed to generate the corresponding aryl-B(neop) reagent.

Ir-catalyzed C—H borylation can be used to generate products of formal carbonyl α-C—H arylation.

Pd-Catalyst

In one aspect, there is a described a method comprising first subjecting an aryl halide to Pd-catalyzed borylation to generate an arylboronic ester, prior to reacting with a carboxylic acid and a copper based catalyst. In a specific example, the Pd-catalyst is PdCl$_2$(MeCN)$_2$.

Ir-Catalyst

In one aspect, there is described a method comprising a. subjecting an aryl halide to Ir-catalyzed borylation to generate an arylboronic ester, prior to reacting with a carboxylic acid and a copper based catalyst. In a specific example, the Ir-catalyst is [Ir(COD)(OMe)]$_2$.

Reaction Conditions

The reaction is carrier out at ambient temperature (e.g., room temperature), exposed to air, resulting in the formation of a Carbon-Carbon bond.

We report decarboxylative carbonyl α-arylation by coupling arylboron nucleophiles with malonic acid derivatives. This process is enabled by the merger of aerobic oxidative Cu-catalysis with decarboxylative enolate interception reminiscent of malonyl-CoA reactivity in polyketide biosynthesis. This method allows for the synthesis of monoaryl acetate derivatives containing electrophilic functional groups that are incompatible with existing α-arylation reactivity paradigms. The utility of the reaction is demonstrated in drug intermediate synthesis and late-stage functionalization.

In the biosynthesis of polyketides and fatty acids, carbon-carbon bond formation proceeds via decarboxylative cross-condensation between malonic acid derivatives such as malonyl-CoA and enzyme-bound acyl electrophiles.[1] A variety of conceptually related metal- or organocatalyzed reactions have been developed, in which malonates and related species undergo decarboxylation and coupling with carbonyl or allylic electrophiles.[2] These reactions obviate the need for high temperatures, strongly basic mediators or prior stoichiometric manipulations to generate the enolate component (FIG. 2A).[3] By contrast, there are limited reports of decarboxylative coupling reactions of malonate derivatives with aryl electrophiles. Pd-catalyzed coupling of malonic acid derivatives with aryl halides requires pre-deprotonation of the acid and high temperatures (≥120° C.), presumably in order to generate a Pd enolate via thermal decarboxylation.[4] The development of mild and robust methods for decarboxylative α-arylation would find broad appeal, as the preparation of polyfunctionalized monoaryl acetic acids via cross-coupling of simple acetate derivatives remains a significant challenge in synthetic chemistry.

Unstabilized acetates can be arylated via in situ enolization under strongly basic conditions incompatible with protic or electrophilic functionality[5] or subjected to stoichiometric manipulations to generate pre-formed silyl- or metal enolates.[6] These strategies significantly reduce synthetic efficiency and utility in complex molecule synthesis. Common methods used in medicinal chemistry campaigns requiring α-aryl carbonyl compounds remain traditional SNAr or metal-catalyzed coupling reactions involving dialkyl malonates, followed by hydrolysis and thermal decarboxylation. Thus, access to complex monoaryl acetic acids (such as those in FIG. 2D) generally requires multi-step, substrate specific processes.[7] The dearth of mild malonic acid decarboxylative arylation reactions stands in contrast to the burgeoning fields of radical arylative decarboxylations of α-heteroatom substituted acids via platinum-group metal photoredox catalysis[8] or the use of redox-active esters functionalized with activators to promote bond cleavage.[9]

Figure 2B:
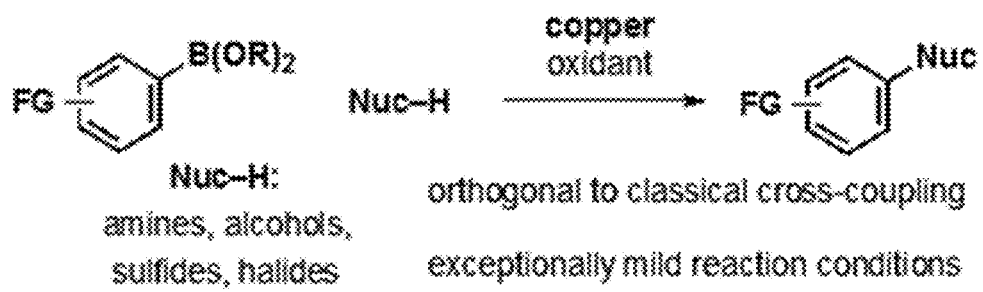
Figure 2C:
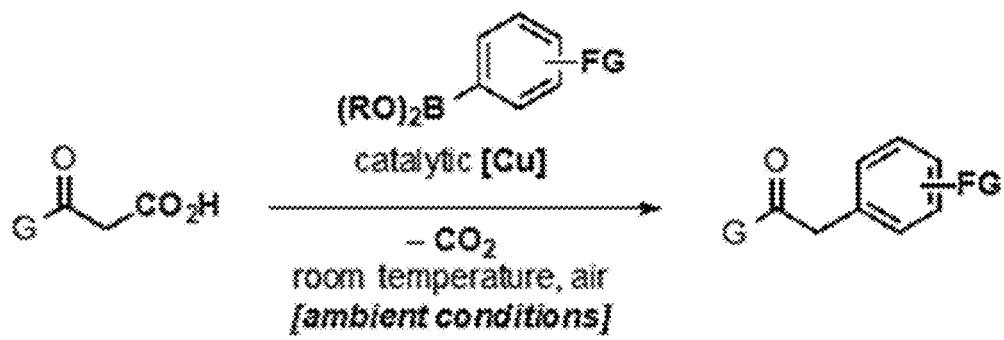
Figure 2D:
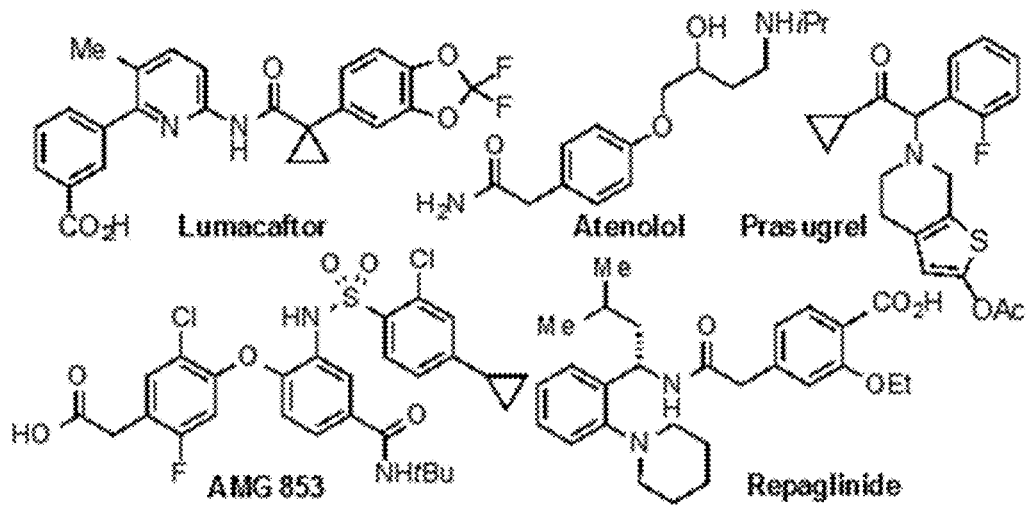

We were inspired by the exceptionally mild conditions under which Cu(II)-catalyzed decarboxylative aldol-type reactions occur[3a, 10] and hypothesized that combining the use of a Cu(II) (pre)catalyst, a malonic acid derivative, and an appropriate aryl coupling partner could allow for decarboxylative C—C bond formation without the detriments of thermal activation and strongly basic conditions. We were encouraged by the mild and robust nature of oxidative copper(II)-catalyzed cross-coupling reactions of two nucleophilic partners.[11] The Cu-catalyzed oxidative arylation of heteroatom nucleophiles with aryl boronic acids for the preparation of anilines and phenols (FIG. 2B)[12] occurs under mild conditions using the $O_2$ present in ambient air as the oxidant. This reactivity has been extended to the arylation of carbon-based nucleophiles, including the stoichiometric arylation of activated methylenes.[13] Thus, a new reactivity platform that merges ambient decarboxylation of malonic acids and aerobic copper catalysis could allow for enolate arylation to occur with unprecedented tolerance towards reactive functional groups, providing a solution to the difficulties associated with synthesizing aryl acetates (FIG. 2C). The abundance of α-aryl carbonyl units found embedded in the core of pharmaceuticals, ranging from relatively simple NSAIDs like Naproxen to structurally complex, densely functionalized bioactive molecules, such as Lumacaftor, Prasugrel, and Repaglinide, provided clear motivation for development of such a method (FIG. 2D).

Figure 3:
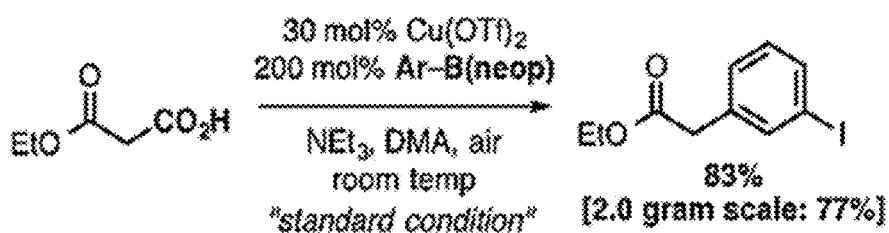
FIG. 3 is an overview of reaction discovery and optimization.
Figure 4A:
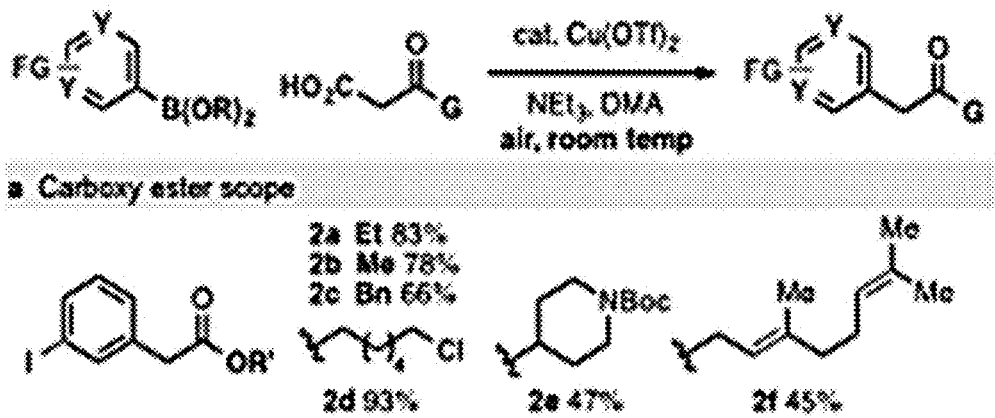
FIG. 4A-D depicts the carboxy ester scope (FIG. 4A), the aryl boronic ester scope (FIG. 4B), the heteroaryl boronic ester scope (FIG. 4C), and the carboxy amide scope (FIG. 4D) of the Cu-catalyzed decarboxylative cross-coupling of malonate derivatives and aryl boronic esters.
Figure 4B:
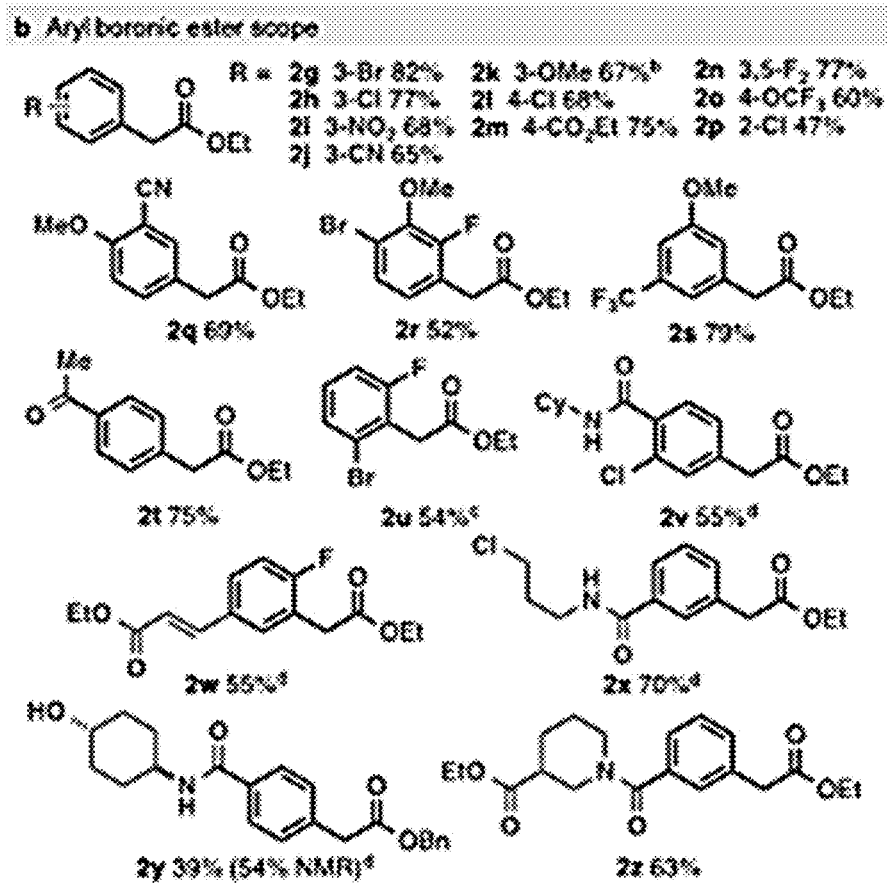
Figure 4C:
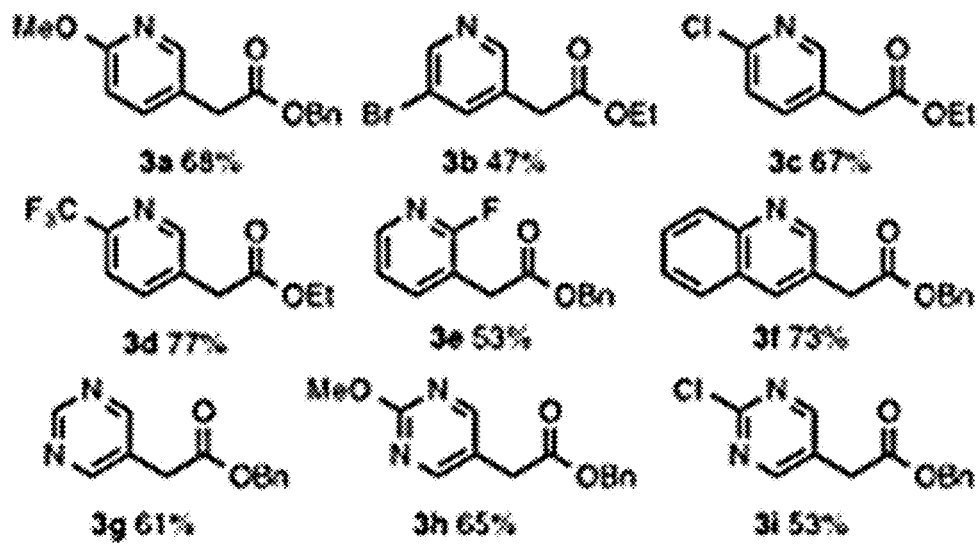
Figure 4D:
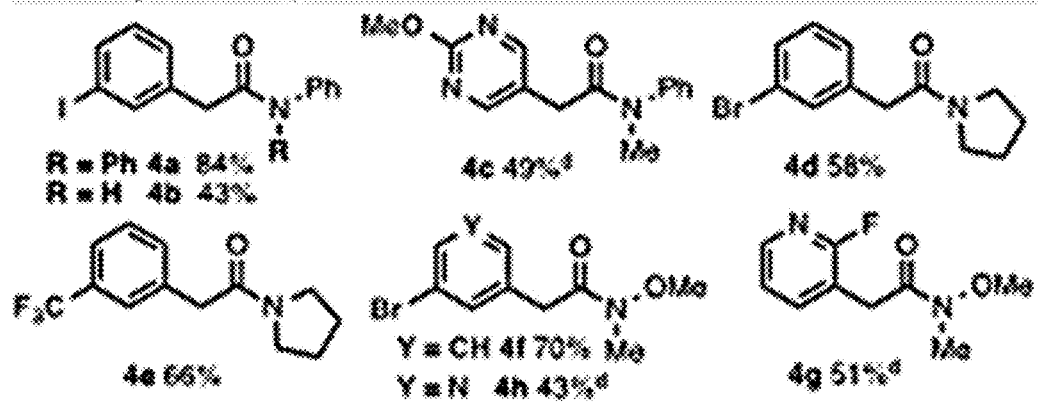

We were cognizant of the potential difficulties associated with realizing an oxidative decarboxylative arylation reaction involving malonic acids, particularly as carboxylic acids themselves are viable partners for copper-catalyzed O-arylation[14] and that irreversible decarboxylation or proto-deborylation would result in unreactive substrates. Attempts to oxidatively couple enolate equivalents with aryl boron reagents mediated by copper involving in-situ deprotonation or the use of pre-formed silyl ketene acetals were not successful. These results highlight an inherent difficulty in oxidative coupling reactions,[15] as the use of preformed enolates resulted in exclusive formation of homocoupling products derived from both reaction partners without detectable cross-coupling. Monoethyl malonate however was observed to engage in highly selective catalytic decarboxylative cross-coupling with 3-iodophenyl boronic neopentyl ester [B(neop)] in air at room temperature with $Cu(OTf)_2$ to give the desired product in 83% yield (FIG. 3). No cross- or homo-coupling at the reactive electrophilic aryl iodide site, or competing arylation of the carboxylic acid was observed. The process can be scaled up to deliver gram quantities of aryl acetate product by using an uncapped round bottom flask (77% yield, 1.6 grams of product). To briefly describe key experimental parameters in reaction development, neopentyl glycol derived boronic esters were superior to pinacol ester, boroxine, or free boronic acid forms. Alternative Cu(II) salts performed poorly, but Cu(I) species, such as $Cu(MeCN)_4PF_6$ or CuI could be used as catalysts; in these cases a significant induction period was observed.[16] These results suggest that the nature of the counterion of the Cu (pre)catalyst influences reactivity more than the initial oxidation state.

Due to the mild, ambient nature of the transformation, the oxidative decarboxylative α-arylation reaction is amenable to coupling substrates containing a host of functional groups that would be potentially complicating with established methods (FIG. 4A-D). The reaction tolerates alkyl halides (2d, 2x), aryl halides (2a-2h, 2l, 2p, 2r, 2u, 2w), enolizable ketones (2t) and esters (2z), Michael acceptors (2w), electron-rich olefins (2f), nitriles (2j, 2q) as well as protic nitro-gen (2v, 2y, 4b) and oxygen (2y) groups. The ester moiety can range from relatively simple, easy to dealkylate groups, such as methyl or benzyl, to more complex functional group-containing species (2d-2f). Heteroaryl boronic esters such as substituted pyridines (3a-3e), quinolines (3f), and pyrimidines (3g-3i), including halogenated examples, are smoothly cross-coupled to give heteroaryl acetate adducts. Malonic monoamides undergo decarboxylative (hetero)arylation under standard conditions, including NH-amides (4b), aryl-alkyl (4c) and dialkyl amides (4d, 4e). While beta-keto acids are not currently viable cross-coupling partners, Weinreb amides, versatile ketone surrogates, can be employed with both halogenated arenes and pyridines (4f-h).

Figure 5:
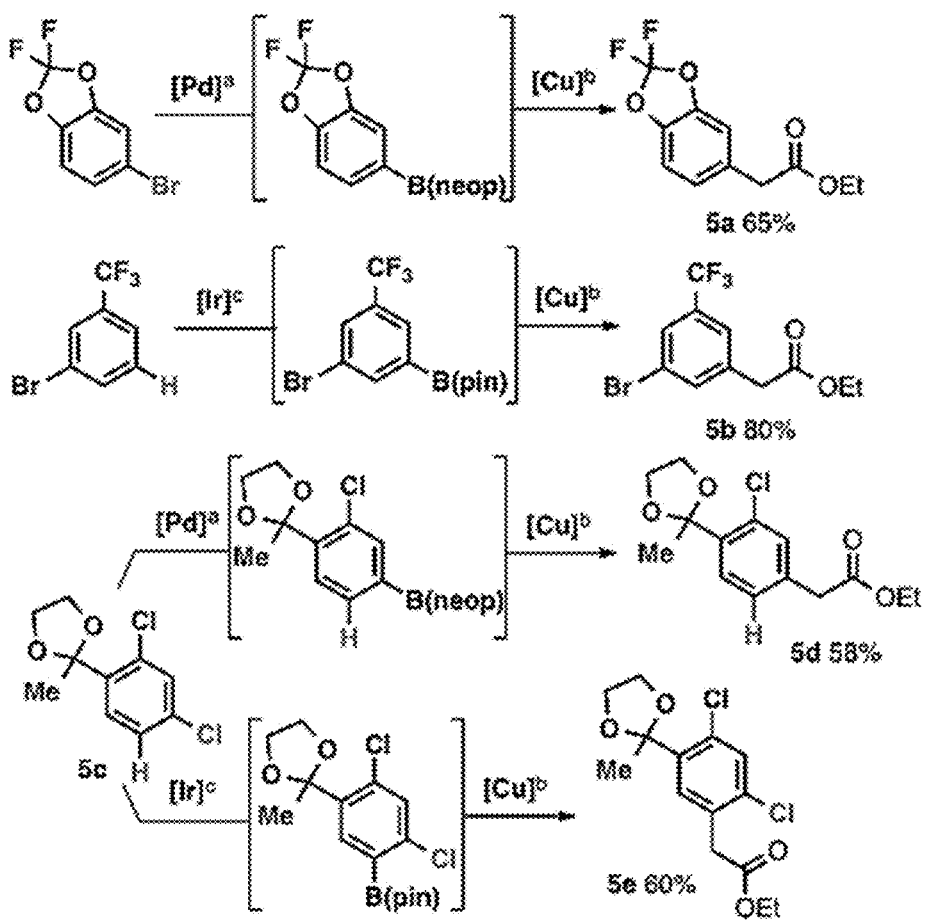
FIG. 5 depicts the sequential arene borylation/decarboxylative coupling reactions.

A large range of aryl boronic acids and esters are commercially available; however in cases in which the aryl boron reagent is not immediately available, the oxidative coupling can be conducted in tandem with an arene borylation step (FIG. 5). Aryl halides can be subjected to Pd-catalyzed borylation[17] to generate the corresponding aryl-B(neop) reagent that can be used after extractive workup without chromatographic purification to give 5a. Ir-catalyzed C—H borylation[18] can be used to generate products of formal carbonyl α-C—H arylation (5b). Leveraging the combined power of metal-catalyzed borylation and Cu-catalyzed decarboxylative malonate arylation, regiocontrolled alkylation of substituted aromatics such as chloroarene 5c can be achieved in a straightforward and predictable manner to give two distinct compounds (5d and 5e) from a common starting material.

Figure 6A:
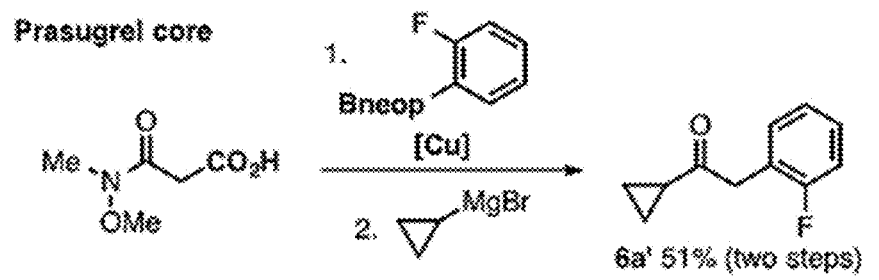
FIG. 6A-E depicts applications of Cu-catalyzed decarboxylative malonate arylation in complex molecule synthesis and functionalization, particularly in respect of a Prasugrel core (FIG. 6A), a Lumacaftor core (FIG. 6B), Nicergoline (FIG. 6C), NBoc-Paroxetine (FIG. 6D), and, Indometacin ethyl ester (FIG. 6E).
Figure 6B:
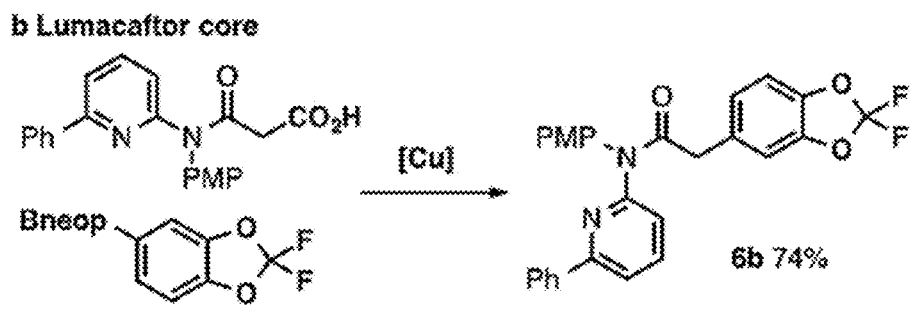

The applicability of this new copper-catalyzed decarboxylative arylation reaction was demonstrated in the preparation of the α-aryl cyclopropyl ketone core of Prasugrel (FIG. 6A), which was synthesized in 51% yield in two steps via decarboxylative arylation of the Weinreb amide derivative followed by treatment with cyclopropyl Grignard reagent. The arylated core of Lumacaftor was prepared by coupling the PMP-protected pyridyl α-carboxy amide and a functionalized aryl B(neop) reagent to deliver the target 6b (FIG. 6B) in 74% yield.

Figure 6C:
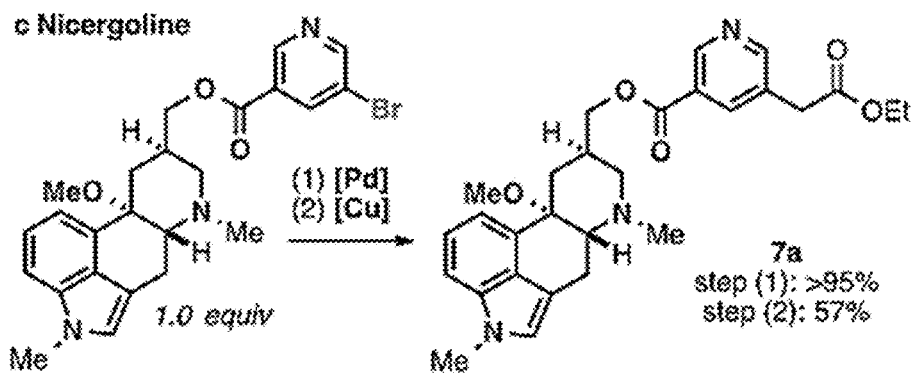

The potential to functionalize complex molecules using this ambient decarboxylative strategy was tested on a variety of arene-containing drug molecules. The complex alkaloid Nicergoline could be borylated quantitatively and cross-coupled to monoethyl malonate in 57% yield (7a, FIG. 6C).

Figure 6D:
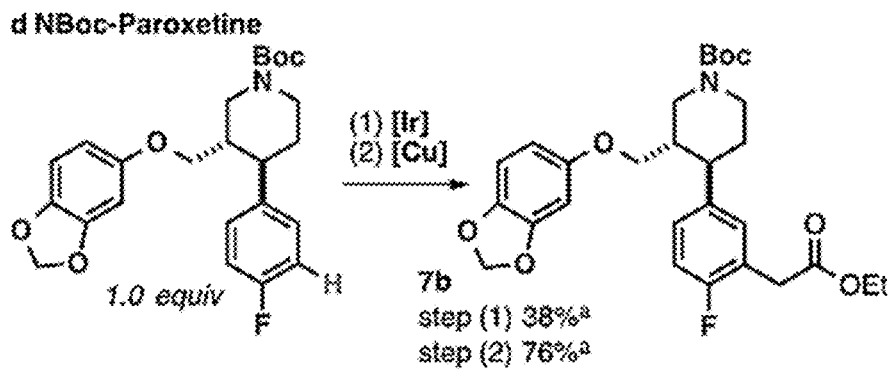
Figure 6E:
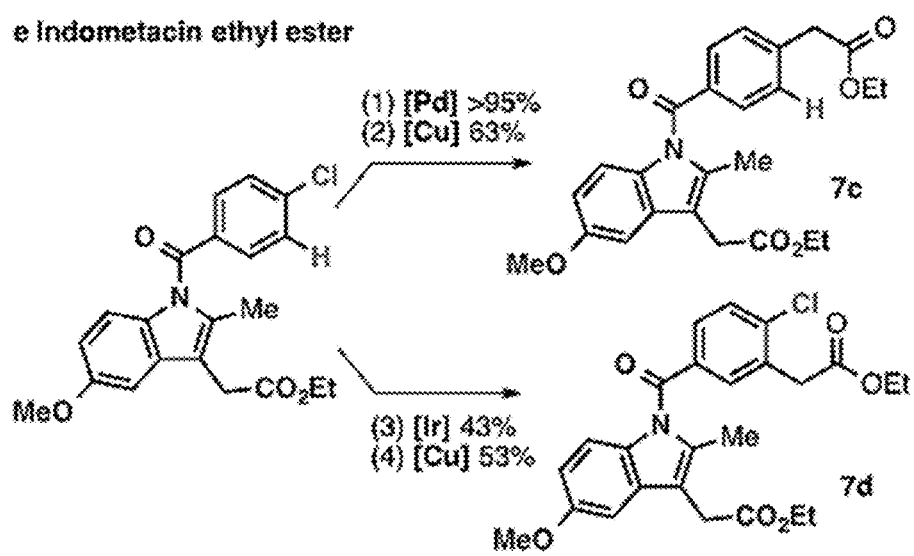

NBoc-Paroxetine could be selectively alkylated at one of the five aryl C—H positions to deliver 7b via an Ir-catalyzed diborylation/mono-deborylation strategy followed by decarboxylative cross-coupling (FIG. 6D). Indometacin ethyl ester could be diversified into two unique derivatives by employing either Pd-catalyzed aryl chloride borylation followed by oxidative coupling (7c), or Ir-catalyzed C—H borylation followed by oxidative coupling (7d) to give the aryl acetate derivatives in synthetically useful yields (63% and 53% oxidative coupling yield respectively, FIG. 6E). These results support the prospect that malonic half esters may be used as two carbon units to synthesize and diversify drug-like molecules in medicinal chemistry campaigns by employing the reactivity platform described herein.

We have reported a new oxidative coupling method for the mild and efficient construction of $sp^2$-$sp^3$ carbon-carbon bonds.[19] This decarboxylative α-arylation of malonic half esters and amides proceeds at room temperature, in air, under mildly basic conditions, and employs both a simple copper catalyst and stable aryl boronic esters. In contrast with existing enolate arylation chemistry, this oxidative strategy is compatible with protic and electrophilic functional groups, facilitating applications in late-stage functionalization. We have demonstrated that biomimetic decarboxylative trapping of malonate derivatives can provide new routes to the core of drug molecules and should find immediate use in the preparation of aryl acetates and related derivatives in the context of functional molecule synthesis.

All glassware and vials were oven-dried prior to use. Flash chromatography was performed as described by Still and co-worker1 (SiliaFlash P60, 40-63 μm, 60 A silica gel, Silicycle) or by automated flash chromatography (Isolera, HP-SIL or Ultra SNAP silica cartridges, Biotage). Analytical thin-layer chromatography was performed using glass plates pre-coated with silica (SiliaPlate G TLC—Glass-Backed, 250 μm, Silicycle). TLC plates were visualized by UV light and/or staining with aqueous basic potassium permanganate. Unless otherwise noted, all reagents were obtained from commercial vendors and used as supplied. Boronic esters leading to 2a-v, 2z, 4e, 6a, 6b[2] and 2w-y, 3a-i[3] were synthesized according to the literature procedure from the corresponding boronic acid. Indometacin ethyl ester was synthesized according to the literature procedure from indometacin.[4] Benzyl malonate half-ester was synthesized according to the literature procedure from malonic acid.[5] Geranyl malonate half-ester was synthesized according to the literature procedure from Meldrum's acid.[6] Malonyl mono-amide leading to 4f was synthesized according to the literature procedure from malonic acid.[7] Select $^{13}$C NMR spectra display an artifact signal at 189 or 206 ppm.

II. SYNTHESIS OF SUBSTRATES

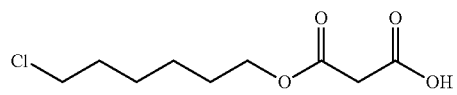 [SMILES: O=C(O)CC(=O)OCCCCCCCl]

Synthesized according to the literature procedure from Meldrum's acid and the corresponding alcohol in 54% yield (1.20 g, 5.40 mmol) as a light yellow oil.[8]

$^1$H NMR (CDCl$_3$, 700 MHz) δ 4.18 (m, 2H), 3.53 (m, 2H), 3.44 (s, 2H), 1.78 (m, 2H), 1.68 (m, 2H), 1.47 (m, 2H), 1.39 (m, 2H);

$^{13}$C NMR (CDCl$_3$, 176 MHz) δ 171.6, 167.0, 66.0, 45.0, 40.9, 32.5, 28.4, 26.5, 25.2;

HRMS (LCMS ESI): calcd for C$_9$H$_{14}$ClO$_4$ [M–H]$^-$: 221.0586. Found 221.0590.

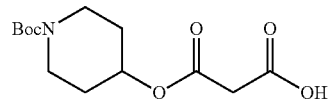 [SMILES: CC(C)(C)OC(=O)N1CCC(OC(=O)CC(=O)O)CC1]

Synthesized according to the literature procedure from Meldrum's acid (1.08 g, 7.5 mmol) and corresponding alcohol (1.39 g, 7.5 mmol). 8 Isolated in 40% yield as an off-white solid.

$^1$H NMR (CDCl$_3$, 700 MHz) δ 5.27 (m, 1H), 3.67 (br, 2H), 3.30 (s, 2H) 3.27 (m, 2H), 1.86 (br, 2H), 1.67 (br, 2H) 1.46 (s, 9H);

$^{13}$C NMR (CDCl$_3$, 176 MHz) δ169.8, 166.6, 80.2, 71.6, 71.6, 41.0, 40.7 (br), 30.4, 28.6;

HRMS (LCMS ESI): calcd for C$_{13}$H$_{20}$NO$_6$ [M–H]$^-$: 286.1296. Found 286.1295.

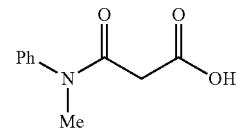

Synthesized according to the literature procedure[9] using ethyl 3-(methyl(phenyl)amino)-3-oxopropanoate (3.32 g, 15.0 mmol, 1.0 equiv.) and LiOH.H$_2$O (629 mg, 15.0 mmol, 1.0 equiv.). Isolated in 95% yield as a white solid.

$^1$H NMR (CDCl$_3$, 500 MHz) δ 7.51-7.47 (m, 2H), 7.43 (m, 1H), 7.22-7.19 (m, 2H), 3.35 (s, 3H), 3.15 (s, 2H);

$^{13}$C NMR (CDCl$_3$, 125 MHz) δ 169.7, 167.9, 141.5, 130.5, 129.1, 126.8, 37.6, 37.1;

HRMS (LCMS ESI): calcd for C$_{10}$H$_{10}$NO$_3$ [M–H]$^-$: 192.0666. Found 192.0667.

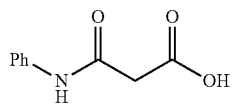

Synthesized according to the literature procedure9 using ethyl 3-oxo-3-(phenylamino)propanoate (3.11 g, 15.0 mmol, 1.0 equiv.) and LiOH.H₂O (629 mg, 15.0 mmol, 1.0 equiv.). Isolated in 64% yield as a white solid.

$^1$H NMR (DMSO-d6, 500 MHz) δ 10.09 (s, 1H), 7.57-7.55 (m, 2H), 7.31-7.28 (m, 2H), 7.04 (m, 1H), 3.34 (s, 2H);

$^{13}$C NMR (DMSO-d6, 125 MHz) δ 169.2, 164.5, 138.9, 128.7, 123.4, 119.0, 43.9;

HRMS (LCMS ESI): calcd for $C_8H_{18}NO_3$ [M–H]⁻: 178.0510. Found 178.0507.

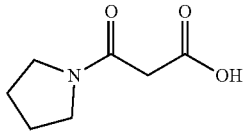 [SMILES: O=C(O)CC(=O)N1CCCC1]

Synthesized according to the literature procedure10 using benzyl 3-oxo-3-(pyrrolidin-1-yl)propanoate (3.21 g, 13.0 mmol, 1.0 equiv.) and 1M aq. NaOH (22 mL, 22 mmol, 1.7 equiv.). Isolated in 89% yield as a white solid.

$^1$H NMR (CDCl₃, 500 MHz) δ 3.55 (t, J=7.1 Hz, 2H), 3.45 (t, J=6.9 Hz, 2H), 3.32 (s, 2H), 2.07-2.01 (m, 2H), 1.97-1.91 (m, 2H);

$^{13}$C NMR (CDCl₃, 125 MHz) δ 168.3, 167.6, 46.7, 46.4, 36.0, 25.7, 24.2;

HRMS (LCMS ESI): calcd for $C_7H_{10}NO_3$ [M–H]⁻: 156.0666. Found 156.0666.

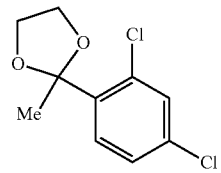 [SMILES: CC1(c2ccc(Cl)cc2Cl)OCCO1]

Synthesized according to the literature procedure11 using 1-(2,4-dichlorophenyl)ethanone (2.00 g, 10.6 mmol, 1.00 equiv.) and ethylene glycol (2.63 g, 42.3 mmol, 4.0 equiv.). Isolated in 90% yield as a colorless oil.

$^1$H NMR (CDCl₃, 500 MHz) δ 7.57 (d, J=8.3 Hz, 1H), 7.39 (d, J=2.1 Hz, 1H), 7.21 (dd, J=8.5, 2.2 Hz, 1H), 4.10-4.03 (m, 2H), 3.80-3.73 (m, 2H), 1.77 (s, 3H);

$^{13}$C NMR (CDCl₃, 125 MHz) δ 138.4, 134.4, 132.8, 131.1, 128.7, 126.7, 108.2, 64.5, 25.2;

HRMS (LCMS EI): calcd for $C_9H_7O_2Cl_2$ [M–CH₃]⁺: 216.9823. Found 216.9824.

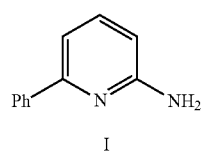 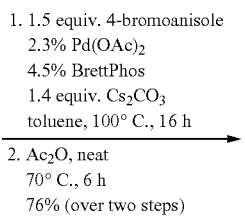

1. 1.5 equiv. 4-bromoanisole
   2.3% Pd(OAc)₂
   4.5% BrettPhos
   1.4 equiv. Cs₂CO₃
   toluene, 100° C., 16 h
2. Ac₂O, neat
   70° C., 6 h
   76% (over two steps)

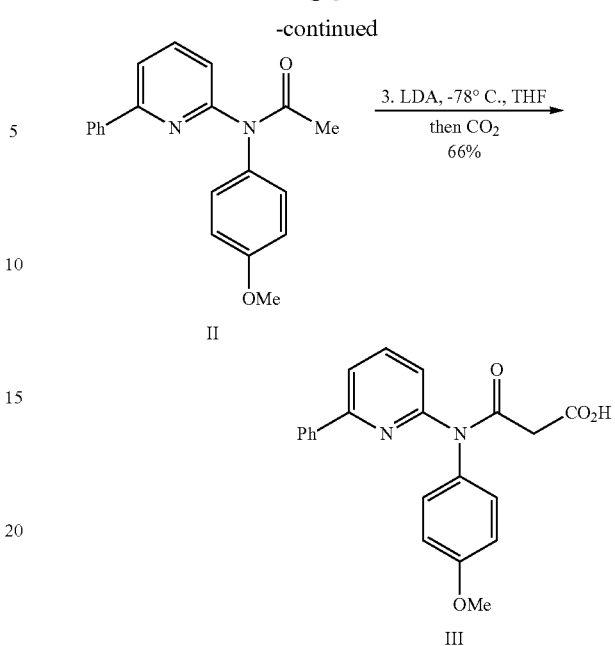

Step 1. To a 1-dram vial was added Pd(OAc)₂ (20 mg, 0.090 mmol, 0.023 equiv.) and BrettPhos (97 mg, 0.18 mmol, 0.045 equiv.) and toluene (2.0 mL). This solution was stirred for approximately 5 minutes at room temperature. To an 8 dram vial was added aminopyridine 1 (681 mg, 4.00 mmol, 1.00 equiv.), 4-bromoanisole (0.75 mL, 6.0 mmol, 1.5 equiv.), and Cs₂CO₃ (1.83 g, 5.60 mmol, 1.40 equiv.). The headspace was purged with N₂ for 5 minutes, then sealed with a PTFE lined cap. The Pd/Brettphos solution was quantitatively transferred using additional toluene (18 mL), then the mixture was heated at 100° C. After 24 h, the reaction was cooled to room temperature, passed through a celite plug, then concentrated in vacuo. The corresponding diarylamine was isolated in 83% yield after purification by column chromatography (20:1 to 7:3 Hexane/EtOAc).

Step 2. To a vial containing the diarylamine (848 mg, 3.10 mmol, 1.00 equiv.) was added acetic anhydride (1.5 mL, 15 mmol, 5.0 equiv.), then heated at 70° C. After 6 h, the reaction was cooled to room temperature and concentrated in vacuo. The crude material was dissolved in 30 ml EtOAc, then washed sequentially with sat. aq. NaHCO₃ (3×10 mL), then brine (10 mL). The organic portion was dried with Na₂SO₄, then concentrated in vacuo to afford the acetate II in 91% yield as a colorless oil.

$^1$H NMR (CDCl₃, 500 MHz) δ 7.91-7.89 (m, 2H), 7.74 (m, 1H), 7.57 (m, 1H), 7.44-7.34 (m, 4H), 7.31-7.27 (m, 2H), 6.96-6.93 (m, 2H), 3.83 (s, 3H), 2.19 (s, 3H);

$^{13}$C NMR (CDCl₃, 125 MHz) δ 171.5, 158.8, 156.1, 155.1, 138.6, 138.5, 135.0, 29.8, 129.2, 128.7, 126.8, 118.8, 117.3, 114.6, 55.5, 24.6;

HRMS (LCMS ESI): calcd for $C_{20}H_{18}N_2NaO_2$ [M+Na]⁺: 341.1260. Found 341.1268.

Step 3. To a solution of LDA (3.1 mmol, 1.1 equiv.) in THF (0.3 M) at −78° C. was added II (897 mg, 2.82 mmol, 1.0 equiv.) as a solution in THF (7 mL), to give a yellow solution. After 30 minutes, CO₂ was bubbled into the solution. After 20 minutes, the reaction was slowly warmed to room temperature and stirred for 30 minutes. Excess CO₂ was added and stirred for an additional 30 minutes. The reaction was quenched with water (30 mL) washed with Et₂O (3×20 mL). The aqueous layer was acidified to pH 3 and extracted with EtOAc (3×15 mL). The combined organic layers were dried with Na$_2$SO$_4$ and concentrated in vacuo to afford III in 66% yield as an off-white solid (85% purity). This material slowly decarboxylates at room temperature and should be used immediately or stored in a freezer.

III. DECARBOXYLATIVE ARYLATION OF MALONATE HALF ESTER DERIVATIVES

General Procedure A: Cu(OTf)$_2$ (54.3 mg, 0.150 mmol, 0.30 equiv.) and arylboronic ester (1.00 mmol, 1.20 to 2.00 equiv.) were added sequentially to a 1 dram vial charged with a stirbar. The carboxylic acid (0.500 mmol, 1.00 equiv.) was added as a solution in anhydrous DMA (0.6 mL). Additional DMA (2×0.3 mL) was used to quantitatively transfer the solution to the reaction mixture. The solution was stirred until a homogeneous pale blue solution was formed (approximately 2 minutes, partially heterogeneous mixtures obtained when using increased Cu loadings), followed by the addition of triethylamine (0.42 mL, 3.0 mmol, 6.0 equiv.). The vial was sealed with a PTFE-lined cap, exposed to air via a needle, and gently stirred at room temperature. Upon completion of the reaction (24 to 72 h), the reaction mixture was diluted with EtOAc (40 mL), and washed sequentially with NH4Cl (15 mL), 0.5 M NaOH (2×20 mL), and brine (15 mL). The organic layer was dried with Na$_2$SO$_4$, concentrated in vacuo, and purified by silica gel chromatography. No difference was observed if reactions were prepared in an atmosphere-controlled glovebox, then exposed to ambient air.

Procedure for Gram Scale Reaction:

To a 50 mL pear-shaped round bottomed flask in air was added Cu(OTf)$_2$ (942 mg, 2.16 mmol, 0.30 equiv.), 3-iodophenyl neopentyl boronic ester (4.55 g, 14.4 mmol, 2.0 equiv.), DMA (18 mL) and mono-ethyl malonate (951 mg, 7.2 mmol, 1.0 equiv.). The mixture was stirred for 10 minutes to generate a suspension to which NEt3 (6.0 mL, 43 mmol, 6 equiv.) was added. After 24 hours the reaction was diluted with saturated aqueous NH$_4$Cl and EtOAc, the organic layer was extracted, washed with aqueous KOH and brine, dried with Na$_2$SO$_4$ and concentrated in vacuo and purified by silica gel chromatography (Hexane/EtOAc gradient). The product 2a was obtained in 76% (run 1) and 78% (run 2) yield.

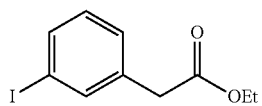

2a Prepared according to the General Procedure A from the corresponding neopentyl boronic ester (316 mg, 1.00 mmol, 2.00 equiv.) and mono-ethyl malonate (66.1 mg, 0.500 mmol, 1.00 equiv.) using Cu(OTf)2 (54.3 mg, 0.150 mmol, 0.300 equiv.), 71 h. Isolated in 83% yield after purification by column chromatography (15:1 Hexane/EtOAc) as a colorless oil.

$^1$H NMR (CDCl$_3$, 500 MHz) δ 7.65 (m, 1H), 7.61 (m, 1H), 7.26 (m, 1H), 7.06 (m, 1H), 4.16 (q, J=7.0 Hz, 2H), 3.55 (s, 2H), 1.26 (t, J=7.0 Hz, 3H);

$^{13}$C NMR (CDCl$_3$, 125 MHz) δ 171.1, 138.4, 136.5, 136.3, 130.3, 128.7, 94.5, 61.2, 40.9, 14.3;

HRMS (LCMS ESI): calcd for C$_{10}$H$_{11}$INaO$_2$ [M+Na]$^+$: 312.9696. Found 312.9696.

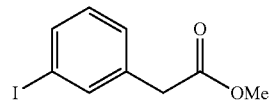 [SMILES: COC(=O)Cc1cccc(I)c1]

2b Prepared according to the General Procedure from the corresponding neopentyl boronic ester (316 mg, 1.00 mmol, 2.00 equiv.) and mono-methyl malonate (59.0 mg, 0.500 mmol, 1.00 equiv.) using Cu(OTf)$_2$ (54.3 mg, 0.150 mmol, 0.300 equiv.), 66 h. Isolated in 78% yield after purification by column chromatography (Hexane/EtOAc gradient) as a light yellow oil.

$^1$H NMR (CDCl$_3$, 700 MHz) δ 7.65 (m 1H), 7.61 (m, 1H), 7.25 (m, 1H) 7.06 (t, J=6.3 Hz, 1H), 3.70 (s 3H), 3.57 (s, 2H);

$^{13}$C NMR (CDCl$_3$, 176 MHz) δ 171.5, 138.4, 136.4, 136.3, 130.4, 128.7, 94.5, 52.3, 40.7;

HRMS (EI): calcd for C$_9$H$_9$IO$_2$ M$^+$: 275.9647. Found 275.9649.

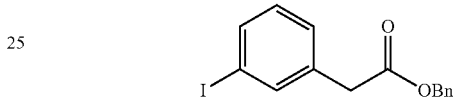

2c Prepared according to the General Procedure A from the corresponding neopentyl boronic ester (316 mg, 1.00 mmol, 2.00 equiv.) and mono-benzyl malonate (97.1 mg, 0.500 mmol, 1.00 equiv.) using Cu(OTf)$_2$ (54.3 mg, 0.150 mmol, 0.300 equiv.), 48 h. Isolated in 66% yield after purification by column chromatography (20:1 to 10:1 Hexane/EtOAc) as a colorless oil.

$^1$H NMR (CDCl$_3$, 500 MHz) δ 7.65 (m, 1H), 7.61 (m, 1H), 7.30-7.38 (m, 5H), 7.25 (m, 1H), 7.06 (m, 1H), 5.14 (s, 2H), 3.61 (s, 2H);

$^{13}$C NMR (CDCl$_3$, 125 MHz) δ 170.7, 138.3, 136.3, 136.1, 135.7, 130.3, 128.7, 128.6, 128.4, 128.2, 94.4, 66.9, 40.7;

HRMS (LCMS ESI): calcd for C$_{15}$H$_{13}$INaO$_2$ [M+Na]$^+$: 374.9852 Found 374.9854.

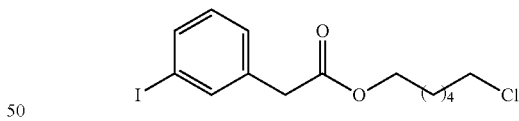

2d Prepared according to the General Procedure A from the corresponding neopentyl boronic ester (316 mg, 1.00 mmol, 2.00 equiv.) and mono-1-chlorohexyl malonate (120 mg, 0.500 mmol, 1.00 equiv.) using Cu(OTf)$_2$ (54.3 mg, 0.150 mmol, 0.300 equiv.), 60 h. Isolated in 93% yield after purification by column chromatography (40:1 to 5:1 Hexane/EtOAc) as a colorless oil.

$^1$H NMR (CDCl$_3$, 500 MHz) δ 7.65 (m, 1H), 7.61 (m, 1H), 7.25 (m, 1H), 7.06 (m, 1H), 4.10 (t, J=6.5 Hz, 2H), 3.55 (s, 2H), 3.52 (t, J=6.7 Hz, 2H), 1.78-1.74 (m, 2H), 1.66-1.61 (m, 2H), 1.46-1.42 (m, 2H), 1.36-1.31 (m, 2H);

$^{13}$C NMR (CDCl$_3$, 175 MHz) δ 171.0, 138.3, 136.4, 136.2, 130.3, 128.6, 94.4, 65.0, 45.0, 40.9, 32.5, 28.4, 26.5, 25.2;

HRMS (LCMS ESI): calcd for C$_{14}$H$_{18}$ClINaO$_2$ [M+Na]$^+$: 402.9932. Found 402.9932.

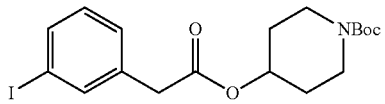 [SMILES: CC(C)(C)OC(=O)N1CCC(OC(=O)Cc2cccc(I)c2)CC1]

2e Prepared according to the General Procedure from the corresponding neopentyl boronic ester (316 mg, 1.00 mmol, 2.00 equiv.) and mono-4-NBoc piperidyl malonate (143.6 mg, 0.500 mmol, 1.00 equiv.) using Cu(OTf)$_2$ (54.3 mg, 0.150 mmol, 0.300 equiv.), 66 h. Isolated in 47% yield after purification by column chromatography (4:1 Hexane/EtOAc) as a colorless oil.

$^1$H NMR (CDCl$_3$, 700 MHz) δ 7.65 (m 1H), 7.61 (m, 1H), 7.25 (m, 1H) 7.06 (t, J=7.7 Hz, 1H), 4.94 (m, 1H), 3.62 (br, 2H), 3.55 (s, 2H), 3.23 (m, 2H), 1.81 (br, 2H), 1.58 (br, 2H), 1.46 (s, 9H);

$^{13}$C NMR (CDCl$_3$, 176 MHz) δ 170.3, 154.8, 138.3, 136.4, 136.3, 130.4, 128.6, 94.5, 79.9, 70.6, 41.2, 41.1 (br), 30.6, 28.6;

HRMS (LCMS ESI): calcd for C$_{18}$H$_{24}$INNaO$_4$ [M+Na]$^+$: 468.0642. Found 468.0641.

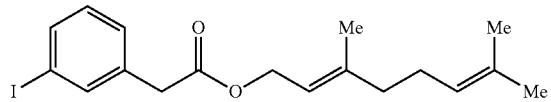 [SMILES: CC(C)=CCC/C(C)=C/COC(=O)Cc1cccc(I)c1]

2f Prepared according to the General Procedure from the corresponding neopentyl boronic ester (316 mg, 1.00 mmol, 2.00 equiv.) and mono-geranyl malonate (8:1 mixture of E/Z isomers, 120 mg, 0.500 mmol, 1.00 equiv.) using Cu(OTf)$_2$ (54.3 mg, 0.150 mmol, 0.300 equiv.), 73 h. Isolated in 45% yield after purification by column chromatography (Hexane/EtOAc gradient) as a colorless oil (mixture of E/Z isomers [8:1] as in the geraniol starting material):

$^1$H NMR (CDCl$_3$, 700 MHz) δ 7.65 (m, 1H), 7.60 (m, 1H), 7.25 (d, J=8.5 Hz, 1H) 7.05 (t, J=7.8 Hz, 1H), 5.33 (m, 1H), 5.08 (m, 1H), 4.62 (d, J=7.0 Hz, 2H, E isomer), 4.60 (d, J=7.3 Hz, 2H, Z isomer), 3.56 (s, 2H), 2.13-2.07 (m, 2H), 2.07-2.02 (m, 2H), 1.70 (m, 6H), 1.60 (s, 3H);

$^{13}$C NMR (CDCl$_3$, 176 MHz) δ 170.1, 142.9, 138.4, 136.5, 136.3, 132.0, 130.3, 128.7, 123.9, 118.1, 94.5, 62.1, 40.9, 40.0, 26.4, 25.8, 17.9, 16.7;

HRMS (LCMS ESI): calcd for C$_{18}$H$_{23}$INaO$_2$ [M+Na]$^+$: 421.0635. Found 421.0635.

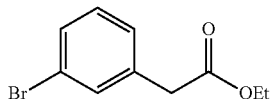 [SMILES: CCOC(=O)Cc1cccc(Br)c1]

2g Prepared according to the General Procedure A from the corresponding neopentyl boronic ester (268 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 72 h. Isolated in 82% yield after purification by column chromatography (15:1 Hexane/EtOAc) as a colorless oil. Spectroscopic data agreed with that reported.[12]

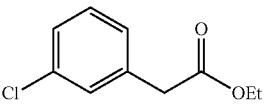

2h Prepared according to the General Procedure A from the corresponding neopentyl boronic ester (197 mg, 0.880 mmol, 2.00 equiv.) and mono-ethyl malonate (58.1 mg, 0.440 mmol, 1.00 equiv.) using Cu(OTf)$_2$ (47.7 mg, 0.132 mmol, 0.300 equiv.), 62 h. Isolated in 77% yield after purification by column chromatography (20:1 to 10:1 Hexane/EtOAc) as a colorless oil. Spectroscopic data agreed with that reported.[13]

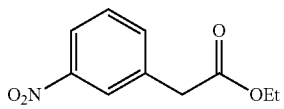 [SMILES: CCOC(=O)Cc1cccc([N+](=O)[O-])c1]

2i Prepared according to the General Procedure A from the corresponding neopentyl boronic ester (235 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 67 h. Isolated in 68% yield after purification by column chromatography (10:1 to 1:1 Hexane/EtOAc) as a colorless oil. Spectroscopic data agreed with that reported.[14]

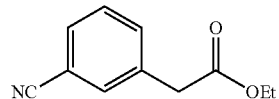 [SMILES: CCOC(=O)Cc1cccc(C#N)c1]

2j Prepared according to the General Procedure A from the corresponding neopentyl boronic ester (215 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 60 h. Isolated in 65% yield after purification by column chromatography (4:1 Hexane/EtOAc) as a light beige solid. Spectroscopic data agreed with that reported.[14]

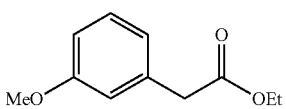 [SMILES: CCOC(=O)Cc1cccc(OC)c1]

2k Prepared according to the General Procedure A from the corresponding neopentyl boronic ester (220 mg, 1.00 mmol, 2.00 equiv.) and mono-ethyl malonate (66.1 mg, 0.500 mmol, 1.00 equiv.) using Cu(OTf)$_2$ (181 mg, 0.500 mmol, 1.00 equiv.), 50 h. Isolated in 67% yield after purification by column chromatography (50:1 to 4:1 Hexane/EtOAc) as a colorless oil. Spectroscopic data agreed with that reported.[14]

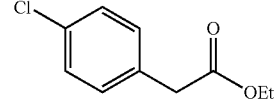

2l Prepared according to the General Procedure A from the corresponding neopentyl boronic ester (225 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 72 h. Isolated in 68% yield after purification by column chromatography (15:1 Hexane/EtOAc) as a colorless oil. Spectroscopic data agreed with that reported.[13]

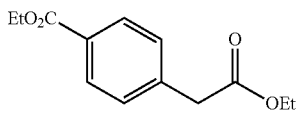 [SMILES: CCOC(=O)Cc1ccc(C(=O)OCC)cc1]

2m Prepared according to the General Procedure A from the corresponding neopentyl boronic ester (262 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 70 h. Isolated in 75% yield after purification by column chromatography (15:1 Hexane/EtOAc) as a colorless oil. Spectroscopic data agreed with that reported.[15]

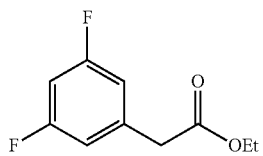

2n Prepared according to the General Procedure A from the corresponding neopentyl boronic ester (226 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 42 h. Isolated in 77% yield after purification by column chromatography (10:1 Hexane/EtOAc) as a colorless oil.

$^1$H NMR (CDCl$_3$, 500 MHz) δ 6.84-6.80 (m, 2H), 6.72 (m, 1H), 4.17 (q, J=7.2 Hz, 2H), 3.59 (s, 2H), 1.27 (t, J=7.1 Hz, 3H);

$^{13}$C NMR (CDCl$_3$, 125 MHz) δ 170.4, 163.0 (dd, J=249, 12.9 Hz), 137.6, 112.4, 102.7, 61.3, 41.0, 14.2;

$^{19}$F NMR (CDCl$_3$, 469 MHz) δ −110.0 (t, J=8.2 Hz);

HRMS (EI): calcd for C$_{10}$H$_{10}$O$_2$F$_2$ [M]$^+$: 200.0649. Found 200.0647.

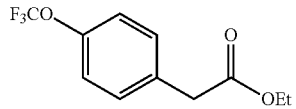 [SMILES: CCOC(=O)Cc1ccc(OC(F)(F)F)cc1]

2o Prepared according to the General Procedure A from the corresponding neopentyl boronic ester (274 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 60 h. Isolated in 60% yield after purification by column chromatography (50:1 to 4:1 Hexane/EtOAc) as a colorless oil. Spectroscopic data agreed with that reported.[15]

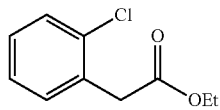 [SMILES: CCOC(=O)Cc1ccccc1Cl]

2p Prepared according to the General Procedure A from the corresponding neopentyl boronic ester (225 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 42 h. Isolated in 47% yield after purification by column chromatography (10:1 Hexane/EtOAc) as a colorless oil. Spectroscopic data agreed with that reported.[13]

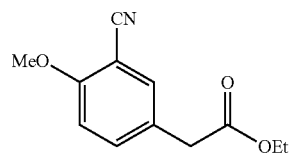 [SMILES: CCOC(=O)Cc1ccc(OC)c(C#N)c1]

2q Prepared according to the General Procedure A from the corresponding neopentyl boronic ester (245 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 62 h. Isolated in 69% yield after purification by column chromatography (2:1 Hexane/EtOAc) as a white solid.

$^1$H NMR (CDCl$_3$, 500 MHz) δ 7.46 (m, 2H), 6.92 (m, 1H), 4.15 (q, J=7.1 Hz, 2H), 3.92 (s, 3H), 3.55 (s, 2H), 1.26 (t, J=7.2 Hz, 3H);

$^{13}$C NMR (CDCl$_3$, 125 MHz) δ 170.9, 160.4, 135.4, 134.4, 126.8, 116.3, 111.5, 102.0, 61.2, 56.2, 39.9, 14.2;

HRMS (LCMS ESI): calcd for C$_{12}$H$_{13}$NNaO$_3$ [M+Na]$^+$: 242.0788. Found 242.0789.

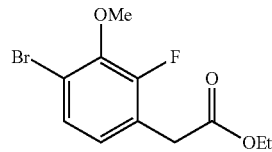 [SMILES: CCOC(=O)Cc1ccc(Br)c(OC)c1F]

2r Prepared according to the General Procedure A from the corresponding neopentyl boronic ester (317 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 62 h. Isolated in 52% yield after purification by column chromatography (10:1 Hexane/EtOAc) as a light yellow oil.

$^1$H NMR (CDCl$_3$, 500 MHz) δ 7.27 (m, 1H), 6.87 (m, 1H), 4.18 (q, J=7.1 Hz, 2H), 3.95 (s, 3H), 3.62 (s, 2H), 1.26 (t, J=7.2 Hz, 3H);

$^{13}$C NMR (CDCl$_3$, 125 MHz) δ 170.1, 154.7 (d, J=251 Hz), 145.5 (d, J=13 Hz), 127.8 (d, J=41 Hz), 126.2 (d, J=41 Hz), 122.7 (d, J=14.7 Hz), 116.4 (d, J=3.0 Hz), 61.5 (d, J=4.3 Hz), 61.3, 34.4 (d, J=3.6 Hz), 14.2;

$^{19}$F NMR (CDCl$_3$, 377 MHz) δ −130.6;

HRMS (LCMS ESI): calcd for C$_{11}$H$_{12}$BrFNaO$_3$ [M+Na]$^+$: 312.9846. Found 312.9842.

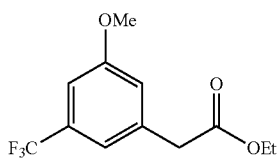 [SMILES: CCOC(=O)Cc1cc(OC)cc(C(F)(F)F)c1]

2s Prepared according to the General Procedure A from the corresponding neopentyl boronic ester (288 mg, 1.00 mmol, 2.00 equiv.) and mono-ethyl malonate (66.1 mg, 0.500 mmol, 1.00 equiv.) using Cu(OTf)2 (54.3 mg, 0.150 mmol, 0.300 equiv.), 48 h. Isolated in 79% yield after purification by column chromatography (10:1 Hexane/EtOAc) as a colorless oil.

$^1$H NMR (CDCl$_3$, 500 MHz) δ 7.13 (m, 1H), 7.02 (m, 2H), 4.17 (q, J=7.0 Hz, 2H), 3.84 (s, 3H), 3.63 (s, 2H), 1.26 (t, J=7.1 Hz, 3H);

$^{13}$C NMR (CDCl$_3$, 125 MHz) δ 170.8, 159.9, 136.5, 132.0 (q, J=34 Hz), 123.9 (q, J=271 Hz), 118.6, 118.4, 109.5, 61.2, 55.5, 41.2, 14.2;

$^{19}$F NMR (CDCl$_3$, 377 MHz) δ −62.7;

HRMS (EI): calcd for C$_{12}$H$_{13}$F$_3$O$_3$ [M]$^+$: 262.0817. Found 262.0814.

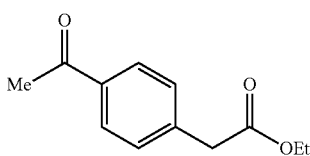 [SMILES: CCOC(=O)Cc1ccc(C(C)=O)cc1]

2t Prepared according to the General Procedure A from the corresponding neopentyl boronic ester (232 mg, 1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 67 h. Isolated in 75% yield after purification by column chromatography (6:1 to 1:1 Hexane/EtOAc) as a white solid. Spectroscopic data agreed with that reported.[15]

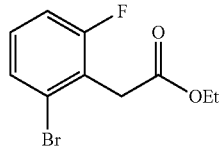 [SMILES: CCOC(=O)Cc1c(F)cccc1Br]

2u Prepared according to the General Procedure A from the corresponding neopentyl boronic ester (430 mg, 1.50 mmol, 3.00 equiv.) and mono-ethyl malonate (66.1 mg, 0.500 mmol, 1.00 equiv.) using Cu(OTf)$_2$ (54.3 mg, 0.150 mmol, 0.300 equiv.), 61 h. Isolated in 54% yield after purification by column chromatography (30:1 to 4:1 Hexane/EtOAc) as a colorless oil.

$^1$H NMR (CDCl$_3$, 500 MHz) δ 7.38 (m, 1H), 7.15 (m, 1H), 7.04 (m, 1H), 4.19 (q, J=7.4 Hz, 2H), 3.86 (d, J=1.9 Hz, 2H), 1.27 (t, J=7.2 Hz, 3H);

$^{13}$C NMR (CDCl$_3$, 125 MHz) δ 169.6, 161.4 (d, J=244 Hz), 129.6 (d, J=9.4 Hz), 128.4 (d, J=4.4 Hz), 126.0 (d, J=4.4 Hz), 123.0 (d, J=18.9 Hz), 114.6 (d, J=23.4 Hz), 61.3, 34.7, 14.2;

$^{19}$F NMR (CDCl$_3$, 469 MHz) δ −111.3;

HRMS (LCMS ESI): calcd for C$_{10}$H$_{10}$BrFNaO$_2$ [M+Na]$^+$: 282.9740. Found 282.9743.

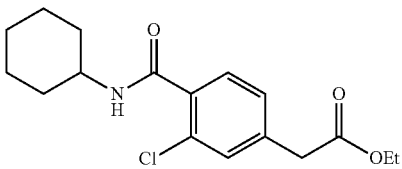 [SMILES: CCOC(=O)Cc1ccc(C(=O)NC2CCCCC2)c(Cl)c1]

2w Prepared according to the General Procedure A from the corresponding neopentyl boronic ester (262 mg, 0.750 mmol, 1.50 equiv.) and mono-ethyl malonate (66.1 mg, 0.500 mmol, 1.00 equiv.) using Cu(OTf)2 (90.4 mg, 0.250 mmol, 0.500 equiv.), 54 h. Isolated in 55% yield after purification by column chromatography (4:1 to 1:1 Hexane/EtOAc) as a white solid.

$^1$H NMR (CDCl$_3$, 500 MHz) δ 7.59 (m, 1H), 7.31 (m, 1H), 7.21 (m, 1H), 6.08 (br, 1H), 4.14 (q, J=7.1 Hz, 2H), 3.99 (m, 1H), 3.58 (s, 2H), 2.05-1.97 (m, 2H), 1.77-1.68 (m, 2H), 1.63 (m, 1H), 1.48-1.36 (m, 2H), 1.31-1.15 (m, 6H);

$^{13}$C NMR (CDCl$_3$, 125 MHz) δ 170.6, 165.4, 137.7, 134.4, 131.0, 130.7, 130.4, 128.2, 61.3, 49.0, 40.8, 33.0, 25.6, 24.8, 14.3;

HRMS (LCMS ESI): calcd for C$_{17}$H$_{22}$ClNNaO$_3$ [M+Na]$^+$: 346.1180. Found 346.1185.

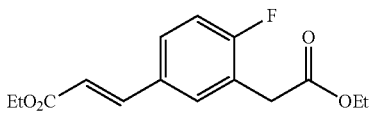

2v Prepared according to the General Procedure A from the corresponding neopentyl boronic ester (230 mg, 0.750 mmol, 1.50 equiv.) and mono-ethyl malonate (66.1 mg, 0.500 mmol, 1.00 equiv.) using Cu(OTf)$_2$ (54.3 mg, 0.150 mmol, 0.300 equiv.), 60 h. Isolated in 55% yield after purification by column chromatography (30:1 to 4:1 Hexane/EtOAc) as a colorless oil.

$^1$H NMR (CDCl$_3$, 500 MHz) δ 7.62 (d, J=16 Hz, 1H), 7.45-7.42 (m, 2H), 7.07 (m, 1H), 6.35 (d, J=16 Hz, 1H), 4.26 (q, J=7.2 Hz, 2H), 4.18 (q, J=7.2 Hz, 2H), 3.67 (s, 2H), 0.33 (t, J=7.1 Hz, 3H), 1.27 (t, J=7.1 Hz, 3H);

$^{13}$C NMR (CDCl$_3$, 125 MHz) δ 170.3, 166.9, 162.2 (d, J=260 Hz), 143.2, 131.4, 130.9, 128.9, 122.3, 118.3, 116.2, 61.3, 60.6, 34.5, 14.4, 14.2;

$^{19}$F NMR (CDCl$_3$, 469 MHz) δ −113.9;

HRMS (LCMS ESI): calcd for C$_{15}$H$_{17}$FNaO$_4$ [M+Na]$^+$: 303.1003. Found 303.1005.

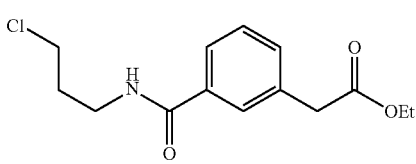 [SMILES: CCOC(=O)Cc1cccc(C(=O)NCCCCl)c1]

2x Prepared according to the General Procedure A from the corresponding neopentyl boronic ester (232 mg, 0.750 mmol, 1.50 equiv.) and mono-ethyl malonate (66.1 mg, 0.500 mmol, 1.00 equiv.) using Cu(OTf)$_2$ (90.4 mg, 0.250 mmol, 0.500 equiv.), 61 h. Isolated in 70% yield after purification by column chromatography (3:2 to 2:3 Hexane/EtOAc) as a colorless oil.

$^1$H NMR (CDCl$_3$, 500 MHz) δ 7.69 (m, 1H), 7.65 (m, 1H), 7.45-7.38 (m, 2H), 6.33 (br, 1H), 4.16 (q, J=7.2 Hz, 2H), 3.68-3.60 (m, 6H), 2.13 (quint, J=6.4 Hz, 2H), 1.26 (t, J=7.1 Hz, 3H);

$^{13}$C NMR (CDCl$_3$, 125 MHz) δ 171.2, 167.5, 134.8 (2C), 132.6, 128.9, 127.9, 125.6, 61.1, 42.7, 41.2, 37.7, 32.1, 14.2;

HRMS (LCMS ESI): calcd for C$_{14}$H$_{18}$ClNNaO$_3$ [M+Na]$^+$: 306.0867. Found 306.0866.

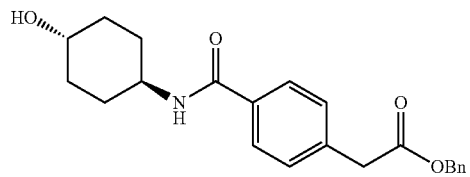 [SMILES: O=C(Cc1ccc(C(=O)N[C@H]2CC[C@H](O)CC2)cc1)OCc1ccccc1]

2y Prepared according to the General Procedure A from the corresponding neopentyl boronic ester (218 mg, 0.750 mmol, 1.50 equiv.) and mono-benzyl malonate (66.1 mg, 0.500 mmol, 1.00 equiv.) using Cu(OTf)$_2$ (90.4 mg, 0.250 mmol, 0.500 equiv.), 48 h. Crude NMR shows 54% NMR yield using trimethoxybenzene as internal standard. Isolated in 39% yield after purification by column chromatography (6% to 7% MeOH/CH$_2$Cl$_2$) as a white solid.

$^1$H NMR (CDCl$_3$, 500 MHz) δ 7.71-7.69 (m, 2H), 7.37-7.30 (m, 7H), 5.85 (br, 1H), 5.13 (s, 2H), 3.97 (m, 1H), 3.71 (s, 2H), 3.66 (m, 1H), 2.16-2.09 (m, 2H), 2.06-2.0 (m, 2H), 1.6-1.4 (m, 3H), 1.35-1.25 (m, 2H);

$^{13}$C NMR (CDCl$_3$, 125 MHz) δ 170.8, 166.6, 137.4, 135.7, 133.8, 129.6, 128.6, 128.4, 128.3, 127.2, 69.9, 66.9, 48.1, 41.2, 34.1, 31.0;

HRMS (LCMS ESI): calcd for C$_{22}$H$_{25}$NNaO$_4$ [M+Na]$^+$: 390.1676. Found 390.1674.

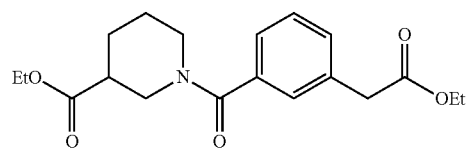 [SMILES: CCOC(=O)Cc1cccc(C(=O)N2CCCC(C(=O)OCC)C2)c1]

2z Prepared according to the General Procedure A from the corresponding neopentyl boronic ester (280 mg, 0.750 mmol, 1.50 equiv.) and mono-ethyl malonate (66.1 mg, 0.500 mmol, 1.00 equiv.) using Cu(OTf)$_2$ (54.3 mg, 0.150 mmol, 0.300 equiv.), 67 h. Isolated in 63% yield after purification by column chromatography (4:1 Hexane/EtOAc to EtOAc) as a colorless oil.

$^1$H NMR (DMSO-d$_6$, 400 MHz, 120° C.) δ 7.34 (m, 1H), 7.30 (m, 1H), 7.20-7.25 (m, 2H), 4.01-4.11 (m, 4H), 3.98 (m, 1H), 3.67 (m, 1H), 3.64 (s, 2H), 3.22 (dd, J=10 Hz, 13.2 Hz, 1H), 3.09 (m, 1H), 2.51 (m, 1H), 1.95 (m, 1H), 1.61-1.72 (m, 2H), 1.45 (m, 1H), 1.12-1.17 (m, 6H);

$^{13}$C NMR (DMSO-d$_6$, 100 MHz, 120° C.) δ 171.7, 169.9, 168.6, 135.9, 134.1, 129.4, 127.6, 126.8, 124.5, 59.6, 59.3, 45.3, 44.2, 40.2, 26.0, 23.1, 13.3, 13.2 (one peak missing, obscured by solvent signal);

HRMS (LCMS ESI): calcd for C$_{19}$H$_{25}$NNaO$_5$ [M+Na]$^+$: 370.1625. Found 370.1631.

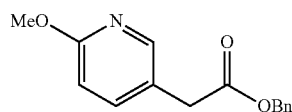 [SMILES: COc1ccc(CC(=O)OCc2ccccc2)cn1]

3a Prepared according to the General Procedure from the corresponding neopentyl boronic ester (165.8 mg, 0.75 mmol, 1.50 equiv.) and mono-benzyl malonate (97.1 mg, 0.500 mmol, 1.00 equiv.) using Cu(OTf)$_2$ (90.4 mg, 0.250 mmol, 0.500 equiv.), 46 h. Isolated in 68% yield after purification by column chromatography (4:1 Hexane/EtOAc) as a colorless oil.

$^1$H NMR (CDCl$_3$, 700 MHz) δ 8.05 (d, J=2.1 Hz, 1H), 7.52 (dd, J=9.1, 2.1 Hz, 1H), 7.29-7.38 (m, 5H), 6.72 (d, J=9.1 Hz, 1H), 5.14 (s, 2H), 3.92 (s, 3H), 3.59 (s, 2H);

$^{13}$C NMR (CDCl$_3$, 176 MHz) δ 171.2, 163.6, 147.1, 139.8, 135.8, 128.7, 128.5, 128.4, 122.4, 110.9, 67.0, 53.6, 37.7;

HRMS (LCMS ESI): calcd for C$_{15}$H$_{16}$NO$_3$ [M+H]$^+$: 258.1125. Found 258.1127.

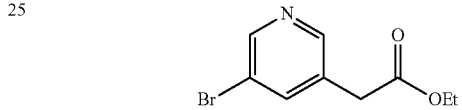

3b Prepared according to the General Procedure from the corresponding neopentyl boronic ester (202.4 mg, 0.75 mmol, 1.50 equiv.) and mono-ethyl malonate (66.1 mg, 0.500 mmol, 1.00 equiv.) using Cu(OTf)$_2$ (90.4 mg, 0.250 mmol, 0.500 equiv.), 70 h. Isolated in 47% yield after purification by column chromatography (2:1 Hexane/EtOAc) as a colorless oil.

$^1$H NMR (CDCl$_3$, 700 MHz) δ 8.60 (br s, 1H), 8.44 (br s, 1H), 7.81 (t, J=2.1 Hz, 1H), 4.18 (q, J=7.0 Hz, 2H), 3.60 (s, 2H), 1.27 (t, J=7.0 Hz, 3H);

$^{13}$C NMR (CDCl$_3$, 176 MHz) δ 170.2, 149.8, 148.6, 139.6, 131.6, 120.8, 61.6, 38.1, 14.3;

HRMS (LCMS ESI): calcd for C$_9$H$_{11}$BrNO$_2$ [M+H]$^+$: 243.9968. Found 243.9965.

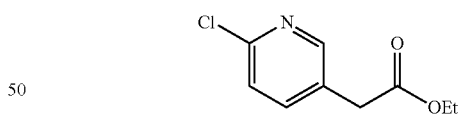

3c Prepared according to the General Procedure from the corresponding neopentyl boronic ester (169.1 mg, 0.75 mmol, 1.50 equiv.) and mono-ethyl malonate (66.1 mg, 0.500 mmol, 1.00 equiv.) using Cu(OTf)$_2$ (90.4 mg, 0.250 mmol, 0.500 equiv.), 70 h. Isolated in 67% yield after purification by column chromatography (4:1 Hexane/EtOAc) as a colorless oil.

$^1$H NMR (CDCl$_3$, 700 MHz) δ 8.29 (s, 1H), 7.62 (dd, J=8.4, 3.2 Hz, 1H), 7.30 (d, J=8.4 Hz, 1H) 4.17 (q, J=7.0 Hz, 2H), 3.60 (s, 2H), 1.26 (t, J=7.2 Hz, 3H);

$^{13}$C NMR (CDCl$_3$, 176 MHz) δ 170.4, 150.5, 150.2, 139.8, 128.9, 124.2, 61.5, 37.8, 14.3;

HRMS (LCMS ESI): calcd for C$_9$H$_{11}$ClNO$_2$ [M+H]$^+$: 200.0473. Found 200.0469.

3d Prepared according to the General Procedure from the corresponding neopentyl boronic ester (194.3 mg, 0.75 mmol, 1.50 equiv.) and mono-ethyl malonate (66.1 mg, 0.500 mmol, 1.00 equiv.) using Cu(OTf)$_2$ (90.4 mg, 0.25 mmol, 0.500 equiv.), 44 h. Isolated in 77% yield after purification by column chromatography (4:1 Hexane/EtOAc) as a colorless oil.

$^1$H NMR (CDCl$_3$, 700 MHz) δ ⊛ 8.64 (s, 1H), 7.83 (m, 1H), 7.66 (d, J=8.4 Hz, 1H), 4.19 (q, J=7.0 Hz, 2H), 3.71 (s, 2H), 1.27 (t, J=7.0 Hz, 3H);

$^{13}$C NMR (CDCl$_3$, 176 MHz) δ 170.0, 150.7, 147.2 (q, J=34.8 Hz), 138.3, 133.3, 121.7 (q, J=274.5 Hz) 120.4, 61.7, 38.4, 14.3;

$^{19}$F NMR (CDCl$_3$, 377 MHz) δ ⊛ −68.00;

HRMS (LCMS ESI): calcd for C$_{10}$H$_{11}$F$_3$NO$_2$ [M+H]$^+$: 234.0736. Found 234.0737.

3e Prepared according to the General Procedure from the corresponding neopentyl boronic ester (156.8 mg, 0.75 mmol, 1.50 equiv.) and mono-benzyl malonate (97.1 mg, 0.500 mmol, 1.00 equiv.) using Cu(OTf)$_2$ (90.4 mg, 0.250 mmol, 0.500 equiv.), 53 h. Isolated in 53% yield after purification by column chromatography (4:1 Hexane/EtOAc) as a colorless oil.

$^1$H NMR (CDCl$_3$, 700 MHz) δ ⊛ 8.15 (d, J=4.9 Hz, 1H), 7.71 (m, 1H), 7.31-7.38 (m, 5H), 7.16 (m, 1H), 5.17 (s, 2H), 3.72 (s, 2H);

$^{13}$C NMR (CDCl$_3$, 176 MHz) δ 169.8, 162.0 (d, J=238.8 Hz), 146.8 (d, J=14.8 Hz), 142.0 (d, J=4.8 Hz), 135.5, 128.7, 128.5, 128.4, 121.6 (d, J=4.4 Hz), 116.6 (d, J=31.1 Hz), 67.2, 34.3 (d, J=1.9 Hz);

$^{19}$F NMR (CDCl$_3$, 376 MHz) ⊛ δ ⊛ −71.56;

HRMS (LCMS ESI): calcd for C$_{14}$H$_{13}$FNO$_2$ [M+H]$^+$: 246.0925. Found 246.0921.

3f Prepared according to the General Procedure from the corresponding neopentyl boronic ester (180.8 mg, 0.75 mmol, 1.50 equiv.) and mono-benzyl malonate (97.1 mg, 0.500 mmol, 1.00 equiv.) using Cu(OTf)$_2$ (90.4 mg, 0.250 mmol, 0.500 equiv.), 51 h. Isolated in 73% yield after purification by column chromatography (Hexane/EtOAc gradient with 6% NEt$_3$) as a white solid.

$^1$H NMR (CDCl$_3$, 700 MHz) δ ⊛ 8.85 (d, J=2.1 Hz, 1H), 8.10 (d, J=8.4 Hz, 1H), 8.07 (br s, 1H), 7.78 (d, J=8.4 Hz, 1H), 7.70 (m, 1H) 7.55 (m, 1H), 7.30-7.37 (m, 5H), 5.17 (s, 2H), 3.86 (s, 2H);

$^{13}$C NMR (CDCl$_3$, 176 MHz) δ 170.7, 151.8, 147.5, 136.0, 135.6, 129.5, 129.4, 128.8, 128.6, 128.5, 128.0, 127.7, 127.0, 126.9, 67.2, 38.8;

HRMS (LCMS ESI): calcd for C$_{18}$H$_{16}$NO$_2$ [M+H]$^+$: 278.1176. Found 278.1171.

3g Prepared according to the General Procedure, with the modification of using 1,2-DCE as the solvent, from the corresponding neopentyl boronic ester (144.0 mg, 0.75 mmol, 1.50 equiv.) and mono-benzyl malonate (97.1 mg, 0.500 mmol, 1.00 equiv.) using Cu(OTf)$_2$ (90.4 mg, 0.250 mmol, 0.500 equiv.), 31 h. The solvent was removed in vacuo. The crude residue was purified by silica gel chromatography (25:1 DCM/MeOH). Isolated in 61% yield as a colorless oil.

$^1$H NMR (CDCl$_3$, 700 MHz) δ ⊛ 9.14 (s, 1H), 8.680 (s, 2H), 7.38-7.32 (m, 5H), 5.16 (s, 2H), 3.67 (s, 2H);

$^{13}$C NMR (CDCl$_3$, 176 MHz) δ 170.0, 157.8, 157.5, 135.3, 128.8, 128.7, 128.5, 127.9, 67.5, 36.0;

HRMS (LCMS ESI): calcd for C$_{13}$H$_{13}$N$_2$O$_2$ [M+H]$^+$: 229.0972. Found 229.0972.

3h Prepared according to the General Procedure from the corresponding neopentyl boronic ester (166.5 mg, 0.75 mmol, 1.50 equiv.) and mono-benzyl malonate (97.1 mg, 0.500 mmol, 1.00 equiv.) using Cu(OTf)2 (90.4 mg, 0.250 mmol, 0.500 equiv.), 48 h. Isolated in 65% yield after purification by column chromatography (1:1 Hexane/EtOAc) as a colorless oil.

$^1$H NMR (CDCl$_3$, 700 MHz) δ ⊛ 8.44 (s, 2H), 7.32-7.37 (m, 5H), 5.15 (s, 2H), 4.00 (s, 3H), 3.59 (s, 2H);

$^{13}$C NMR (CDCl$_3$, 176 MHz) δ ⊛ 170.3, 165.1, 159.8, 135.4, 128.8, 128.7, 128.5, 120.8, 67.4, 55.1, 35.1;

HRMS (LCMS ESI): calcd for C$_{14}$H$_{15}$N$_2$O$_3$ [M+H]$^+$: 259.1077. Found 259.1080.

3i Prepared according to the General Procedure from the corresponding neopentyl boronic ester (169.9 mg, 0.75 mmol, 1.50 equiv.) and mono-benzyl malonate (97.1 mg, 0.500 mmol, 1.00 equiv.) using Cu(OTf)$_2$ (90.4 mg, 0.250 mmol, 0.500 equiv.), 48 h. Isolated in 53% yield after purification by column chromatography (10:1 CH$_2$Cl$_2$/Et$_2$O) as a pale yellow solid.

$^1$H NMR (CDCl$_3$, 700 MHz) δ ⊛ 8.57 (s, 2H), 7.32-7.39 (m, 5H), 5.17 (s, 2H), 3.67 (s, 2H);

$^{13}$C NMR (CDCl$_3$, 176 MHz) δ 169.3, 160.6, 160.2, 135.1, 128.9, 128.9, 128.6, 126.4, 67.7, 35.2;

HRMS (LCMS ESI): calcd for $C_{13}H_{12}ClN_2O_2[M+H]^+$: 263.0582. Found 263.0578.

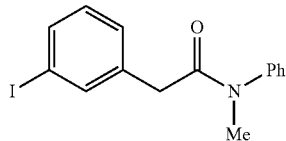 [SMILES: CN(C(=O)Cc1cccc(I)c1)c1ccccc1]

4a Prepared according to the General Procedure A from the corresponding neopentyl boronic ester (316 mg, 1.00 mmol, 2.00 equiv.) and 3-(methyl(phenyl)amino)-3-oxopropanoic acid (96.6 mg, 0.500 mmol, 1.00 equiv.) using $Cu(OTf)_2$ (54.3 mg, 0.150 mmol, 0.300 equiv.), 61 h. Isolated in 84% yield after purification by column chromatography (4:1 to 2:1 Hexane/EtOAc) as a colorless oil.

$^1$H NMR (CDCl$_3$, 500 MHz) δ 7.52 (m, 1H), 7.44-7.35 (m, 3H), 7.32 (m, 1H), 7.12-7.10 (m, 2H), 7.06 (m, 1H), 6.97 (m, 1H), 3.39 (s, 2H), 3.27 (s, 3H);

$^{13}$C NMR (CDCl$_3$, 125 MHz) δ 170.3, 143.8, 138.1, 137.7, 135.7, 130.0, 129.8, 128.4, 128.2, 127.7, 94.2, 40.6, 37.7;

HRMS (LCMS ESI): calcd for $C_{15}H_{14}INNaO [M+Na]^+$: 374.0012. Found 374.0015.

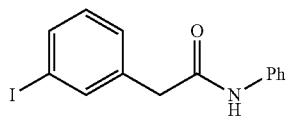 [SMILES: O=C(Cc1cccc(I)c1)Nc1ccccc1]

4b Prepared according to the General Procedure A from the corresponding neopentyl boronic ester (237 mg, 0.750 mmol, 1.50 equiv.) and 3-oxo-3-(phenylamino)propanoic acid (89.6 mg, 0.500 mmol, 1.00 equiv.) using $Cu(OTf)_2$ (54.3 mg, 0.150 mmol, 0.300 equiv.), 63 h. Isolated in 43% yield after purification by column chromatography (6:1 to 4:1 Hexane/EtOAc) as a white solid.

$^1$H NMR (CDCl$_3$, 500 MHz) δ 7.72 (m, 1H), 7.69 (m, 1H), 7.48-7.44 (m, 2H), 7.36-7.30 (m, 3H), 7.17-7.10 (m, 3H), 3.68 (s, 2H);

$^{13}$C NMR (CDCl$_3$, 125 MHz) δ 168.2, 138.4, 137.5, 136.8, 136.7, 130.8, 129.1, 128.7, 124.7, 120.0, 95.0, 44.2;

HRMS (LCMS ESI): calcd for $C_{14}H_{12}INNaO [M+Na]^+$: 359.9856. Found 359.9858.

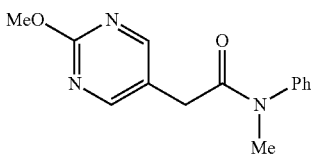 [SMILES: COc1ncc(CC(=O)N(C)c2ccccc2)cn1]

4c Prepared according to the General Procedure from the corresponding neopentyl boronic ester (166.5 mg, 0.75 mmol, 1.50 equiv.) and 3-(methyl(phenyl)amino)-3-oxopropanoic acid (96.6 mg, 0.500 mmol, 1.00 equiv.) using $Cu(OTf)_2$ (90.4 mg, 0.150 mmol, 0.500 equiv.), 43 h. Isolated in 49% yield after purification by column chromatography (1:4 Hexane/EtOAc) as a white solid.

$^1$H NMR (CDCl$_3$, 700 MHz) δ 8.23 (s, 2H), 7.46-7.48 (m, 2H), 7.40-7.42 (m, 1H), 7.18 (d, J=7.7 Hz, 2H), 3.97 (s, 3H), 3.33 (s, 2H), 3.28 (s, 3H);

$^{13}$C NMR (CDCl$_3$, 176 MHz) δ 169.7, 164.8, 159.7, 143.6, 130.3, 128.6, 127.6, 122.2, 55.0, 37.8, 34.8;

HRMS (LCMS ESI): calcd for $C_{14}H_{16}N_3O_2 [M+H]^+$: 258.1237. Found 258.1237.

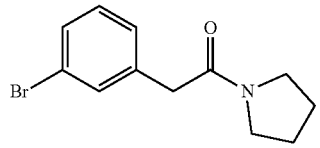 [SMILES: O=C(Cc1cccc(Br)c1)N1CCCC1]

4d Prepared according to the General Procedure A from the corresponding neopentyl boronic ester (269 mg, 1.00 mmol, 2.00 equiv.) and 3-oxo-3-(pyrrolidin-1-yl)propanoic acid (78.6 mg, 0.500 mmol, 1.00 equiv.) using $Cu(OTf)_2$ (54.3 mg, 0.150 mmol, 0.300 equiv.), 70 h. Isolated in 58% yield after purification by column chromatography (0% to 10% MeOH/EtOAc) as a light yellow oil.

$^1$H NMR (CDCl$_3$, 400 MHz) δ 7.42 (m, 1H), 7.35 (m, 1H), 7.22-7.12 (m, 2H), 3.59 (s, 2H), 3.48-3.39 (m, 4H), 1.95-1.79 (m, 4H);

$^{13}$C NMR (CDCl$_3$, 125 MHz) δ 168.6, 137.2, 132.0, 130.0, 129.8, 127.7, 122.5, 46.9, 46.1, 14.6, 26.2, 24.4;

HRMS (LCMS ESI): calcd for $C_{12}H_{14}BrNNaO [M+Na]^+$: 290.0151. Found 290.0155.

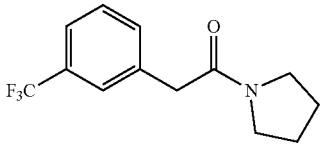 [SMILES: O=C(Cc1cccc(C(F)(F)F)c1)N1CCCC1]

4e Prepared according to the General Procedure A from the corresponding neopentyl boronic ester (258 mg, 1.00 mmol, 2.00 equiv.) and 3-oxo-3-(pyrrolidin-1-yl)propanoic acid (78.6 mg, 0.500 mmol, 1.00 equiv.) using $Cu(OTf)_2$ (54.3 mg, 0.150 mmol, 0.300 equiv.), 72 h. Isolated in 66% yield after purification by column chromatography (EtOAc) as a light yellow solid.

$^1$H NMR (CDCl$_3$, 500 MHz) δ 7.52-7.49 (m, 3H), 7.43 (m, 1H), 3.70 (s, 2H), 3.50 (t, J=7.0 Hz, 2H), 3.45 (t, J=6.8 Hz, 2H), 1.96 (quint, J=6.8 Hz, 2H), 1.86 (quint, J=7.0 Hz, 2H);

$^{13}$C NMR (CDCl$_3$, 125 MHz) δ 168.6, 136.0, 132.7, 130.8 (q, J=32 Hz), 129.0, 125.9, 124.1 (q, J=272 Hz), 123.7, 47.0, 46.1, 41.7, 26.2, 24.4;

$^{19}$F NMR (CDCl$_3$, 377 MHz) δ −62.6;

HRMS (LCMS ESI): calcd for $C_{13}H_{14}F_3NNaO [M+Na]^+$: 280.0920. Found 280.0919.

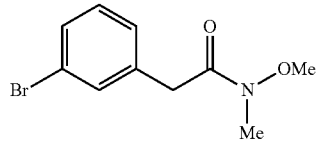 [SMILES: CON(C)C(=O)Cc1cccc(Br)c1]

4f Prepared according to the General Procedure A from the corresponding neopentyl boronic ester (269 mg, 1.00 mmol, 2.00 equiv.) and 3-(methoxy(methyl)amino)-3-oxopropanoic acid (73.6 mg, 0.500 mmol, 1.00 equiv.) using $Cu(OTf)_2$ (54.3 mg, 0.150 mmol, 0.300 equiv.), 68 h. Isolated in 70% yield after purification by column chromatography (4:1 to 1:1 Hexane/EtOAc) as a light yellow oil.

$^1$H NMR (CDCl$_3$, 400 MHz) δ 7.44 (m, 1H), 7.36 (m, 1H), 7.23-7.13 (m, 2H), 3.72 (s, 2H), 3.62 (s, 3H), 3.18 (s, 3H);

$^{13}$C NMR (CDCl$_3$, 125 MHz) δ 171.5, 137.1, 132.3, 129.92, 129.89, 128.0, 122.4, 61.3, 38.7, 32.2;

HRMS (LCMS ESI): calcd for C$_{10}$H$_{12}$BrNNaO$_2$ [M+Na]$^+$: 279.9944. Found 279.9949.

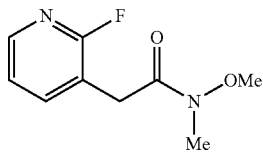 [SMILES: CON(C)C(=O)Cc1cccnc1F]

4g Prepared according to the General Procedure from the corresponding neopentyl boronic ester (159.8 mg, 0.75 mmol, 1.50 equiv.) and 3-(methoxy(methyl)amino)-3-oxopropanoic acid (73.6 mg, 0.500 mmol, 1.00 equiv.) using Cu(OTf)$_2$ (90.4 mg, 0.250 mmol, 0.500 equiv.), 48 h. Isolated in 51% yield after purification by column chromatography (Hexane/EtOAc gradient with 1% NEt3) as a colorless oil.

$^1$H NMR (CDCl$_3$, 700 MHz) δ 8.12 (d, J=3.5 Hz, 1H), 7.74 (t, J=8.1 Hz, 1H), 7.15-7.17 (m, 1H), 3.80 (s, 2H), 3.73 (s, 3H), 3.22 (s, 3H);

$^{13}$C NMR (CDCl$_3$, 176 MHz) δ 170.3, 161.2 (d, J=237.7 Hz), 146.3 (d, J=15.0 Hz), 142.3 (d, J=5.1 Hz), 121.6 (d, J=3.7 Hz), 117.4 (d, J=31.0 Hz), 61.4, 32.3, 31.8;

$^{19}$F NMR (CDCl$_3$, 376 MHz) −72.52;

HRMS (LCMS ESI): calcd for C$_9$H$_{12}$FN$_2$O$_2$[M+H]$^+$: 199.0877. Found 199.0879.

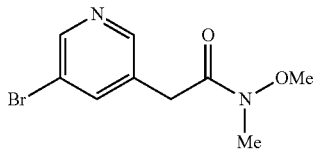 [SMILES: CON(C)C(=O)Cc1cncc(Br)c1]

4h Prepared according to the General Procedure from the corresponding neopentyl boronic ester (202.4 mg, 0.75 mmol, 1.50 equiv.) and 3-(methoxy(methyl)amino)-3-oxopropanoic acid (73.6 mg, 0.500 mmol, 1.00 equiv.) using Cu(OTf)$_2$ (90.4 mg, 0.250 mmol, 0.500 equiv.), 44 h. Isolated in 43% yield after purification by column chromatography (Hexane/EtOAc gradient with 1% NEt3) as a colorless oil.

$^1$H NMR (CDCl$_3$, 700 MHz) δ 8.57 (d, J=2.1 Hz, 1H), 8.42 (s, 1H), 7.82 (m, 1H), 3.75 (s, 2H) 3.70 (s, 3H), 3.21 (s, 3H);

$^{13}$C NMR (CDCl$_3$, 176 MHz) δ 170.7, 149.6, 148.8, 139.8, 132.4, 120.7, 61.6, 35.9, 32.5;

HRMS (LCMS ESI): calcd for C$_9$H$_{12}$BrN$_2$O$_2$[M+H]$^+$: 259.0077. Found 259.0079.

IV. ADDITIONAL INFORMATION, GUIDELINES AND TROUBLESHOOTING TIPS

1. Under the standard conditions with moderately electron-rich, electron-neutral or moderately electron-poor (hetero)aromatics, neopentyl boronic esters provide superior results than pinacol boronic esters largely due to enhanced reaction rates. Aryl boron partners prone to protodeborylation can be coupled with higher yields as pinacol esters.

2. The kinetic profile of most reactions show an induction period, followed by roughly zero-order kinetics.

3. Reactions that have a high malonate half ester to Cu ratio will proceed sluggishly. In cases where stoichiometry dictates an excess of the malonate half ester (ie, the aryl boron partner is the limiting reagent), increased Cu loadings are generally required to provide more efficient reactivity.

4. Background oxidative degradation of the malonate half esters occur slowly over a period of 2-3 days. As such, sluggish reactions will generally reach high conversions of malonate half-esters.

Figure 7A:
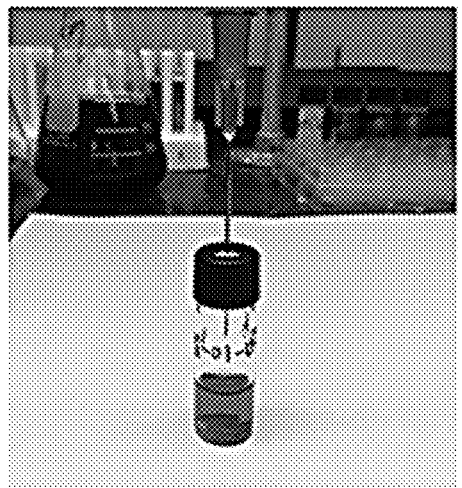
FIG. 7A-C depicts optimal reaction setups that allow reactions to reach completion between 24-72 h, particularly in respect of a reaction carried out on a 0.2 mmol scale in a 0.5 dram vial (FIG. 7A); on a 0.5 mmol scale in a 1 dram vial (FIG. 7B); and, on a 7 mmol scale in a 50 mL flask (FIG. 7C).
Figure 7B:
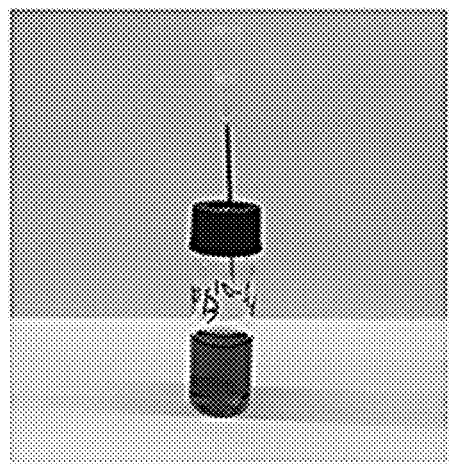
Figure 7C:
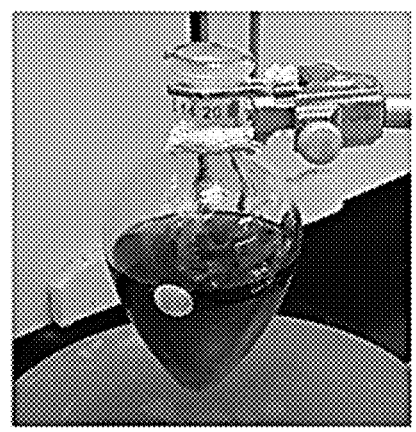

5. Reactions are sensitive to the reaction volume to vial size ratio. Reactions with large vial headspace or with an open cap will proceed with faster rates (high conversions in <12 h) but can result in increased side-product formation. Reactions with very little vial headspace will proceed with slower rates and require long reaction times (>5 days). We attribute these observations to the importance of balancing oxygen concentration. Reactions can be set up using a dry air balloon to exclude moisture. The use of drying agents, such as molecular sieves or anhydrous metal sulfates is not recommended. Optimal reaction setups as depicted in FIG. 7A-C, allow reactions to reach completion between 24-72 h. In FIG. 7A, a reaction was carried out on a 0.2 mmol scale in a 0.5 dram vial; in FIG. 7B, a reaction was carried out on a 0.5 mmol scale in a 1 dram vial; and, in FIG. 7C, a reaction was carried out on a 7 mmol scale in a 50 mL flask.

6. We have found that commercially available malonic half esters often contain more of the malonic diester than indicated. Simple basic extration followed by neutralization and re-extraction provides high purity mono acid.

7. The reaction tolerates the presence of diol impurities (10-20%) in crude aryl boronic esters, rigourous purification of the starting materials is not required.

8. 1,2-DCE can be used as the reaction solvent instead of DMA. This can be advantagous for products that are water soluble, as the DCE can be removed by rotovap and the reaction mixtures purified directly by loading onto silica gel.

9. CuI is good catalyst for the standard 3-iodophenyl boronic neopentyl ester substrate, but does not demonstrate broad effectiveness in comparison to Cu(OTf)$_2$ across the range of substrates examined.

10. Under non-optimal conditions, oxidative degradation and decarboxylation of the substrate is observed. The volatility and/or high polarity of these products make exact quantification difficult.

11. Less successful substrates under the standard reaction conditions with mono-ethyl malonate include: 4-methoxyphenyl boronic neopentyl ester (29% yield with 100% Cu), 3,5-dimethoxyphenyl boronic neopentyl ester (58% yield with 100% Cu), 2-(5-bromothiophenyl) boronic neopentyl ester (no product observed), 3-thiophenyl boronic neopentyl ester (<10% product observed), 4-pyridyl boronic neopentyl ester (<10% product observed).

12. When the reaction is conducted under pure O$_2$, oxidative consumption of the substrates and decarboxyation is observed. Homocoupling, aryl boron hydroxylation, and diaryl ether side products are formed under these conditions.

V. ARENE BORYLATION/DECARBOXYLATIVE COUPLING SEQUENCES

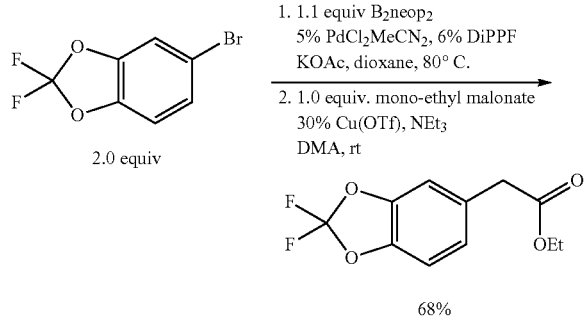

68%

5a Step 1. In a N$_2$-filled glovebox, PdCl$_2$(MeCN)$_2$ (25.9 mg, 0.100 mmol, 0.0500 equiv.), 1,1'-bis(diisopropylphosphino)ferrocene (56.9 mg, 0.120 mmol, 0.0600 equiv.), B$_{2neop2}$ (497 mg, 2.20 mmol, 1.10 equiv.), KOAc (588 mg, 6.00 mmol, 3.00 equiv.) and dioxane (6.0 mL) were added to a 4-dram vial charged with a stir bar. The vial was sealed with a PTFE-lined cap and brought outside glovebox, at which point the corresponding aryl bromide (474 mg, 2.0 mmol, 1.0 equiv.) was added. The reaction was heated at 80° C. for 14 h. The reaction mixture was diluted in hexanes (5.0 mL) and passed through a short pad of silica, washing with CH$_2$Cl$_2$, and then concentrated in vacuo to afford the corresponding crude aryl neopentyl ester which was used in the next step without further purification.

Step 2. Reaction conducted according to the General Procedure A from the corresponding crude neopentyl arylboronic ester (1.00 mmol, 2.00 equiv., half the material from step 1) and mono-ethyl malonate (66.1 mg, 0.500 mmol, 1.00 equiv.) using Cu(OTf)$_2$ (54.3 mg, 0.150 mmol, 0.300 equiv.), 42 h. Isolated in 65% yield after purification by column chromatography (10:1 Hexane/EtOAc) as a light yellow oil.

$^1$H NMR (CDCl$_3$, 500 MHz) δ 7.04 (m, 1H), 7.00-6.97 (m, 2H), 4.16 (q, J=7.2 Hz, 2H), 3.59 (s, 2H), 1.26 (t, J=7.2 Hz, 3H);
$^{13}$C NMR (CDCl$_3$, 125 MHz) δ 171.1, 143.9, 142.9, 131.7 (t, J=256 Hz), 130.1, 124.5, 110.7, 109.3, 61.2, 41.0, 14.2;
$^{19}$F NMR (CDCl$_3$, 469 MHz) δ −50.0;
HRMS (EI): calcd for C$_{11}$H$_{10}$F$_2$O$_4$ [M]$^+$: 244.0547. Found 244.0551.

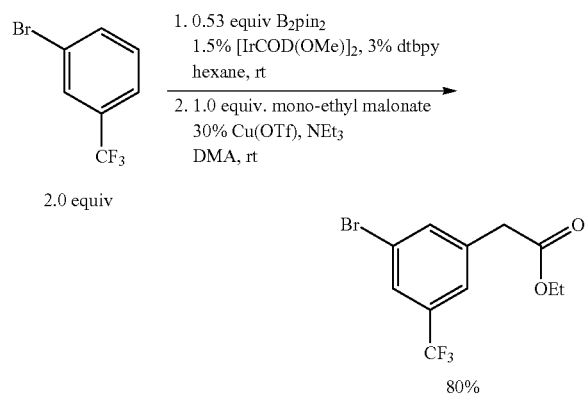

80%

5b Step 1. In a N$_2$-filled glovebox, [Ir(COD)(OMe)]$_2$ (10.0 mg, 0.0150 mmol, 0.0150 equiv.) and 4,4'-di-tert-butyl-2,2'-dipyridyl (7.9 mg, 0.030 mmol, 0.030 mmol, 0.030 equiv.) were added to a 1-dram vial charged with a stir bar. Hexanes (2.0 mL) was added and stirred at room temperature for 10 minutes, at which point arene (225 mg, 1.00 mmol, 1.00 equiv.) and B$_{2pin2}$ (135 mg, 0.530 mmol, 0.530 equiv.) were sequentially added. The vial was sealed with a PTFE-lined cap and stirred at room temperature outside the glovebox. After 10 h, the crude mixture was filtered through a plug of silica and then concentrated in vacuo to afford the corresponding crude aryl pinacol boronic ester which was used in the next step without further purification.

Step 2. Reaction conducted according to the General Procedure A from the crude pinacol boronic ester (2.00 equiv.) and mono-ethyl malonate (66.1 mg, 0.500 mmol, 1.00 equiv.) using Cu(OTf)$_2$ (54.3 mg, 0.150 mmol, 0.300 equiv.), 18 h. Isolated in 80% yield after purification by column chromatography (15:1 Hexane/EtOAc) as a light yellow oil.

$^1$H NMR (CDCl$_3$, 500 MHz) δ 7.68 (s, 1H), 7.64 (s, 1H), 7.49 (s, 1H), 4.18 (q, J=7.1 Hz, 2H), 3.64 (s, 2H), 1.27 (t, J=7.2 Hz, 3H);
$^{13}$C NMR (CDCl$_3$, 125 MHz) δ 170.2, 137.1, 135.9, 132.5 (q, J=33 Hz), 127.3, 125.0, 123.1 (q, J=274 Hz), 122.8, 61.4, 40.6, 14.1;
$^{19}$F NMR (CDCl$_3$, 469 MHz) δ −62.8;
HRMS (EI): calcd for C$_{11}$H$_{10}$BrF$_3$O$_2$[M]$^+$: 309.9816. Found 309.9816.

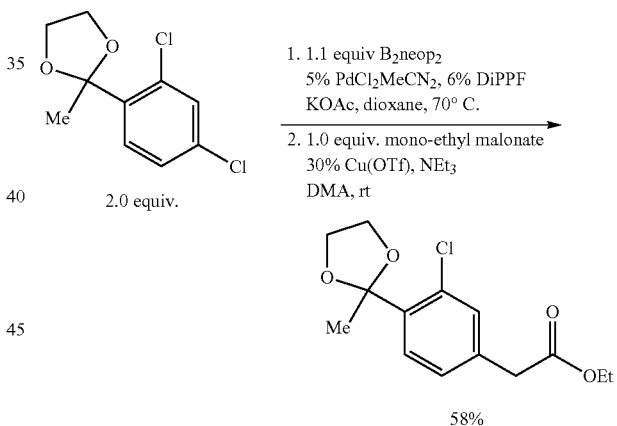

58%

5d Step 1. In a N$_2$-filled glovebox, PdCl$_2$(MeCN)$_2$ (13 mg, 0.050 mmol, 0.050 equiv.), 1,1'-bis(diisopropylphosphino)ferrocene (28 mg, 0.060 mmol, 0.060 equiv.), and dioxane (3.0 mL) were added to a 4-dram vial charged with a stir bar. The corresponding aryl chloride (233 mg, 1.00 mmol, 1.00 equiv.), B$_{2neop2}$ (270 mg, 1.20 mmol, 1.20 equiv.), and KOAc (294 mg, 3.00 mmol, 3.00 equiv.) were sequentially added. The vial was sealed with a PTFE-lined cap and heated at 70° C. outside the glovebox for 6 h. The reaction mixture was diluted with EtOAc and washed sequentially with sat. aq. NaHCO3 and brine. The organic layer was dried with Na2SO4, filtered over celite and concentrated in vacuo to afford the corresponding crude neopentyl ester which was used in the next step without further purification.

Step 2. Reaction conducted according to the General Procedure A from the corresponding crude neopentyl arylboronic ester (1.00 mmol, 2.00 equiv.) and mono-ethyl malonate (66.1 mg, 0.500 mmol, 1.00 equiv.) using Cu(OTf)$_2$ (54.3 mg, 0.150 mmol, 0.300 equiv.), 28 h. Isolated in 58% yield after purification by column chromatography (10:1 to 2:1 pentane/Et$_2$O) as a thick colorless oil.

$^1$H NMR (CDCl$_3$, 500 MHz) δ 7.58 (m, 1H), 7.32 (m, 1H), 7.15 (m, 1H), 4.17 (q, J=7.1 Hz, 2H), 4.06 (m, 2H), 3.78 (m, 2H), 3.57 (s, 2H), 1.79 (s, 3H), 1.27 (t, J=7.2 Hz, 3H);

$^{13}$C NMR (CDCl$_3$, 175 MHz) δ 171.0, 138.4, 135.6, 132.2, 132.0, 127.9, 127.5, 108.4, 64.5, 61.2, 40.5, 25.3, 14.2;

HRMS (LCMS ESI): calcd for C$_{14}$H$_{17}$ClNaO$_4$ [M+Na]$^+$: 307.0708. Found 307.0706.

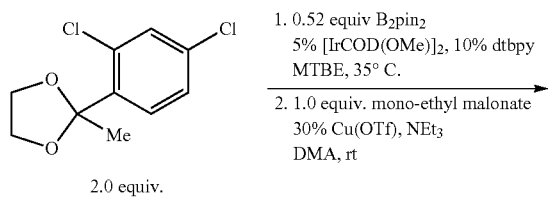

2.0 equiv.

1. 0.52 equiv B$_2$pin$_2$
   5% [IrCOD(OMe)]$_2$, 10% dtbpy
   MTBE, 35° C.
2. 1.0 equiv. mono-ethyl malonate
   30% Cu(OTf), NEt$_3$
   DMA, rt The organic layer was dried with Na$_2$SO$_4$, filtered over celite and concentrated in vacuo to afford the corresponding crude pinacol boronic ester, which was used in the next step without further purification.

Step 2. Reaction conducted according to the General Procedure A from the crude pinacol boronic ester (2.00 equiv.) and mono-ethyl malonate (66.1 mg, 0.500 mmol, 1.00 equiv.) using Cu(OTf)$_2$ (54.3 mg, 0.150 mmol, 0.300 equiv.), 24 h. Isolated in 60% yield after purification by column chromatography (10:1 Hexane/EtOAc) as a colorless oil.

$^1$H NMR (CDCl$_3$, 500 MHz) δ 7.56 (s, 1H), 7.43 (s, 1H), 4.18 (q, J=7.0 Hz, 2H), 4.09-4.03 (m, 2H), 3.82-3.75 (m, 2H), 3.73 (s, 2H), 1.77 (s, 3H), 1.27 (t, J=7.2 Hz, 3H);

$^{13}$C NMR (CDCl$_3$, 125 MHz) δ 170.2, 138.5, 134.6, 131.8, 131.5, 131.0, 130.5, 108.1, 64.5, 61.2, 38.7, 25.3, 14.2;

HRMS (LCMS ESI): calcd for C$_{14}$H$_{16}$Cl$_2$NaO$_4$ [M+Na]$^+$: 341.0318. Found 341.0316.

VI. APPLICATIONS IN COMPLEX MOLECULE SYNTHESIS AND DIVERSIFICATION

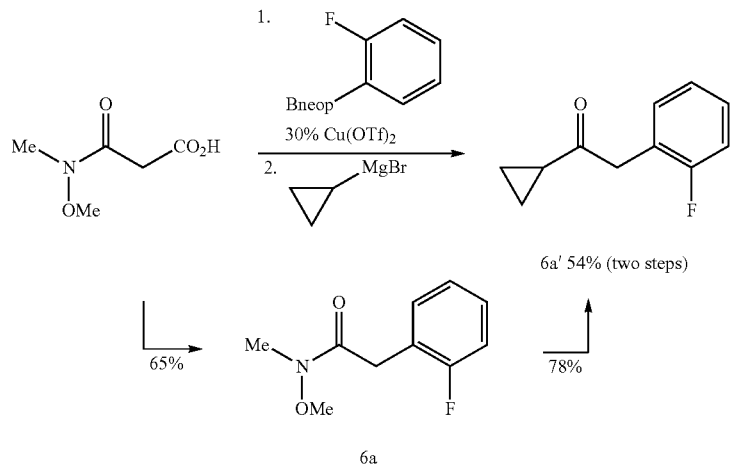

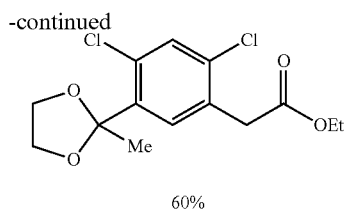

60%

5e Step 1. In a N2-filled glovebox, [Ir(COD)(OMe)]$_2$ (33.2 mg, 0.0500 mmol, 0.0500 equiv.) and 4,4'-di-tert-butyl-2,2'-dipyridyl (26.8 mg, 0.100 mmol, 0.100 equiv.) were added to a 1-dram vial charged with a stir bar. MTBE (2.0 mL) was added and stirred at room temperature for 10 minutes, at which point arene (233 mg, 1.00 mmol, 1.00 equiv.) and B$_{2pin2}$ (132 mg, 0.520 mmol, 0.520 equiv.) were sequentially added. The vial was sealed with a PTFE-lined cap and stirred at 35° C. outside the glovebox. After 72 h, the crude mixture was diluted in EtOAc and sequentially washed with sat. aq. NaHCO$_3$, sat. aq. NaOAc, and brine.

6a' Step 1 (6a). The decarboxylative coupling was conducting according to the General Procedure A from the corresponding neopentyl boronic ester (312 mg, 1.50 mmol, 3.00 equiv.) and 3-(methoxy(methyl)amino)-3-oxopropanoic acid (73.6 mg, 0.500 mmol, 1.00 equiv.) using Cu(OTf)$_2$ (54.3 mg, 0.150 mmol, 0.300 equiv.), 80 h. Isolated in 65% yield after purification by column chromatography (3:2 Hexane/EtOAc) as a light yellow oil.

$^1$H NMR (CDCl$_3$, 500 MHz) δ 7.33-7.24 (m, 2H), 7.14-7.05 (m, 2H), 3.83 (s, 2H), 3.70 (s, 3H), 3.23 (s, 3H);

$^{13}$C NMR (CDCl$_3$, 125 MHz) δ; 171.4, 161.0 (d, J=249 Hz), 131.4, 128.6, 124.0, 122.2, 115.2, 61.2, 32.2 (2C);

$^{19}$F NMR (CDCl$_3$, 377 MHz) δ -117.7;

HRMS (LCMS ESI): calcd for C$_{10}$H$_{13}$FNO$_2$ [M+H]$^+$: 198.0925. Found 198.0926.

Step 2 (6a') To a 1-dram vial sealed with a PTFE-lined cap under N2 was added cyclopropyl magnesium bromide (1.37 mL, 0.365 M in THF, 2.2 equiv.). The corresponding weinreb amide (46.0 mg, 0.230 mmol, 1.0 equiv.) was added as a solution in THF (0.17 mL), using additional THF rinces (0.30 mL). The solution was heated at 45° C. for 1 hour. The mixture was cooled to 0° C. and quenched with 1 M HCl solution (1.0 mL). Additional water (5 mL) was added and then the reaction was extracted with EtOAc (3×10 mL EtOAc). The organic layer was washed with brine (5 mL) and water (5 mL), then dried with Na$_2$SO$_4$, and concentrated in vacuo. The crude mixture was passed through a plug of silica, washing with 10:1 hexane/EtOAc, then concentrated to afford the title compound (78% yield) as a light yellow oil. Spectroscopic data agreed with that reported.17

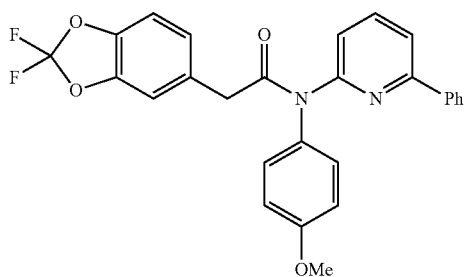 [SMILES: COc1ccc(N(C(=O)Cc2ccc3c(c2)OC(F)(F)O3)c2cccc(-c3ccccc3)n2)cc1]

6b Prepared according to the General Procedure A from the corresponding neopentyl boronic ester (108 mg, 0.400 mmol, 2.00 equiv.) and 3-((4-methoxyphenyl)(6-phenylpyridin-2-yl)amino)-3-oxopropanoic acid (85.3 mg, 0.200 mmol, 1.00 equiv., 85% pure (w/w)) using Cu(OTf)$_2$ (36.3 mg, 0.100 mmol, 0.500 equiv.), 44 h. Isolated in 74% yield after purification by column chromatography (65:35 Hexane/EtOAc) as a light yellow oil.

$^1$H NMR (CDCl$_3$, 500 MHz) δ 7.90-7.87 (m, 2H), 7.71 (m, 1H), 7.59 (m, 1H), 7.45-7.37 (m, 3H), 7.30-7.20 (m, 3H), 6.95-6.90 (m, 4H), 6.80 (m, 1H), 3.84 (s, 3H), 3.78 (s, 2H);

$^{13}$C NMR (CDCl$_3$, 125 MHz) δ 171.4, 159.0, 156.1, 154.8, 143.7, 142.6, 138.6, 138.2, 134.3, 131.6 (t, J=254 Hz), 131.2, 129.8, 129.3, 128.7, 126.7, 124.4, 119.0, 117.6, 114.5, 110.7, 109.0, 55.5, 42.2;

$^{19}$F NMR (CDCl$_3$, 469 MHz) δ −49.9;

HRMS (LCMS ESI): calcd for C$_{27}$H$_{20}$F$_2$N$_2$NaO$_4$ [M+Na]$^+$: 497.1283. Found 497.1294.

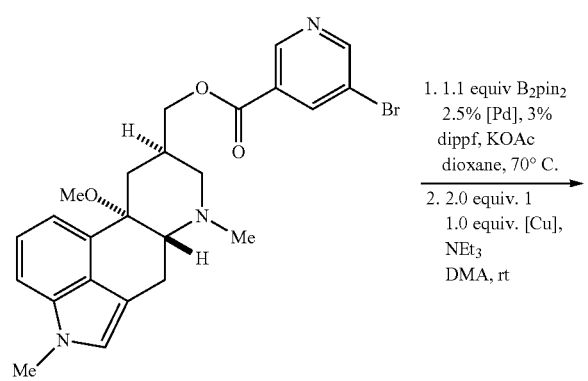

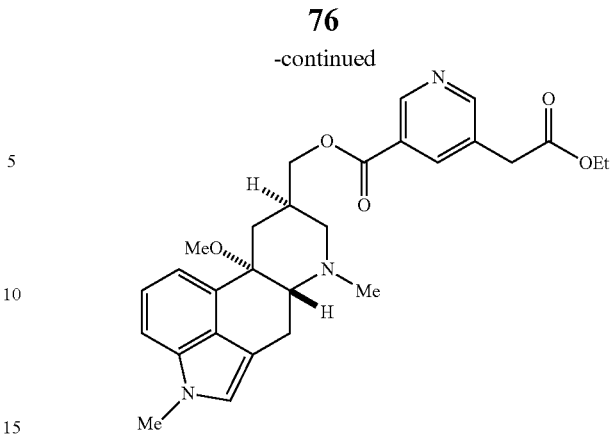

7a In a N$_2$-filled glovebox, PdCl$_2$(MeCN)$_2$ (3.6 mg, 0.014 mmol, 0.025 equiv.), 1,1′-Bis(diisopropylphosphino)ferrocene (7.0 mg, 0.017 mmol, 0.030 equiv.), and dioxane (1.5 mL) were added to a 1-dram vial charged with a stir bar. The corresponding aryl bromide (271 mg, 0.560 mmol, 1.00 equiv.), B$_{2pin2}$ (156 mg, 0.620 mmol, 1.10 equiv.), and KOAc (165 mg, 1.68 mmol, 3.00 equiv.) were sequentially added. The vial was sealed with a PTFE-lined cap and heated at 70° C. outside the glovebox for 4 h. The reaction mixture was passed through a plug of celite, washing with toluene (50 mL). The organic layer was sequentially washed with sat. NaHCO$_3$ (20 mL) and brine (3×20 mL), and then dried with NaSO4. The solvent was removed in vacuo to afford the corresponding pinacol arylboronic ester as a pale brown solid, 97% yield.

Step 2. Prepared according to the General Procedure A from the corresponding pinacol arylboronic ester (66.4 mg, 0.125 mmol, 1.00 equiv.) and mono-ethyl malonate (33.0 mg, 0.250 mmol, 2.00 equiv.) using Cu(OTf)$_2$ (45.2 mg, 0.125 mmol, 1.00 equiv.) and Et$_3$N (0.17 mL, 1.25 mmol, 10 equiv.), 25 h. Isolated in 57% yield after purification by column chromatography (4% to 6% MeOH in CH$_2$Cl$_2$/MeCN/Hexanes (2:1:1), 1% NH$_4$Cl additive) as a colorless oil.

$^1$H NMR (CDCl$_3$, 500 MHz) δ 9.15 (s, 1H), 8.70 (s, 1H), 8.25 (m, 1H), 7.24 (m, 1H), 7.20 (m, 1H), 7.05 (m, 1H), 6.80 (s, 1H), 4.40 (m, 1H), 4.30 (m, 1H), 4.18 (q, J=7.1 Hz, 2H), 3.78 (s, 3H), 3.69 (s, 2H), 3.26-3.19 (m, 2H), 3.06-2.96 (m, 5H), 2.65 (br, 1H), 2.49 (s, 3H), 2.39 (br, 1H), 2.13 (br, 1H), 1.39 (t, J=13 Hz, 1H), 1.26 (t, J=7.2 Hz, 3H);

$^{13}$C NMR (CDCl$_3$, 125 MHz) δ 170.2, 165.1, 154.2, 149.6, 137.9, 135.2, 130.0, 129.6, 126.3, 125.9, 123.3, 121.5, 115.0, 110.2, 109.0, 73.6, 70.1, 68.1, 61.5, 60.6, 49.6, 43.9, 38.2, 32.8, 31.5, 30.2, 22.3, 14.2;

HRMS (LCMS ESI): calcd for C$_{28}$H$_{34}$N$_3$O$_5$ [M+H]$^+$: 492.2493. Found 492.2494.

-continued

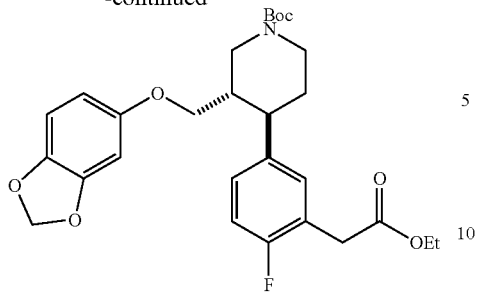

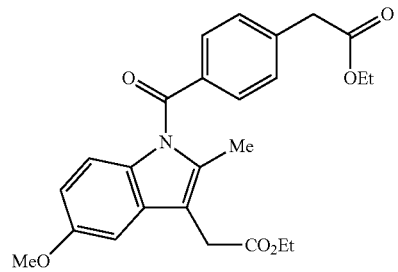

7b 63%

7b Step 1. In a N₂-filled glovebox, [Ir(COD)(OMe)]₂ (15 mg, 0.023 mmol, 0.050 equiv.) and 4,4'-di-tert-butyl-2,2'-dipyridyl (12 mg, 0.045 mmol, 0.10 equiv.) were added to a 1-dram vial charged with a stir bar. MTBE (1.5 mL) was added and stirred at room temperature for 10 minutes, at which point arene (195 mg, 0.450 mmol, 1.00 equiv.) and $B_{2pin2}$ (114 mg, 0.450 mmol, 1.0 equiv.) were sequentially added. The vial was sealed with a PTFE-lined cap and stirred at 45° C. outside the glovebox. After 16 h, the crude mixture was concentrated, dissolved in 6 mL 2:1 MeOH/CH₂Cl₂, and heated at 70° C. After 120 h, the crude mixture was concentrated. Isolated in 22% yield (38% yield based on recovered arene) after purification by column chromatography (10:1 to 4:1 Hexane/EtOAc) as a white solid.

Step 2. Prepared according to the General Procedure A from the corresponding pinacol arylboronic ester (48 mg, 0.086 mmol, 1.00 equiv.) and mono-ethyl malonate (23 mg, 0.17 mmol, 2.00 equiv.) using Cu(OTf)₂ (31 mg, 0.086 mmol, 1.00 equiv.) and Et₃N (0.12 mL, 0.86 mmol, 10 equiv.), 23 h. Isolated in 45% yield (76% yield based on recovered arene) after purification by column chromatography (10:1 to 4:1 Hexane/EtOAc) as a colorless oil.

¹H NMR (CDCl₃, 500 MHz, 65° C.) δ 7.09-7.04 (m, 2H), 6.97 (t, J=9.2 Hz, 1H), 6.61 (d, J=8.6 Hz, 1H), 6.35 (m, 1H), 6.16 (m, 1H), 5.86 (s, 2H), 4.43 (m, 1H), 4.24 (m, 1H), 4.15 (q, J=7.1 Hz, 2H), 3.64 (m, 1H), 3.60 (s, 2H), 3.49 (m, 1H), 2.84-2.76 (m, 2H), 2.65 (m, 1H), 2.01 (m, 1H), 1.81 (m, 1H), 1.71 (m, 1H), 1.50 (s, 9H), 1.23 (t, J=7.1 Hz, 3H);

¹³C NMR (CDCl₃, 500 MHz, 65° C.) δ 170.5, 160.0 (d, J=244 Hz), 154.9, 154.6, 148.4, 142.0, 139.4 (d, J=3.6 Hz), 130.5 (d, J=4.1 Hz), 127.8 (d, J=8.1 Hz), 121.9 (d, J=16 Hz), 115.5 (d, J=22 Hz), 108.0, 106.3, 101.2, 98.4, 79.7, 69.4, 61.0, 47.5, 44.5, 44.4, 42.1, 34.6 (d, J=2.9 Hz), 34.1, 28.6, 14.2;

¹⁹F NMR (CDCl₃, 468 MHz, 65° C.) δ -120.3;

HRMS (LCMS ESI): calcd for C₂₈H₃₄FNNaO₇ [M+Na]⁺: 538.2212. Found 538.2212.

7c Step 1. In a N2-filled glovebox, PdCl₂(MeCN)₂ (13 mg, 0.050 mmol, 0.050 equiv.), 1,1'-bis(diisopropylphosphino)ferrocene (28 mg, 0.060 mmol, 0.060 equiv.), and dioxane (3.0 mL) were added to a 4-dram vial charged with a stir bar. Indometacin ethyl ester (386 mg, 1.00 mmol, 1.00 equiv.), $B_{2neop2}$ (249 mg, 1.10 mmol, 1.10 equiv.), and KOAc (294 mg, 3.00 mmol, 3.00 equiv.) were sequentially added. The vial was sealed with a PTFE-lined cap and heated at 100° C. outside the glovebox for 2.5 h. The reaction mixture was diluted with EtOAc and washed sequentially with sat. aq. NaHCO3 and brine. The organic layer was dried with Na₂SO₄, filtered over celite and concentrated in vacuo. Azeoptropical removal of trace water with toluene afforded the corresponding crude aryl neopentyl ester which was used in the next step without further purification.

Step 2. The reaction was conducted according to the General Procedure A from the corresponding crude neopentyl boronic ester (1.00 mmol, 2.00 equiv.) and mono-ethyl malonate (66.1 mg, 0.500 mmol, 1.00 equiv.) using Cu(OTf)₂ (54.3 mg, 0.150 mmol, 0.300 equiv.), 68 h. Isolated in 63% yield after purification by column chromatography (7:3 Hexane/EtOAc) as an off-white solid.

¹H NMR (CDCl₃, 500 MHz) δ 7.69-7.67 (m, 2H), 7.41-7.39 (m, 2H), 6.97 (m, 1H), 6.90 (m, 1H), 6.65 (m, 1H), 4.21-4.14 (m, 4H), 3.84 (s, 3H), 3.71 (s, 2H), 3.65 (s, 2H), 2.37 (s, 3H), 1.28-1.24 (m, 6H);

¹³C NMR (CDCl₃, 125 MHz) δ 171.0, 170.7, 169.2, 156.0, 139.4, 136.0, 134.4, 131.0, 130.6, 130.1, 129.7, 115.1, 112.4, 111.6, 101.2, 61.2, 61.0, 55.8, 41.5, 30.5, 14.3, 14.2, 13.4;

HRMS (LCMS ESI): calcd for C₂₅H₂₇NNaO₆ [M+Na]⁺: 460.1731. Found 460.1731.

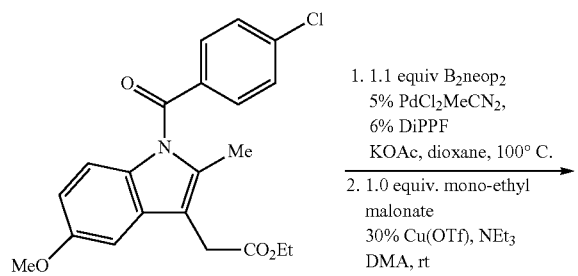

1. 1.1 equiv B₂neop₂
   5% PdCl₂MeCN₂,
   6% DiPPF
   KOAc, dioxane, 100° C.
2. 1.0 equiv. mono-ethyl malonate
   30% Cu(OTf), NEt₃
   DMA, rt

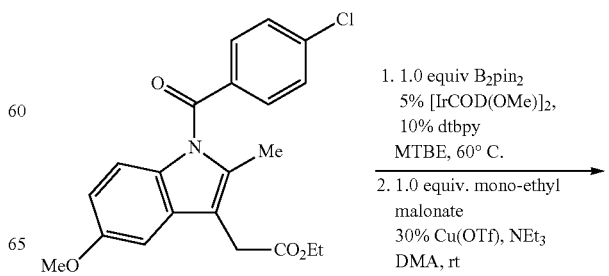

1. 1.0 equiv B₂pin₂
   5% [IrCOD(OMe)]₂,
   10% dtbpy
   MTBE, 60° C.
2. 1.0 equiv. mono-ethyl malonate
   30% Cu(OTf), NEt₃
   DMA, rt

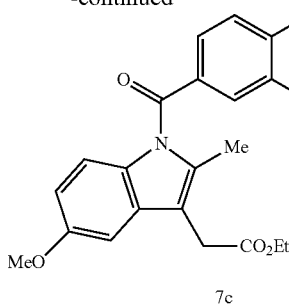

7c

7c Step 1. In a N2-filled glovebox, [Ir(COD)(OMe)]$_2$ (9.9 mg, 0.015 mmol, 0.050 equiv.) and 4,4'-Di-tert-butyl-2,2'-dipyridyl (8.0 mg, 0.030 mmol, 0.10 equiv.) were added to a 1-dram vial charged with a stir bar. MTBE (1.0 mL) was added and stirred at room temperature for 10 minutes, at which point arene (116 mg, 0.300 mmol, 1.00 equiv.) and B$_{2pin2}$ (76.2 mg, 0.300 mmol, 1.0 equiv.) were sequentially added. The vial was sealed with a PTFE-lined cap and stirred at 60° C. outside the glovebox. After 4 h, the crude mixture was concentrated and passed through a short silica column (4:1 to 1:1 Hexane/EtOAc). Isolated in 43% yield as a pale yellow oil.

Step 2. The reaction was conducting according to the General Procedure A from the corresponding pinacol arylboronic ester (123 mg, 0.24 mmol, 2.00 equiv.) and monoethyl malonate (15.9 mg, 0.120 mmol, 1.00 equiv.) using Cu(OTf)$_2$ (13.0 mg, 0.0360 mmol, 0.300 equiv.), 40 h. Isolated in 53% yield after purification by column chromatography (4:1 to 2:1 Hexane/EtOAc) as a light yellow oil.

$^1$H NMR (CDCl$_3$, 500 MHz) δ 7.67 (m, 1H), 7.61 (m, 1H), 7.53 (m, 1H), 6.99 (m, 1H), 6.96 (m, 1H), 6.70 (m, 1H), 4.21-4.16 (m, 4H), 3.86 (s, 3H), 3.82 (s, 2H), 3.67 (s, 2H), 2.39 (s, 3H), 1.30-1.25 (m, 6H);

$^{13}$C NMR (CDCl$_3$, 125 MHz) δ 170.9, 169.8, 168.2, 156.1, 139.5, 135.9, 134.3, 133.6, 132.8, 130.9, 130.7, 130.0, 129.9, 115.1, 112.8, 111.8, 101.3, 61.3, 61.0, 55.7, 39.1, 30.5, 14.3, 14.2, 13.4;

HRMS (LCMS ESI): calcd for C$_{25}$H$_{26}$ClNNaO$_6$ [M+Na]$^+$: 494.1341. Found 494.1345

VII. REFERENCES

1. Still, W. C.; Kahn, M.; Mitra, A., J. Org. Chem. 1978, 43, 2923-2925.
2. Matthew, S. C.; Glasspoole, B. W.; Eisenberger, P.; Crudden, C. M., J. Am. Chem. Soc. 2014, 136, 5828-5831.
3. Huang, Y-J.; Jiang, Y-B.; Bull, S. D.; Fossey, J. S.; James T. D., Chem. Commun. 2010, 46, 8180-8182.
4. Yin, G.; Kalvet, I.; Englert, U.; Schoenebeck, F., J. Am. Chem. Soc. 2015, 137, 4164-4172.
5. Thietiot-Laurent, S. A. L.; Nadal, B.; Le Gall, T., Synthesis 2010, 10, 1697-1701.
6. Cordes, J.; Calo, F.; Anderson, K.; Pfaffeneder, T.; Laclef, S.; White, A. J. P.; Barrett, A. G. M., J. Org. Chem. 2012, 77, 652-657.
7. Chen, Y.; Sieburth, S. McN., Synthesis 2002, 15, 2191-2194.
8. Ryu, Y.; Scott, A. I., Tetrahedron Lett. 2003, 44, 7499-7502.
9. Marom, E.; Mizhiritskii, M.; Rubnov, S., Intermediate Compounds and Processes for the Preperation of Quinoline Derivatives such as Laquinimob Sodium. WO 2012070051 A1, May 31, 2012.
10. Patel, D. V.; Young, M. G.; Robinson, S. P.; Hunihan, L.; Dean, B. J.; Gordon, E. M., J. Med. Chem. 1996, 39, 4197-4210.
11. Redman-Furey, N. L.; Godlewski, J. E.; Dicks, M. L., Malate salts, and polymorphs of (3S,5S)-7-[3-amino-5-methyl-piperidinyl]-1-cyclopropyl-1,4-dihydro-8-methoxy-4-oxo-3-quinolinecarboxylic acid. US Patent 232650 A1, Oct. 4, 2007.
12. Ramaprasad, G. C.; Kalluraya, B.; Kumar, B. S.; Hunnur, R. K., Eur. J. Med. Chem. 2010, 45, 4587-4593.
13. Xie, P.; Xie, P. Y.; Qian, B.; Zhou, H.; Xia, C.; Huang, H., J. Am. Chem. Soc. 2012, 134, 9902-9905.
14. Feng, Y.; W. Wu, W.; Xu, Z.; Li, Y.; Li, M.; Xu, H., Tetrahedron 2012, 68, 2113-2120.
15. Zimmermann, B.; Dzik, W. I.; Himmler, T.; Goossen, L. J., J. Org. Chem. 2011, 76, 8107-8112.
16. Penga, Z.; Wang, J.; Cheng, J.; Xie, X.; Zhang, Z., Tetrahedron 2010, 66, 8238-8241.
17. Manne, S.; Srinivasan, T.; Sajja, E.; Karamala, R.; Bairy, K.; Ghojala, V., Processes for Preparing Prasugrel and Pharmaceutically Acceptable Salts Thereof. US Patent 2012202066 A1, Aug. 9, 2012.

1. (a) Staunton, J.; Weissman, K. J., Nat. Prod. Rep. 2001, 18, 380-416; (b) Smith, S.; Tsai, S.-C., Nat. Prod. Rep. 2007, 24, 1041-1072.
2. (a) Weaver, J. D.; Recio, A., III; Grenning, A. J.; Tunge, J. A., Chem. Rev. 2011, 111, 1846-1913; (b) Rodriguez, N.; Goossen, L. J., Chem. Soc. Rev. 2011, 40, 5030-5048; (c) Nakamura, S., Org. Biomol. Chem. 2014, 12, 394-405; (d) Pan, Y. H.; Tan, C. H., Synthesis 2011, 2044-2053.
3. (a) Lalic, G.; Aloise, A. D.; Shair, M. D., J. Am. Chem. Soc. 2003, 125, 2852-2853; (b) Magdziak, D.; Lalic, G.; Lee, H. M.; Fortner, K. C.; Aloise, A. D.; Shair, M. D., J. Am. Chem. Soc. 2005, 127, 7284-7285; (c) Blaquiere, N.; Shore, D. G.; Rousseaux, S.; Fagnou, K., J. Org. Chem. 2009, 74, 6190-6198; (d) Walker, M. C.; Thuronyi, B. W.; Charkoudian, L. K.; Lowry, B.; Khosla, C.; Chang, M. C. Y., Science 2013, 341, 1089-1094; (e) Saadi, J.; Wennemers, H., Nature Chem. 2016, 8, 276-280; (f) Behenna, D. C.; Liu, Y. Y.; Yurino, T.; Kim, J.; White, D. E.; Virgil, S. C.; Stoltz, B. M., Nature Chem. 2012, 4, 130-133; (g) Bae, H. Y.; Sim, J. H.; Lee, J. W.; List, B.; Song, C. E., Angew. Chem. Int. Ed. 2013, 52, 12143-12147; (h) Li, C. K.; Breit, B., J. Am. Chem. Soc. 2014, 136, 862-865; (i) Bahlinger, A.; Fritz, S. P.; Wennemers, H., Angew. Chem. Int. Ed. 2014, 53, 8779-8783.
4. (a) Shang, R.; Ji, D.-S.; Chu, L.; Fu, Y.; Liu, L., Angew. Chem. Int. Ed. 2011, 50, 4470-4474; (b) Feng, Y.-S.; Wu, W.; Xu, Z.-Q.; Li, Y.; Li, M.; Xu, H.-J., Tetrahedron 2012, 68, 2113-2120. (c) For the Cu/Mg promoted decarboxylative coupling of iodopyridines and a malonic half-ester at 100° C.: Ho, J. Z.; Braun, M. P., J. Label Compd. Radiopharm. 2007, 50, 277-280. For examples of Pd-catalyzed cross-coupling of malonates followed by thermal dealkyoxycarbonylation or deacylation see: d) Song, B. R.; Rudolphi, F.; Himmler, T.; Goossen, L. J., Adv. Synth. Catal. 2011, 353, 1565-1574 e) Zeevaart, J. G.; Parkinson, C. J.; de Koning, C. B.; Tetrahedron Lett. 2007, 48, 3289-3293. For the decarboxylative coupling of oxalate monoesters with aryl boron reagents see (f) Miao, J.-M.; Fang, P.; Jagdeep, S.; and Ge, H.-B. Org. Chem. Front. 2016, 3, 243-250.
5. Limited to t-Bu esters: (a) Biscoe, M. R.; Buchwald, S. L., Org. Lett. 2009, 11, 1773-1775; (b) Jorgensen, M.; Lee, S.; Liu, X. X.; Wolkowski, J. P.; Hartwig, J. F., J. Am. Chem. Soc. 2002, 124, 12557-12565.
6. (a) Kosugi, M.; Negishi, Y.; Kameyama, M.; Migita, T., Bull. Chem. Soc. Japan 1985, 58, 3383-3384; (b) Agnelli, F.; Sulikowski, G. A., Tetrahedron Lett. 1998, 39, 8807-8810; (c) Hama, T.; Liu, X. X.; Culkin, D. A.; Hartwig, J. F., J. Am. Chem. Soc. 2003, 125, 11176-11177.
7. Alternative approaches: cross-coupling of a-halo esters and aryl nucleophiles (a) Goossen, L. J., Chem. Commun. 2001, 669-670; photoredox approaches (b) Jang, H. L.; Kim, H. T.; Cho, E. J.; Joo, J. M. Asian J. Org. Chem. 2015, 4, 1386-1391; metal catalyzed carbonylations of benzyl halides (c) Giroux, A.; Nadeau, C.; Han, Y. X., Tetrahedron Lett. 2000, 41, 7601-7604; iodide and acid mediated reductions of mendelic acids (d) Milne, J. E.; Storz, Colyer, T. J.; Thiel, O. R.; Seran, M. D.; Larsen, R. D.; Murry, J. A. J. Org. Chem. 2011, 76, 9519-9524; oxidative deaminative arylation with aryl boronic acids (e) Wu, G. J.; Deng, Y. F.; Wu, C. Q.; Zhang, Y.; Wang, J. B.; Angew. Chem. Int. Ed. 2014, 53, 10510-10514; and silyl ketene acetal arylation with pyridine N-oxides (f) Londregan, A. T.; Burford, K.; Conn, E. L.; Hesp, K. D., Org. Lett. 2014, 16, 3336-3339.
8. (a) Zuo, Z. W.; Ahneman, D. T.; Chu, L. L.; Terrett, J. A.; Doyle, A. G.; MacMillan, D. W. C., Science 2014, 345, 437-440; (b) Zuo, Z. W.; MacMillan, D. W. C., J. Am. Chem. Soc. 2014, 136, 5257-5260.
9. (a) Cornella, J.; Edwards, J. T.; Qin, T.; Kawamura, S.; Wang, J.; Pan, C. M.; Gianatassio, R.; Schmidt, M.; Eastgate, M. D.; Baran, P. S., J. Am. Chem. Soc. 2016, 138, 2174-2177; (b) Huihui, K. M. M.; Caputo, J. A.; Melchor, Z.; Olivares, A. M.; Spiewak, A. M.; Johnson, K. A.; DiBenedetto, T. A.; Kim, S.; Ackerman, L. K. G.; Weix, D. J., J. Am. Chem. Soc. 2016, 138, 5016-5019; (c) Wang, J.; Qin, T.; Chen, T.-G.; Wimmer, L.; Edwards, J. T.; Cornella, J.; Vokits, B.; Shaw, S. A.; Baran, P. S., Angew. Chem. Int. Ed. 2016, 55, 9676-9679.
10. C—C bond formation preceeds decarboxylation in Cu-catalyzed decarboxylative aldol reactions: Fortner, K. C.; Shair, M. D., J. Am. Chem. Soc. 2007, 129, 1032-1033.
11. Shi, W.; Liu, C.; Lei, A. W., Chem. Soc. Rev. 2011, 40, 2761-2776.
12. Qiao, J. X.; Lam, P. Y. S., In Boronic Acids: Preparation and Applications in Organic Synthesis, Medicine and Materials, 2 ed.; Hall, D. G., Ed. Wiley-VCH Verlag GmbH & Co. KGaA: Weinheim, 2011; 315-361.
13. (a) Stevens, J. M.; MacMillan, D. W. C., J. Am. Chem. Soc. 2013, 135, 11756-11759; (b) Moon, P. J.; Halperin, H. M.; Lundgren, R. J., Angew. Chem. Int. Ed. 2016, 55, 1894-1898.
14. Huang, F.; Quach, T. D.; Batey, R. A., Org. Lett. 2013, 15, 3150-3153.
15. Guo, F. H.; Clift, M. D.; Thomson, R. J., Eur. J. Org. Chem. 2012, 4881-4896.
16. N-Methylpyrrolidine (33%), N(n-Pr)3 (40%), DIPEA (71%), and DABCO (21%) provide lower yields under the standard conditions.
17. Ishiyama, T.; Murata, M.; Miyaura, N., J. Org. Chem. 1995, 60, 7508-7510.
18. Ishiyama, T.; Takagi, J.; Hartwig, J. F.; Miyaura, N., Angew. Chem. Int. Ed. 2002, 41, 3056-3058.
19. Preliminary mechanistic studies are suggestive of a Chan-Evans-Lam type redox pathway in which C—C bond forming reductive elimination is followed by decarboxylation. For a detailed mechanistic study of the Chan-Evans-Lam reaction see King, A. E.; Ryland, B. L.; Brunold, T. C.; Stahl, S. S., Organometallics 2012, 31, 7948-7957.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method for decarboxylative carbonyl α-arylation, comprising: reacting
    a. an aryl coupling partner,
    b. a beta-carbonyl carboxylic acid, and
    c. a copper based catalyst
    the reaction taking place at room temperature, exposed to air, thereby creating a carbon-carbon bond.
2. The method of claim 1, wherein said carboxylic acid is a malonic acid derivative.
3. The method of claim 1, wherein said carboxylic acid is a malonate ester, monoethyl malonate, monobenzyl malonate, mono-1-chlorohexyl malonate, mono-4-NBoc-piperidyl malonate, mono-geranyl malonate, 3-(methyl(phenyl)amino)-3-oxopropanoic acid, 3-oxo-3-(phenylamino) propanoic acid, 3-oxo-3-(pyrrolidin-1-yl)propanoic acid, or 3-(methoxy(methyl)amino)-3-oxopropanoic acid.
4. The method of claim 1, wherein said coupling partner is an arylboronic ester or heteroaryl boronic ester.
5. The method of claim 1, wherein said coupling partner is 3-iodophenyl boronic neopentyl ester [B(neop)], $(ArBO)_3$, $ArB(OH)_2$, ArBpin, or $ArBF_3K$.
6. The method of claim 1, wherein said copper based catalyst is a Cu(I) salt.
7. The method of claim 1, wherein said copper based catalyst is a Cu(II) salt.
8. The method of claim 1, wherein said copper based catalyst is $Cu(OTf)_2$, $Cu(OAc)_2$, $CuSO_4$, $Cu(MeCN)_4PF_6$, or CuI.

* * * * *